(12) United States Patent
Shaw et al.

(10) Patent No.: US 10,253,039 B2
(45) Date of Patent: Apr. 9, 2019

(54) INHIBITORS OF BACTERIAL DNA GYRASE WITH EFFICACY AGAINST GRAM-NEGATIVE BACTERIA

(71) Applicants: THE REGENTS OF THE UNIVERSITY OF CALIFORNIA, Oakland, CA (US); WISCONSIN ALUMNI RESEARCH FOUNDATION, Madison, WI (US)

(72) Inventors: Jared T. Shaw, Davis, CA (US); Jared T. Moore, Healdsburg, CA (US); Molly R. Fensterwald, San Jose, CA (US); Douglas B. Weibel, Madison, WI (US); Katherine A. Hurley, Madison, WI (US)

(73) Assignees: Wisconsin Alumni Research Foundation, Madison, WI (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/349,962

(22) Filed: Nov. 11, 2016

(65) Prior Publication Data
US 2017/0197981 A1    Jul. 13, 2017

Related U.S. Application Data

(63) Continuation of application No. PCT/US2015/030638, filed on May 13, 2015.
(Continued)

(51) Int. Cl.
| | | |
|---|---|---|
| C07D 417/06 | (2006.01) | |
| C07D 417/10 | (2006.01) | |
| C07D 403/12 | (2006.01) | |
| C07D 403/06 | (2006.01) | |
| C07D 403/10 | (2006.01) | |
| C07D 401/10 | (2006.01) | |
| C07D 401/12 | (2006.01) | |
| C07D 405/06 | (2006.01) | |
| C07D 405/12 | (2006.01) | |
| C07D 409/10 | (2006.01) | |
| C07D 409/12 | (2006.01) | |
| C07D 471/04 | (2006.01) | |
| A61K 31/706 | (2006.01) | |
| A61K 31/435 | (2006.01) | |
| A61K 31/427 | (2006.01) | |
| A61K 31/437 | (2006.01) | |
| A61K 31/506 | (2006.01) | |
| A61K 31/40 | (2006.01) | |
| A61K 45/06 | (2006.01) | |
| C07D 495/04 | (2006.01) | |
| A61K 31/7048 | (2006.01) | |
| A61K 31/7052 | (2006.01) | |
| C07D 207/14 | (2006.01) | |
| A61K 31/4025 | (2006.01) | |
| A61K 31/4155 | (2006.01) | |
| A61K 31/4178 | (2006.01) | |
| A61K 31/4192 | (2006.01) | |

(Continued)

(52) U.S. Cl.
CPC ............ *C07D 495/04* (2013.01); *A61K 31/40* (2013.01); *A61K 31/4025* (2013.01); *A61K 31/4155* (2013.01); *A61K 31/4178* (2013.01); *A61K 31/4192* (2013.01); *A61K 31/427* (2013.01); *A61K 31/435* (2013.01); *A61K 31/437* (2013.01); *A61K 31/4365* (2013.01); *A61K 31/4439* (2013.01); *A61K 31/4709* (2013.01); *A61K 31/506* (2013.01); *A61K 31/706* (2013.01); *A61K 31/7048* (2013.01); *A61K 31/7052* (2013.01); *A61K 45/06* (2013.01); *C07D 207/14* (2013.01); *C07D 401/10* (2013.01); *C07D 401/12* (2013.01); *C07D 403/06* (2013.01); *C07D 403/10* (2013.01); *C07D 403/12* (2013.01); *C07D 405/06* (2013.01); *C07D 405/12* (2013.01); *C07D 409/10* (2013.01); *C07D 409/12* (2013.01); *C07D 417/06* (2013.01); *C07D 417/10* (2013.01); *C07D 471/04* (2013.01); *Y02A 50/473* (2018.01); *Y02A 50/481* (2018.01)

(58) Field of Classification Search
CPC .. C07D 417/06; C07D 417/10; C07D 403/12; C07D 403/06; C07D 403/10; C07D 401/10; C07D 401/12; C07D 405/06; C07D 405/12; C07D 409/10; C07D 409/12; C07D 471/04; A61K 31/706; A61K 31/435; A61K 31/427; A61K 31/437; A61K 31/506; A61K 31/40; A61K 45/06
See application file for complete search history.

(56) References Cited

U.S. PATENT DOCUMENTS 4,235,871 A    11/1980 Papahadjopoulos et al.
4,501,728 A    2/1985  Geho et al.
(Continued)

OTHER PUBLICATIONS

RN-913503-61-4, 2006, registry database compound.*
(Continued)

*Primary Examiner* — Sun Jae Yoo
(74) *Attorney, Agent, or Firm* — Leydig, Voit & Mayer, Ltd.

(57) ABSTRACT

The present invention provides N-benzyl-3-sulfonamidopyrrolidines and related compounds, as well as pharmaceutical compositions and sanitizing compositions containing the same. The compounds and compositions are useful as antibiotic agents. Methods for making and using the compounds and compositions are also described.

20 Claims, 5 Drawing Sheets

Related U.S. Application Data

(60) Provisional application No. 62/055,508, filed on Sep. 25, 2014, provisional application No. 61/993,073, filed on May 14, 2014.

(51) Int. Cl.
*A61K 31/4365* (2006.01)
*A61K 31/4439* (2006.01)
*A61K 31/4709* (2006.01)

(56) References Cited

U.S. PATENT DOCUMENTS

| | | | |
|---|---|---|---|
| 4,837,028 | A | 6/1989 | Allen |
| 4,902,505 | A | 2/1990 | Pardridge et al. |
| 4,957,735 | A | 9/1990 | Huang |
| 5,004,697 | A | 4/1991 | Pardridge |
| 5,019,369 | A | 5/1991 | Presant et al. |
| 5,055,303 | A | 10/1991 | Riley, Jr. |
| 5,188,837 | A | 2/1993 | Domb |
| 5,254,342 | A | 10/1993 | Shen et al. |
| 5,268,164 | A | 12/1993 | Kozarich et al. |
| 5,271,961 | A | 12/1993 | Mathiowitz et al. |
| 5,413,797 | A | 5/1995 | Khan et al. |
| 5,506,206 | A | 4/1996 | Kozarich et al. |
| 5,514,670 | A | 5/1996 | Friedman et al. |
| 5,534,496 | A | 7/1996 | Lee et al. |
| 6,034,093 | A | 3/2000 | Ewing et al. |
| 2005/0119266 | A1 | 6/2005 | Shi et al. |
| 2006/0040986 | A1* | 2/2006 | Imagawa ............ A61K 31/444 514/318 |

OTHER PUBLICATIONS

RN-913508-64-2, 2006, registry database compound.*
RN-913514-24-6, 2006, registry database compound.*
Foss et al., 2011, Medicinal Chemistry Letters, 2, 289-292.*
Berge et al. (1977) "Pharmaceutical Salts," Journal of Pharmaceutical Science. 66:1-19.
Foss et al. (2011) "N-Benzyl-3-sulfonamidopyrrolidines Are a New Class of Bacterial DNA Gyrase Inhibitors," ACS Med. Chem. Lett. 2:289-292.
Ijntema et al. (1994) "Hydroxyapatite microcarriers for biocontrolled release of protein drugs," Int. J. Pharm. 112:215-224.
Johnston et al. (1992) "Sustained Delivery of Interleukin-2 from a Poloxamer 407 Gel Matrix Following Intraperitoneal Injection in Mice," Pharm. Res. 9:425-434.
Langer (1993) "Polymer-controlled drug delivery systems," Accounts Chem. Res. 26:537-542.
Mukherjee et al. (2007) "N-Benzyl-3-sulfonamidopyrrolidines as novel inhibitors of cell division in *E. coli*," Bioorg. Med. Chem. Lett. 17:6651-6655.
Fults et al. (1990) "Sustained-Release of Urease from a Poloxamer Gel Matrix," J. Parent. Sci. Tech. 44(2):58-65.
Pubchem Database [Online] (First Available Feb. 20, 2008) Substance Identification No. 47424487. Accessible on the Internet at URL: https://pubchem.ncbi.nlm.nih.gov/substance/47424487#section= Top. [Last Accessed Jun. 12, 2016].
Pubchem Database [Online] (Oct. 23, 2008) Assay Identification No. 1093. Version 1.2. Accessible on the Internet at URL: https:// pubchem.ncbi.nlm.nih.gov/bioassay/1093#section=Top. [Last Accessed Jun. 12, 2016].
International Search Report with Written Opinion corresponding to International Patent Application No. PCT/US2015/030638, dated Oct. 1, 2015.

* cited by examiner (Ia)

INHIBITORS OF BACTERIAL DNA GYRASE WITH EFFICACY AGAINST GRAM-NEGATIVE BACTERIA

The present application is a continuation of International Application No. PCT/US2015/030638, filed May 13, 2015, which claims priority to U.S. Provisional Pat. Appl. No. 61/993,073, filed May 14, 2014, and U.S. Provisional Pat. Appl. No. 62/055,508, filed Sep. 25, 2014, which applications are incorporated herein by reference in their entirety.

STATEMENT REGARDING FEDERALLY SPONSORED RESEARCH OR DEVELOPMENT

This invention was made with government support under AI062905 and OD008735 awarded by the National Institutes of Health. The government has certain rights in the invention.

BACKGROUND OF THE INVENTION

Antibiotic-resistant strains of bacteria present signifcant challenges for treating patients with infectious diseases and conditions. For example, some antibiotics, e.g., fluoroquinolones, are losing their effectiveness due to bacterial resistance, and some antibiotics are not effective against Gram-negative bacteria. These challenges have in some cases worsened since the pace of development for new antibiotics has been slow.

Research directed to the development of new antibiotics, to which bacteria are not resistant, is critically important. N-Benzyl-3-sulfonamidopyrrolidines have been identified as useful small molecule antibiotics and have been shown to inhibit bacterial growth, specifically the growth of *Escherichia coli* (See Mukherjee, S., et al., *Bioorg. Med. Chem. Lett.* 17, (2007) 6651-6655). Certain of these small molecule inhibitors have also been identified as inhibitors of the bacterial DNA gyrase enzyme (See Foss, M. H., et al., *ACS Med. Chem. Lett.*, 2011, 2, 289-292). The gyrase enzyme is required for bacterial survival, and thus compounds which inhibit this enzyme represent a new class of antibiotics.

There currently exists a need in the relevant field for new small molecules, such as benzyl-sulfonamidopyrrolidines, which are useful as antibiotics. In particular, there are needs for antibiotics which are useful for killing Gram-negative bacteria and bacteria which are resistant to antibiotics, e.g., vancomycin-resistant bacteria. There also exists a need for new methods for making these small molecules benzyl-sulfonamidopyrrolidines. The present invention meets these needs, as well as others, and provides, inter alia, methods of making and using new small molecule benzyl-sulfonamidopyrrolidines.

BRIEF SUMMARY OF THE INVENTION

The present application describes compounds that are useful, for example, as antibiotic inhibitors of bacterial DNA gyrase. The present application also describes methods of making and using these compounds.

In a first aspect, the present invention provides compounds having a structure selected from:

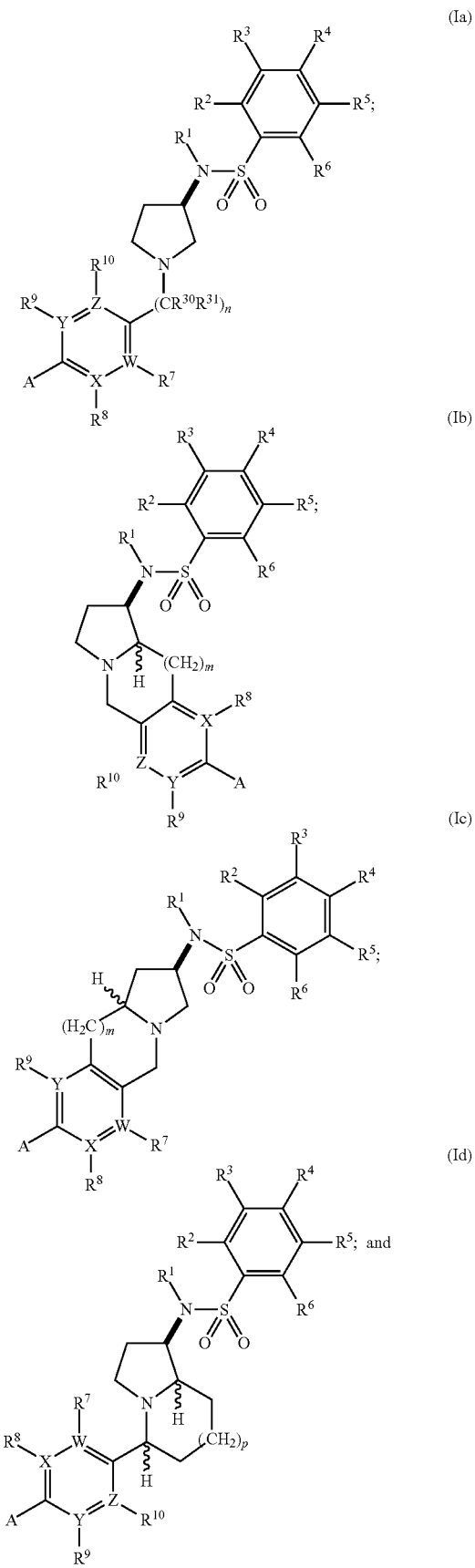

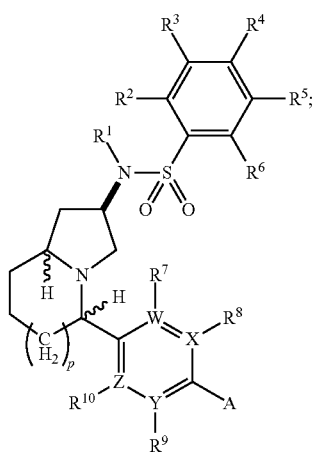

(Ie)

or a pharmaceutically acceptable salt thereof.

In these structures, A is $C_{1-12}$alkyl, $C_{6-10}$aryl, $C_{4-9}$heteroaryl, $C_{3-8}$cycloalkyl, $C_{3-8}$heterocycloalkyl, —$OC_{1-12}$alkyl, —$OC_{6-10}$aryl, —$OC_{4-9}$heteroaryl, —$OC_{3-8}$cycloalkyl, or —$OC_{3-8}$heterocycloalkyl. Ring vertices W, X, Y, and Z are in each instance independently C or N. $R^1$ is H or $C_{1-6}$alkyl. $R^2$, $R^3$, $R^4$, $R^5$, $R^6$, $R^7$, $R^8$, $R^9$, $R^{10}$, $R^{30}$, and $R^{31}$ are in each instance hydrogen, $C_{1-6}$alkyl, $C_{2-6}$alkenyl, $C_{2-6}$alkynyl, $C_{1-6}$alkoxy, acetyl, carboxy, $C_{3-8}$cycloalkyl, cyano, halo$C_{1-6}$alkyl, formyl, halogen, hydroxyl, halo$C_{1-6}$alkoxy, amino, $C_{1-6}$alkylamino, di$C_{1-6}$alkylamino, azido, mercapto, nitro, sulphamoyl, sulfo, or ureido; or optionally, two of $R^2$, $R^3$, $R^4$, $R^5$, $R^6$, $R^7$, $R^8$, $R^9$, $R^{10}$, $R^{30}$, and $R^{31}$ on adjacent ring vertices are combined to form a fused benzene ring, a fused 5- or 6-membered heteroaryl ring, a fused 5- or 6-membered cycloalkyl ring, or a fused 5- or 6-membered heterocycloalkyl ring. One of skill in the art will undertand that $R^7$ is absent when W is N. $R^8$ is absent when X is N. $R^9$ is absent when Y is N. $R^{10}$ is absent when Z is N. Subscript n is an integer selected from 1, 2, or 3. Subscript m is an integer selected from 0, 1, or 2. Subscript p is an integer selected from 0 or 1. In formula Ib, Ic, Id, and Ie, the wavy line "∿∿∿" indicates a R or S stereospecific bond. When A is phenyl, optionally substituted phenyl, methyl, or butyl, and $R^3$ or $R^5$ is halo, then $R^2$ and $R^6$ are other than methyl or chloro. When A is phenyl, optionally substituted phenyl, methyl, or butyl, and $R^4$ is iodo or ethynyl, then at least one of $R^2$, $R^3$, $R^5$, and $R^6$ is other than hydrogen.

Also described herein are prodrugs or quaternary ammonium salts of a compound having a structure selected from Ia, Ib, Ic, Id, or Ie.

In another aspect, compounds are provided having a structure selected from:

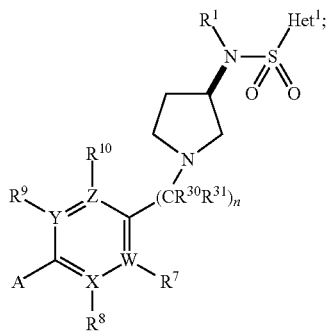

(Ia-h)

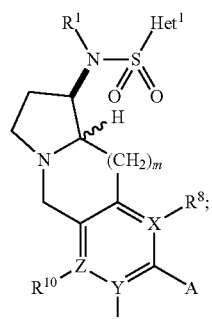

(Ib-h)

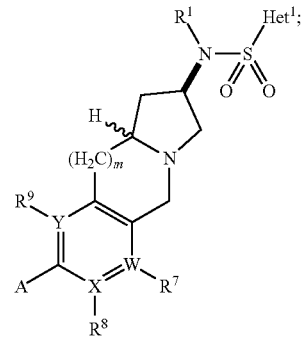

(Ic-h)

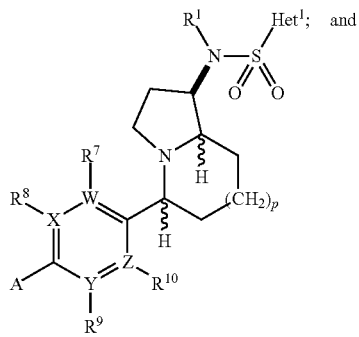

(Id-h); and

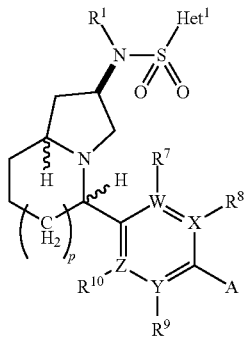

(Ie-h)

or a pharmaceutically acceptable salt thereof, wherein $Het^1$ is a 5- to 10-membered heteroaryl ring, optionally substituted with $R^2$, $R^3$, $R^4$, $R^5$ and $R^6$, wherein each of the variables or substituents has the meaning provided above with respect to formulae Ia, Ib, Ic, Id and Ie.

In yet another aspect, compounds are provided having a structure selected from:

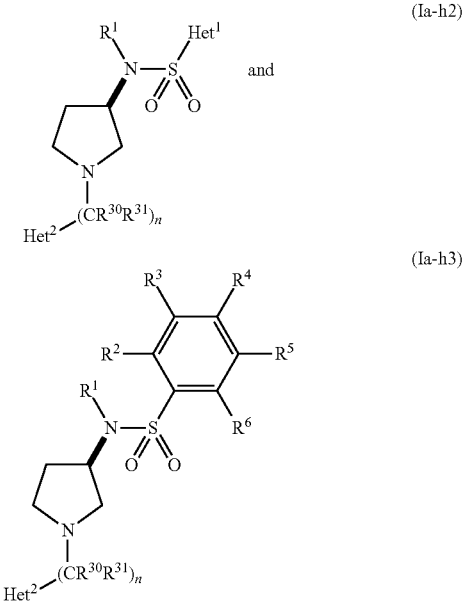

wherein Het² is a 5-membered heteroaryl group, optionally substituted with A, as defined above. For each of formula Ia-h2 and Ia-h3, the remaining variables or substituents have the meanings provided with respect to formulae Ia and Ia-h.

In another aspect, described herein are pharmaceutical compositions including a pharmaceutically acceptable excipient and a compound having a structure selected from Ia, Ib, Ic, Id, Ie, Ia-h, Ib-h, Ic-h, Id-h, or Ie-h, or a pharmaceutically acceptable salt thereof.

In yet another aspect, provided herein are methods of killing bacteria, wherein the method includes contacting the bacteria with a compound having a structure selected from Ia, Ib, Ic, Id, Ie, Ia-h, Ib-h, Ic-h, Id-h, or Ie-h, or a pharmaceutically acceptable salt thereof.

In still another aspect, provided herein are methods of inhibiting bacterial growth, wherein the method includes contacting the bacteria with a compound having a structure selected from Ia, Ib, Ic, Id, Ie, Ia-h, Ib-h, Ic-h, Id-h, or Ie-h, or a pharmaceutically acceptable salt thereof.

In another aspect, provided herein are methods of treating a disease in a subject in need thereof, wherein the method includes administering to the subject an effective amount of a compound having a structure selected from Ia, Ib, Ic, Id, Ie, Ia-h, Ib-h, Ic-h, Id-h, or Ie-h, or a pharmaceutically acceptable salt thereof, or a pharmaceutical composition thereof.

DETAILED DESCRIPTION OF THE INVENTION

I. General

Figure 1:
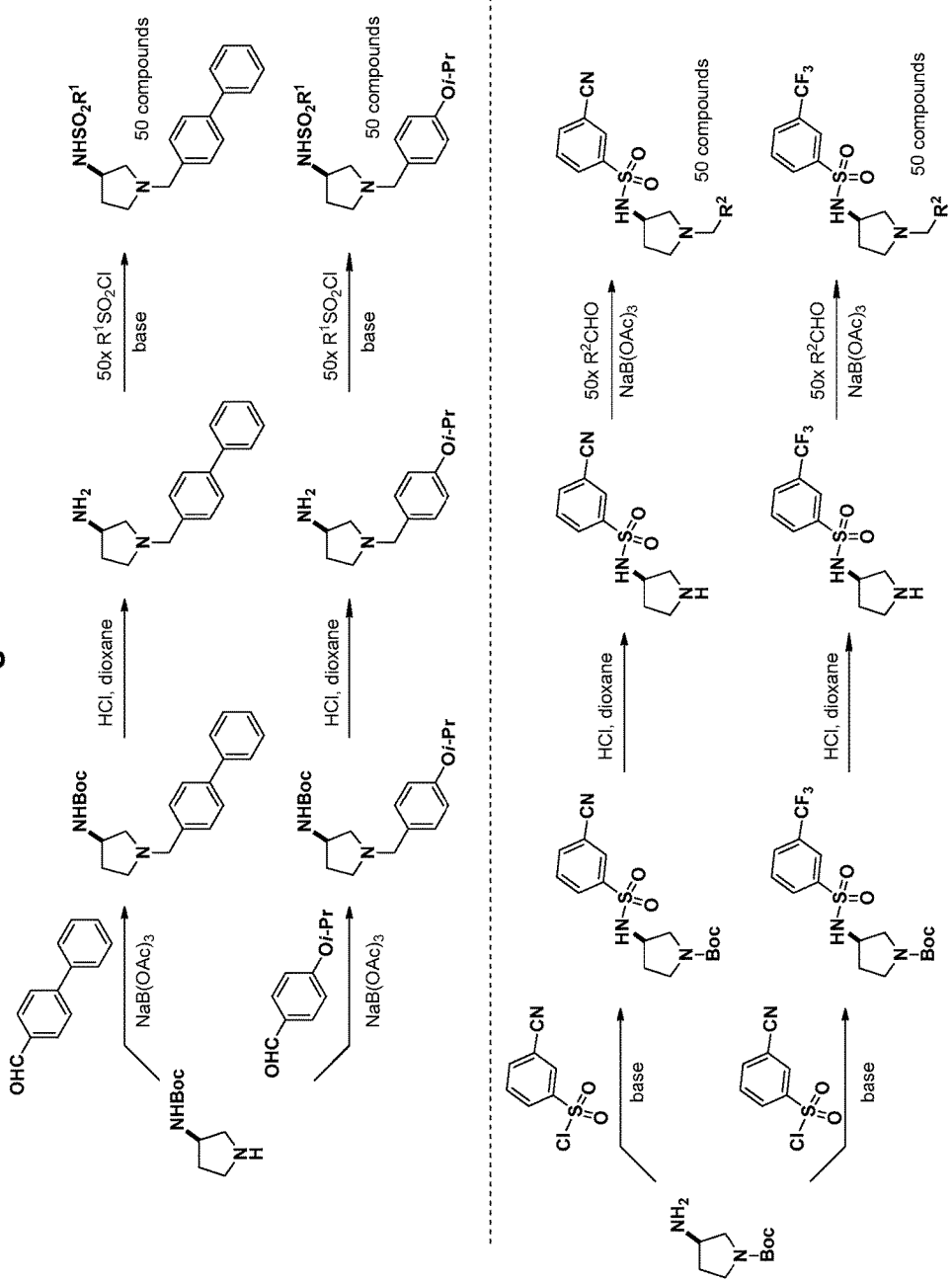
FIG. 1 illustrates representative synthetic routes to compounds provided herein.

This patent application describes novel compounds and compositions which are useful as antibiotic agents. Also described herein are methods of making and using these compounds and compositions. Compounds of the invention, including gyramide C2, are surprisingly active inhibitors of DNA gyrase as compared to known gyrase inhibitors ciprofloxacin and novobiocin.

II. Definitions

As used herein, the following terms have the meanings ascribed to them unless specified otherwise.

It is noted here that as used in this specification and the appended claims, the singular forms "a," "an," and "the" include plural reference unless the context clearly dictates otherwise. In addition, the terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, or neutral conditions.

The term "alkyl," by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-10}$cycloalkyl means three to ten carbons in the hydrocarbon ring) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycylic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

As used herein, the term "haloalkyl" refers to an alkyl group that is substituted with at least 1 halo substituent selected from the group consisting of F, Cl, Br, and I. Haloalkyl groups may include 2N+2 halo substituents, wherein N is the number of carbon atoms in the haloalkyl. For example, haloethyl which has N equal to 2 may include 1, 2, 3, 4, 5, or 6 halo substituents, e.g., fluoroethane, 1,1-difluoroethane, or perfluoroethane.

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The term "amino-C$_{1-4}$ alkyl" refers to an amino group bearing an C$_{1-6}$ alkyl group (e.g., methyl, ethyl, propyl, isopropyl, n-butyl, sec-butyl, isobutyl and tert-butyl) and which is attached to the remainder of the molecule through the C$_{1-6}$ alkyl group (a one to six carbon alkylene linking group). Examples of amino-C$_{1-6}$ alkyl groups include aminomethyl, aminoethyl, aminobutyl, aminohexyl, and the like.

The term "di-(C$_{1-4}$ alkyl)amino-C$_{1-4}$ alkyl" refers to an amino group bearing two C$_{1-4}$ alkyl groups that can be the same or different (e.g., methyl, ethyl, propyl, isopropyl, n-butyl, sec-butyl, isobutyl and tert-butyl) and which is attached to the remainder of the molecule through a C$_{1-4}$ alkyl group (a one to four carbon alkylene linking group). Examples of di-(C$_{1-4}$ alkyl)amino-C$_{1-4}$ alkyl groups include dimethylaminomethyl, 2-(ethyl(methyl)amino)ethyl, 3-(dimethylamino)butyl, and the like.

As used herein, the term "mercapto" is synonymous with "thiol," and is used in the conventional sense, and refers to an alkyl group substituent that is attached to the remainder of the molecule via a sulfur atom (s).

As used herein, the term "haloalkoxy" refers to an alkoxy group wherein any of the hydrogens are replaced with a halogen. In some examples, the halogens in a given haloalkoxy are of the same type, e.g., all halogens in the haloalkoxy are the same halo. However, in some other examples, the halogens in a given haloalkoxy are of different types, e.g., the halogens in the haloalkoxy are individually selected from F, Cl, Br, I, or combinations thereof. For example, haloethoxy includes, but is not limited to fluoroethoxy, 1,1-difluoroethoxy, perfluoroethane, and 1,1-dibromo-2,2-difluoroethane. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

As used herein, the term "acetyl" refers to a substituent having the general formula —C(O)CH$_3$. In this paragraph, C(O) refers to a carbon atom that is double bonded to O, e.g., C=O.

The term "aryl" means, unless otherwise stated, a polyunsaturated, typically aromatic, hydrocarbon group which can be a single ring or multiple rings (up to three rings) which are fused together or linked, having the number of carbon atoms designated (i.e., C$_{6-10}$ means six to ten carbons). The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. In this paragraph, heteroatom is an atom selected from the group consisting of N, O, or S. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described herein. Pyridyl represents 2, 3, or 4 pyridyl. Thienyl represents 2 or 3 thienyl. Quinolinyl represents preferably 2, 3, or 4 quinolinyl. Isoquinolinyl represents preferably 1, 3, or 4 isoquinolinyl. Benzopyranyl, benzothiopyranyl represents 3 benzopyranyl or 3 benzothiopyranyl, respectively. Thiazolyl represents preferably 2 or 4 thiazolyl. Triazolyl includes 1, 2, or 5 (1,2,4 triazolyl).

As used herein, the terms "halo" or "halogen," by themselves or as part of another substituent, mean, unless otherwise stated, a fluorine, chlorine, bromine, or iodine atom.

As used herein, a wavy line, "∼", that intersects a single, double or triple bond in any chemical structure depicted herein, represents the point attachment of the single, double, or triple bond to the remainder of the molecule.

As used herein, the term "amino" refers to a substituent having the general formula —NR$^a$R$^b$. R$^a$ and R$^b$ are independently selected from H, alkyl, alkenyl, alkynyl, cycloalkyl, and alkyl substituted by cycloalkyl or heterocycloalkyl. Examples include, but are not limited to, —NH$_2$, —NHCH$_3$, —NHCH$_2$CH$_3$, and —N(CH$_3$)$_2$.

As used herein, the term "azido" refers to a substituent having the formula —N$_3$.

As used herein, the term "sulphamoyl" refers to a substituent having the formula —SO$_2$NH$_2$.

As used herein, the term "sulfo" refers to a substituent having the formula —SO$_2$R wherein R is a group such as, but not limited to, halogen, hydroxyl, alkyl, amino, or aminoalkyl. Examples include, but are not limited to, —SO$_2$(OH).

As used herein, the term "ureido" refers to a chemical group having the structure —NH—C(O)—NH$_2$.

Each of the above terms (e.g., "alkyl," "heteroalkyl," "aryl" and "heteroaryl"), when indicated as "substituted" or "optionally substituted," are meant to include both substituted and unsubstituted forms of the indicated radical.

The above terms (e.g., "alkyl," "aryl," and "heteroaryl"), in some embodiments, will include both substituted and unsubstituted forms of the indicated radical.

Substituents for the alkyl radicals (including those groups often referred to as alkylene, alkenyl, alkynyl and cycloalkyl) can be a variety of groups selected from: halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ mercapto groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

As used herein, the term "heteroatom" includes oxygen (O), nitrogen (N), or sulfur (S).

The term "pharmaceutically acceptable salt" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine (i.e., 2-amino-2-hydroxymethyl-propane-1,3-diol) and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

As used herein, the phrase "pharmaceutically-acceptable" or "therapeutically-acceptable" refers to a substance which does not interfere with the effectiveness or the biological activity of the active ingredients and which is not toxic to the hosts in the amounts used, and which hosts may be either humans or animals to which it is to be administered.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "antibiotic" refers to a compound or composition that has antibacterial, antimicrobial, or bacteriostatic properties. Examples include, but are not limited to, penicillin.

As used herein, the terms "erythromycin class antibiotic" and "macrolide antibiotic" refer to an antibiotic having structural similarly to erythromycin. Examples include, but are not limited to, ansamycin; azithromycin (Zithromax/Zitromax/Sumamed); carbomycin; cethromycin; clarithromycin (Biaxin; Dirithromycin/Dynabac; Mitemcinal); oleandomycin; roxithromycin (Rulid/Surlid/Roxid); spiramycin; telithromycin; and tylocine.

As used herein, the term "gyrase inhibitor" refers to compound that inhibits the activity of DNA gyrase. Examples include, but are not limited to, those compounds found in Foss, M. H., et al., *ACS Med. Chem. Lett.*, 2011, 2, 289-292 as well as aminocoumarins, e.g., novobiocin; and quinolones, e.g., nalidixic acid and ciprofloxacin.

As used herein, the term "β-lactam" refers to compounds that include the β-lactam structure, e.g.:

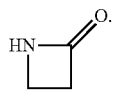

Examples of β-lactams include, but are not limited to, penicillins, cephalosporins, carbapenems, and monobactams.

As used herein, the phrase "killing bacteria" refers to a method, action, process, or physical reaction or interaction which results in the cessation of life for a given bacteria.

As used herein, the term "fluoroquinolone antibiotic" refers to an antibiotic that includes a fluoroquinolone group. Examples include, but are not limited to, cinoxacin (Cinobac); nalidixic acid (NegGram, Wintomylon); oxolinic acid (Uroxin); piromidic acid (Panacid); pipemidic acid (Dolcol); rosoxacin (Eradacil); ciprofloxacin (Alcipro, Ciprobay, Cipro, Ciproxin); enoxacin (Enroxil, Penetrex); fleroxacin (Megalone, Roquinol); lomefloxacin (Maxaquin); nadifloxacin (Acuatim, Nadoxin, Nadixa); norfloxacin (Lexinor, Noroxin, Quinabic, Janacin); ofloxacin (Floxin, Oxaldin, Tarivid); pefloxacin (Peflacine); rufloxacin (Uroflox); balofloxacin (Baloxin); grepafloxacin (Raxar); levofloxacin (Cravit, Levaquin); pazufloxacin (Pasil, Pazucross); sparfloxacin (Zagam); temafloxacin (Omniflox); tosufloxacin (Ozex, Tosacin); clinafloxacin; gatifloxacin (Zigat, Tequin) (Zymar-opth.) (Tequin removed from clinical use); gemifloxacin (Factive); moxifloxacin (Avelox,Vigamox); sitafloxacin (Gracevit); trovafloxacin (Trovan); prulifloxacin (Quisnon); delafloxacin; JNJ-Q2; nemonoxacin; danofloxacin (Advocin, Advocid); difloxacin (Dicural, Vetequinon); enrofloxacin (Baytril); ibafloxacin (Ibaflin); marbofloxacin (Marbocyl, Zenequin); orbifloxacin (Orbax, Victas); and sarafloxacin (Floxasol, Saraflox, Sarafin).

As used herein, the term "inhibiting bacterial growth" refers to inhibiting, retarding or slowing the rate of bacterial growth. Inhibition of bacterial growth includes, but is not limited to, bacteriostatic activity as well as bactericidal activity.

The terms "individual," "subject," and "patient" typically refer to humans, but also include other animals such as other primates, rodents, canines, felines, equines, ovines, porcines, and the like.

As used herein, "treat," "treating," and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters including but not limited to the results of a physical examination and laboratory analysis. "Treating," includes, but is not limited to, methods and manipulations to produce beneficial changes in a recipient's health status, e.g., a patient's infection status. The changes can be either subjective or objective and can relate to features such as symptoms or signs of the disease or condition being treated. For example, if the patient notes decreased pain, then successful treatment of pain has occurred. For example, if a decrease in the amount of swelling has occurred, then a beneficial treatment of inflammation has occurred. Similarly, if the clinician notes objective changes, such as a reduction in the signs or symptoms of a bacterial infection, the treatment as an antibiotic has been beneficial. Preventing the deterioration of a recipient's status is also included by the term. Treating, as used herein, also includes administering a compound or composition described herein to a patient having a bacterial infection.

As used herein, the terms "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the term "effective amount" refers to a dosage sufficient to produce a desired result with respect to the indicated disorder or condition. The desired result may comprise a subjective or objective improvement in the recipient of the dosage. With respect to treating a bacterial infection, the improvement may be decreased sign or symptom of pain, symptom of the bacteria, or detectable presence of the bacteria. For example, an effective amount of a compound or composition described herein includes an amount sufficient to alleviate the signs, symptoms, or causes of a bacterial infection. Also for example, an effective amount of a compound or composition described herein includes an amount sufficient to causes a substantial improvement in a subject having an infection or disease associated with an infection when administered to a subject.

The amount will vary with the type of disease or condition being treated, the stage of advancement of the disease or condition, and the type and concentration of composition administered to the subject.

As used herein, the term "administering" refers to activities associated with providing a patient an amount of an agent, e.g., a compound described herein. Administering includes providing unit dosages of compositions set forth herein to a patient in need thereof. Administering includes providing effective amounts of agents, e.g., compounds or compositions set forth herein, for specified period of time, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or in a specified sequence, e.g., administration of a compound set forth herein followed by the administration of a second antibiotic.

Compounds of the invention having formula Ia, Ib, Ic, Id, or Ie can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more σ bonds. Rotamers are conformers that differ by rotation about only a single σ bond.

III. Compounds and Compositions

In a first aspect, the present invention provides compounds having a structure selected from:

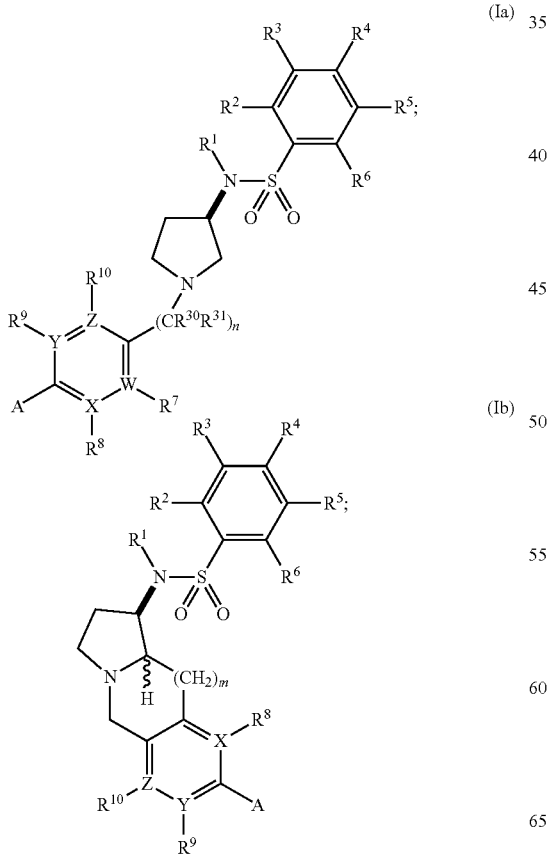

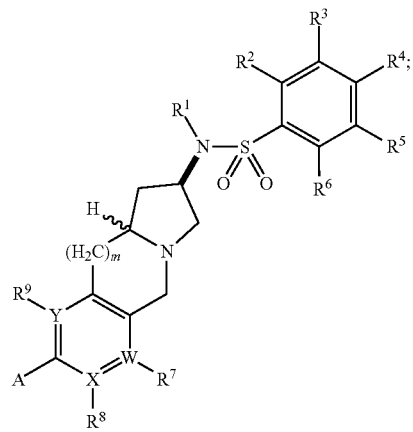

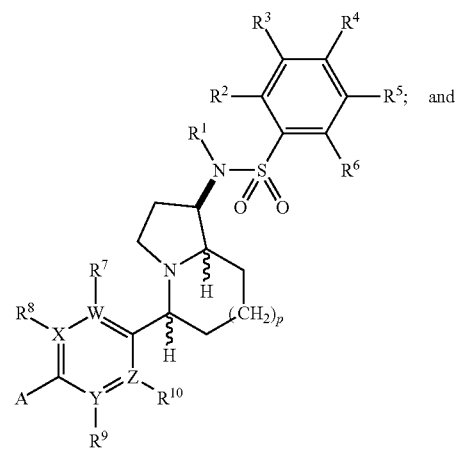

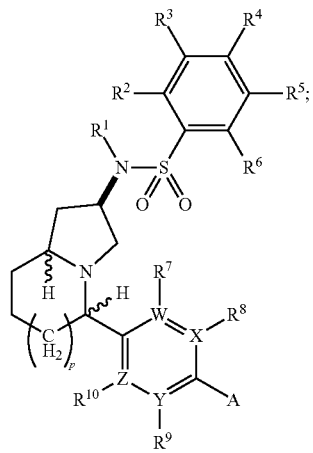

or a pharmaceutically acceptable salt thereof.

In these structures, A is $C_{1-12}$alkyl, $C_{6-10}$aryl, $C_{4-9}$heteroaryl, $C_{3-8}$cycloalkyl, $C_{3-8}$heterocycloalkyl, —$OC_{1-12}$alkyl, —$OC_{6-10}$aryl, —$OC_{4-9}$heteroaryl, —$OC_{3-8}$cycloalkyl, or —$OC_{3-8}$heterocycloalkyl. Ring vertices W, X, Y, and Z are in each instance independently C or N. $R^1$ is H or $C_{1-6}$alkyl. $R^2$, $R^3$, $R^4$, $R^5$, $R^6$, $R^7$, $R^8$, $R^9$, $R^{10}$, $R^{30}$, and $R^{31}$ are in each instance hydrogen, $C_{1-6}$alkyl, $C_{2-6}$alkenyl, $C_{2-6}$alkynyl, $C_{1-6}$alkoxy, acetyl, carboxy, $C_{3-8}$cycloalkyl, cyano, halo$C_{1-6}$alkyl, formyl, halogen, hydroxyl, halo$C_{1-6}$alkoxy, amino, $C_{1-6}$alkylamino, di$C_{1-6}$alkylamino, azido, mercapto, nitro, sulphamoyl, sulfo, or ureido; or optionally, two of $R^2$, $R^3$, $R^4$, $R^5$, $R^6$, $R^7$, $R^8$, $R^9$, $R^{10}$, $R^{30}$, and $R^{31}$ on adjacent ring vertices are combined to form a fused benzene ring, a fused 5- or 6-membered heteroaryl ring, a fused 5- or 6-membered cycloalkyl ring, or a fused 5- or 6-membered heterocycloalkyl ring. One of skill in the art will undertand that $R^7$ is absent when W is N. $R^8$ is absent when X is N. $R^9$ is absent when Y is N. $R^{10}$ is absent when Z is N. Subscript n is an integer selected from 1, 2, or 3. Subscript m is an integer selected from 0, 1, or 2. Subscript p is an integer selected from 0 or 1. In formula Ib, Ic, Id, and Ie, each wavy line indicates a R or S stereospecific bond. When A is phenyl, optionally substituted phenyl, methyl, or butyl, and $R^3$ or $R^5$ is halo, then $R^2$ and $R^6$ are other than methyl or chloro. When A is phenyl, optionally substituted phenyl, methyl, or butyl, and $R^4$ is iodo or ethynyl, then at least one of $R^2$, $R^3$, $R^5$, and $R^6$ is other than hydrogen.

In some embodiments, the invention provides compounds according to Formula (Ia); Formula (Ib); Formula (Ic); Formula (Id); or Formula (Ie) wherein A is $C_{1-12}$alkyl, $C_{6-10}$aryl, $C_{4-9}$heteroaryl, $C_{3-8}$cycloalkyl, $C_{3-8}$heterocycloalkyl, —$OC_{1-12}$alkyl, —$OC_{6-10}$aryl, —$OC_{4-9}$heteroaryl, —$OC_{3-8}$cycloalkyl, or —$OC_{3-8}$heterocycloalkyl. Ring vertices W, X, Y, and Z are in each instance independently C or N. $R^1$ is H or $C_{1-6}$alkyl. $R^2$, $R^3$, $R^4$, $R^5$, $R^6$, $R^7$, $R^8$, $R^9$, $R^{10}$, $R^{30}$, and $R^{31}$ are in each instance hydrogen, $C_{1-6}$alkyl, $C_{2-6}$alkenyl, $C_{2-6}$alkynyl, $C_{1-6}$alkoxy, acetyl, carboxy, $C_{3-8}$cycloalkyl, cyano, halo$C_{1-6}$alkyl, formyl, halogen, hydroxyl, halo$C_{1-6}$alkoxy, amino, $C_{1-6}$alkylamino, di$C_{1-6}$alkylamino, azido, mercapto, nitro, sulphamoyl, sulfo, or ureido; or optionally, two of $R^2$, $R^3$, $R^4$, $R^5$, $R^6$, $R^7$, $R^8$, $R^9$, $R^{10}$, $R^{30}$, and $R^{31}$ on adjacent ring vertices are combined to form a fused benzene ring, a fused 5- or 6-membered heteroaryl ring, a fused 5- or 6-membered cycloalkyl ring, or a fused 5- or 6-membered heterocycloalkyl ring. One of skill in the art will undertand that $R^7$ is absent when W is N. $R^8$ is absent when X is N. $R^9$ is absent when Y is N. $R^{10}$ is absent when Z is N. Subscript n is an integer selected from 1, 2, or 3. Subscript m is an integer selected from 0, 1, or 2. Subscript p is an integer selected from 0 or 1. In formula Ib, Ic, Id, and Ie, the wavy line "⁓" indicates a R or S stereospecific bond. If A is phenyl, optionally substituted phenyl, methyl, or butyl, then $R^2$ and $R^6$ are other than methyl, $R^3$ and $R^5$ are other than fluoro or chloro, and $R^4$ is other than iodo or ethynyl.

In another aspect, compounds are provided having a structure selected from:

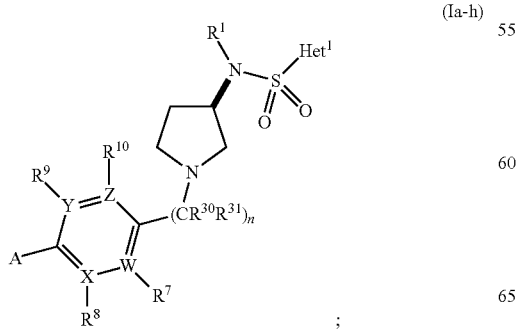

(Ia-h)

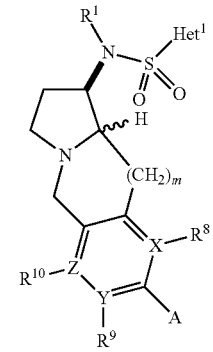

(Ib-h)

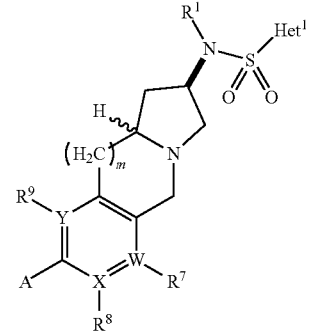

(Ic-h)

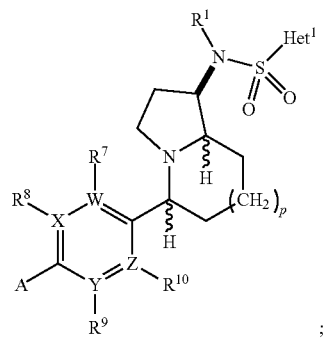

(Id-h)

; and

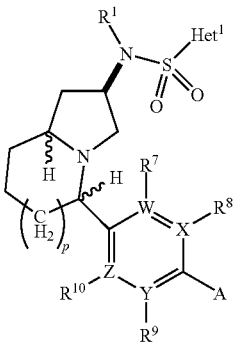

(Ie-h)

or a pharmaceutically acceptable salt thereof, wherein $Het^1$ is a 5- to 10-membered heteroaryl ring, optionally substituted with $R^2$, $R^3$, $R^4$, $R^5$ and $R^6$, wherein each of the remaining variables or substituents has the meaning provided above with respect to formulae Ia, Ib, Ic, Id and Ie.

Figure 2:
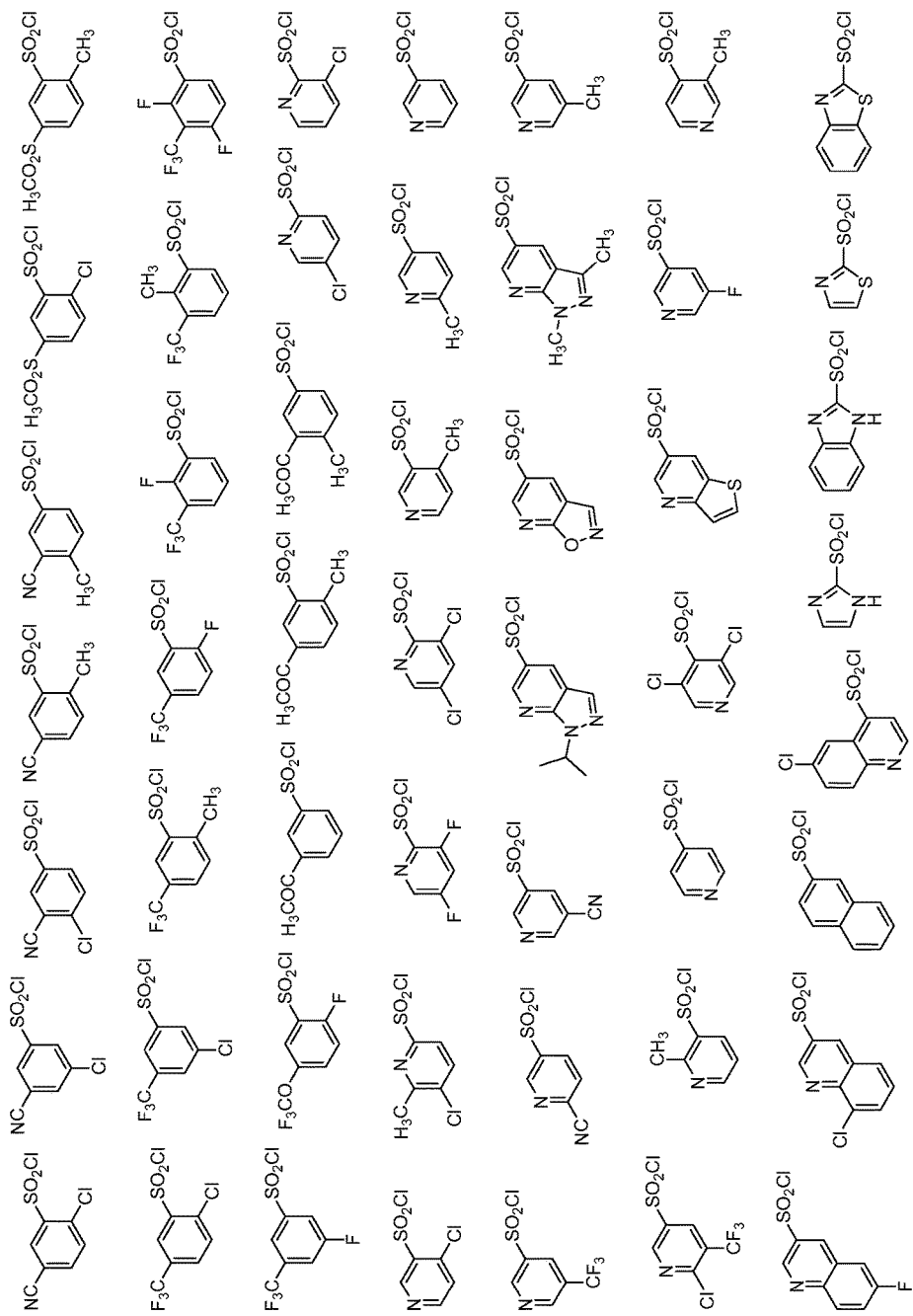
FIG. 2 illustrates some of the sulfonyl chlorides useful in preparing compounds provided herein, utilizing the processes outlined in FIG. 1.
Figure 3:
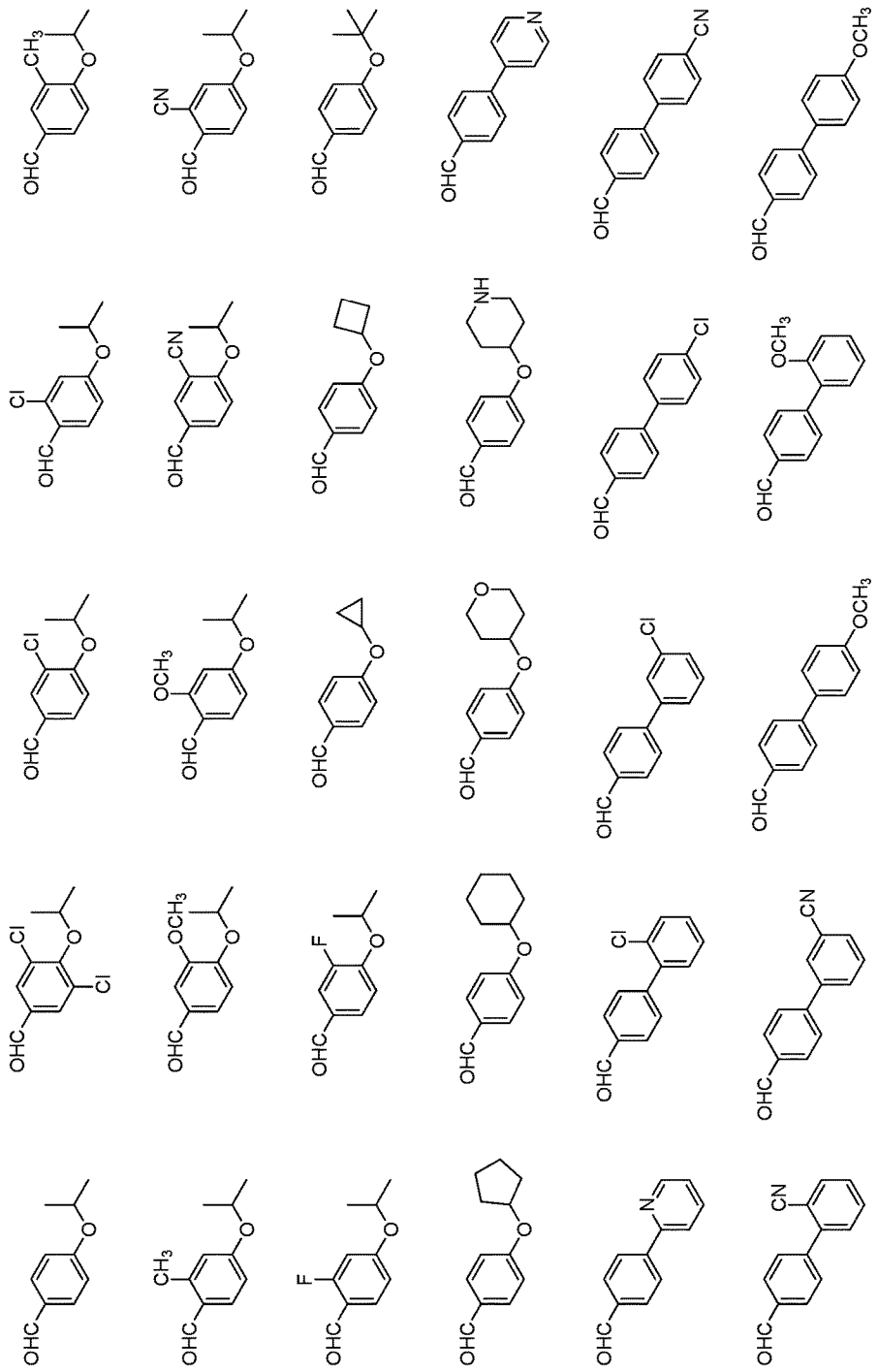
FIG. 3 illustrates some of the aromatic aldehyde components useful in preparing compounds provided herein, via the processes outlined in FIG. 1.
Figure 4:
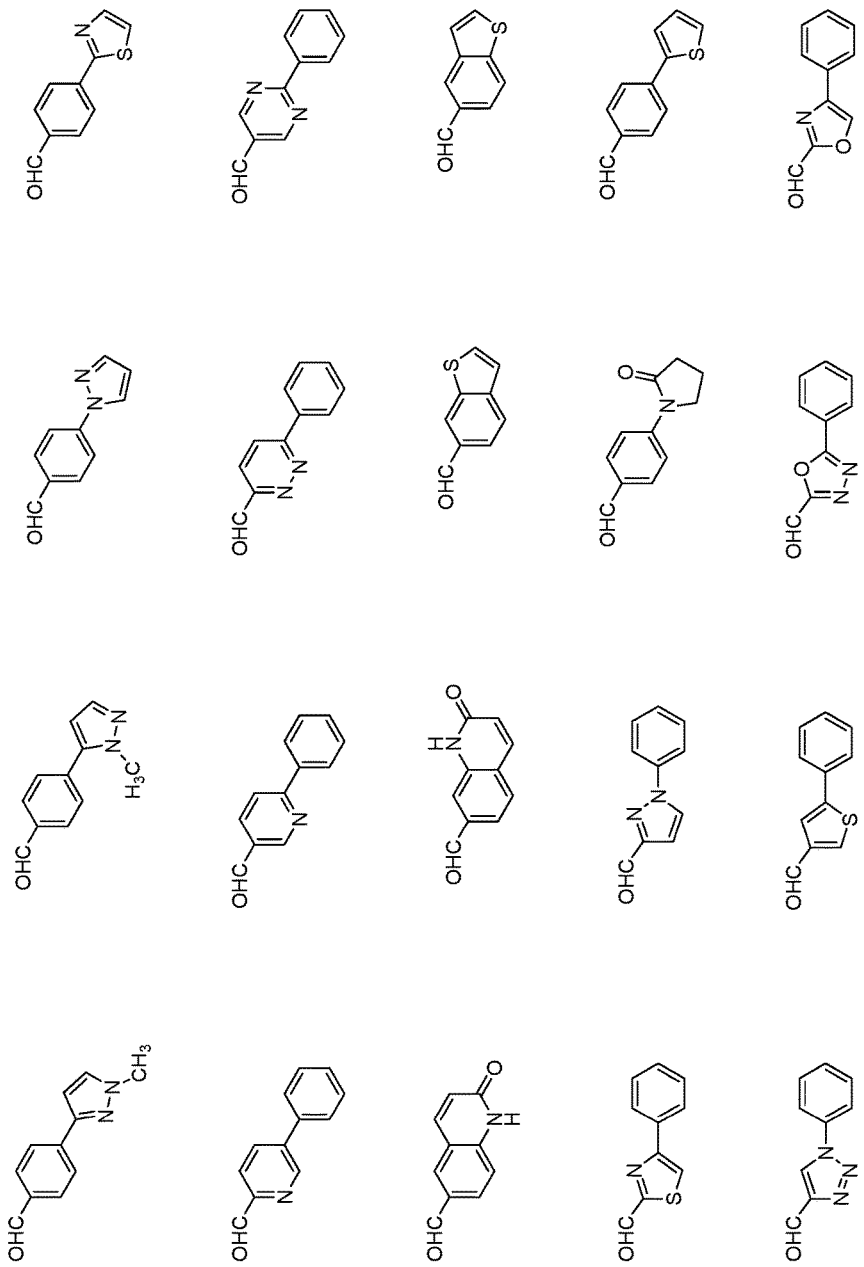
FIG. 4 illustrates some additional aromatic and heteroaromatic aldehyde components useful in preparing compounds provided herein, via the processes outlined in FIG. 1.
Figure 5:
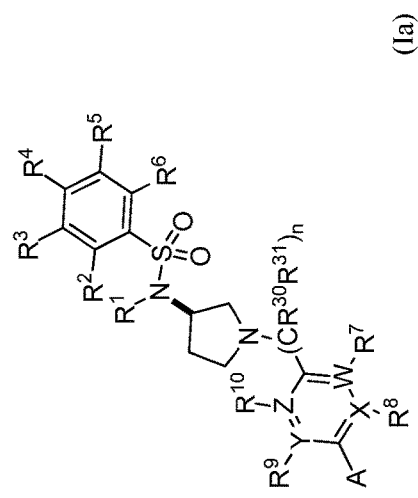
FIG. 5 shows the structure of certain compounds of the invention.

In some embodiments of formulae Ia-h, Ib-h, Ic-h, Id-h and Ie-h, $Het^1$ is selected from the group consisting of 2-pyridyl, 3-pyridyl, 4-pyridyl, 2-quinolinyl, 3-quinolinyl, 4-quinolinyl, 2-thiazolyl, 4-thiazolyl, 5-thiazolyl, 2-benzothiazolyl, 2-imidazolyl, 2-benzimidazolyl, and substituted forms thereof. In still other embodiments, the Het[1] portion is the optionally substituted heteroaryl portion provided (as sulfonyl chlorides) in FIG. 2.

In another aspect, compounds are provided having a structure selected from:

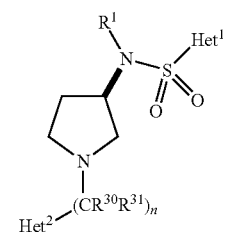
(Ia-h2)

and

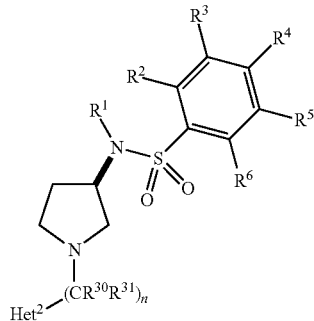
(Ia-h3)

wherein Het[2] is a 5-membered heteroaryl group, optionally substituted with A, as defined above. For each of formula Ia-h2 and Ia-h3, the remaining variables or substituents have the meanings provided with respect to formulae Ia and Ia-h. In some embodiments, Het[2] is selected from pyrazolyl, thiazolyl, triazolyl, oxazolyl, oxadiazolyl, thienyl, furanyl, pyrrolyl, and thiadiazolyl, each of which is optionally substituted with A. In some embodiments, A is an optionally substituted phenyl group.

In certain embodiments described above, the compound has the following structure:

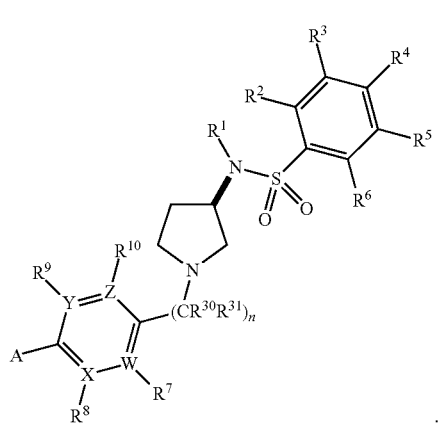
(Ia)

In certain other embodiments, the compound has the following structure:

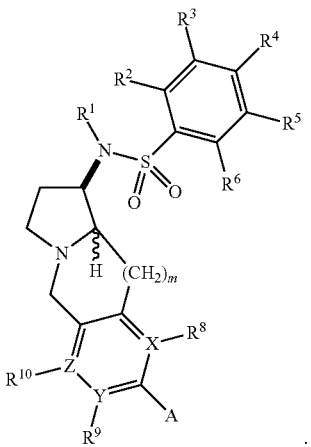
(Ib)

In other embodiments, the compound has the following structure:

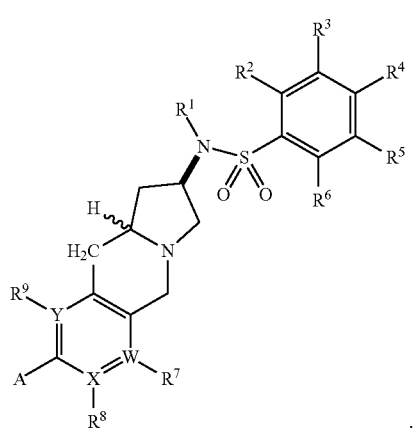
(Ic)

In certain embodiments described above, the compound has the following structure:

(Id)

In other embodiments, the compound has the following structure:

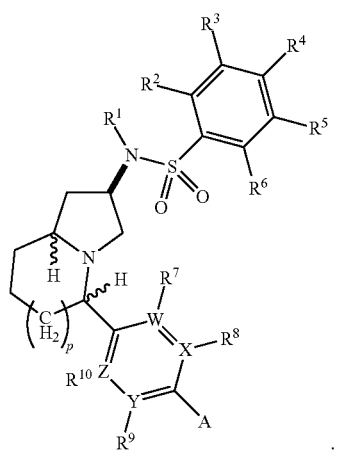

(Ie)

In some of the above embodiments, the present application sets forth a compound having a structure selected from Ia, Ib, Ic, Id, or Ie, wherein A has a structure selected from:

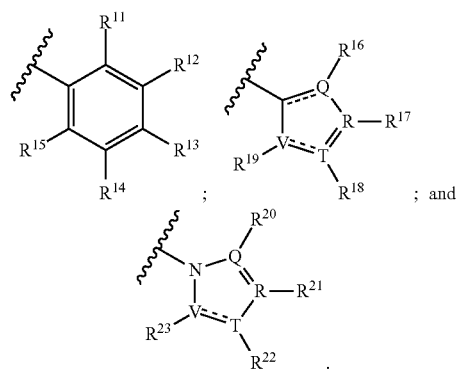

; and

In these structures, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are in each instance independently selected from hydrogen, $C_{1-6}$alkyl, $C_{2-6}$alkenyl, $C_{2-6}$alkynyl, $C_{1-6}$alkoxy, acetyl, carboxy, $C_{3-8}$cycloalkyl, cyano, halo$C_{1-6}$alkyl, formyl, halogen, hydroxyl, halo$C_{1-6}$alkoxy, amino, amino$C_{1-6}$alkyl, di$C_{1-6}$alkylamino, azido, mercapto, nitro, sulphamoyl, sulfo, or ureido. Q, R, T, and V are each independently selected from C, N, O, or S. $R^{16}$ and $R^{20}$ are absent when Q is N, O, or S. $R^{17}$ and $R^{21}$ are absent when R is N, O, or S. $R^{18}$ and $R^{22}$ are absent when T is N, O, or S. $R^{19}$ and $R^{23}$ are absent when V is N, O, or S. Each dashed line is independently absent, indicating a single bond, or present, indicating a double bond; and each wavy line represents the point of attachment to the ring to which A is attached.

In some embodiments, A is selected from phenyl, substituted phenyl, thiophenyl, and pyrazolyl. In some embodiments, A is selected from phenyl, 4-chlorophenyl, 3-chlorophenyl, thiophen-2-yl, and 1H-pyrazol-1-yl.

In some embodiments, A is selected from —OC$_{1-12}$alkyl, —OC$_{6-10}$aryl, —OC$_{4-9}$heteroaryl, —OC$_{3-8}$cycloalkyl, and —OC$_{3-8}$heterocycloalkyl. In some embodiments, A is selected from isobutyloxy, cyclopropyloxy, cyclobutyloxy, and cyclopentyloxy.

In certain of the above embodiments, both $R^{30}$ and $R^{31}$ are hydrogen.

In some of the above embodiments. A has the following structure:

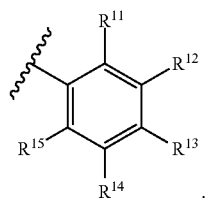

In some other of the above embodiments, A has the following structure:

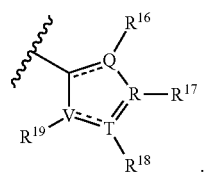

In yet other of the above embodiments, A has the following structure:

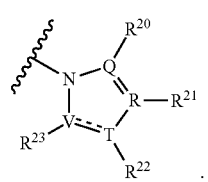

In other embodiments, the invention provides compounds having the following structure:

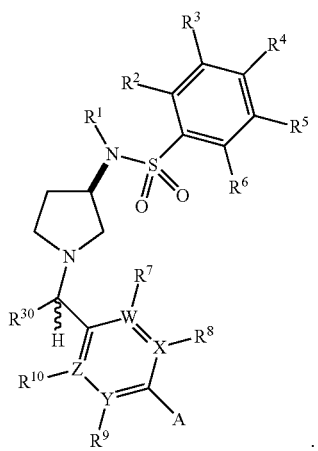

(II)

In some of the embodiments of the compound having structure II, the compound has a structure is selected from:

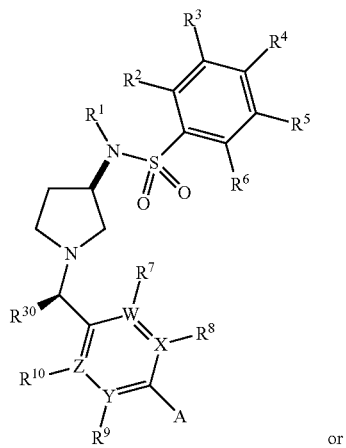
or
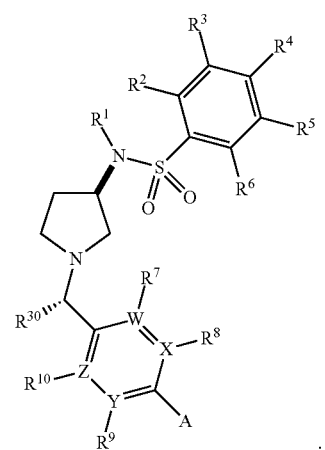
In certain embodiments, the compound has the following structure:
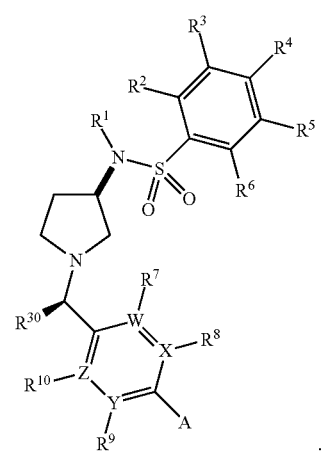
In certain embodiments, the compound has the following structure:
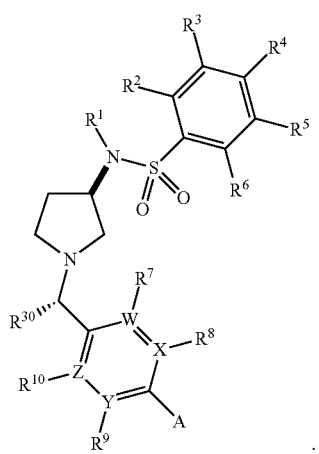
In some of these embodiments, $R^{30}$ is alkyl.
In some other embodiments of the compounds described above, the invention provides compounds having a structure selected from:
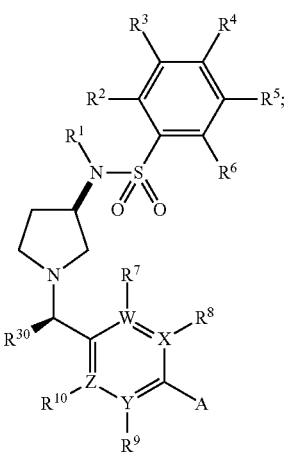
(IIIa)
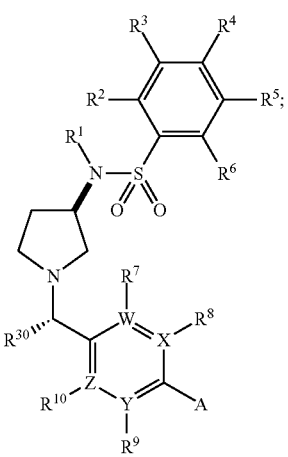
(IIIb)

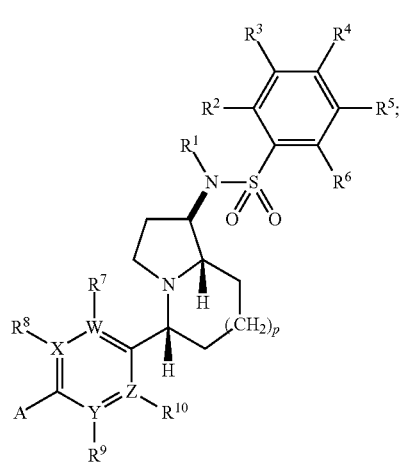
(IIIc)
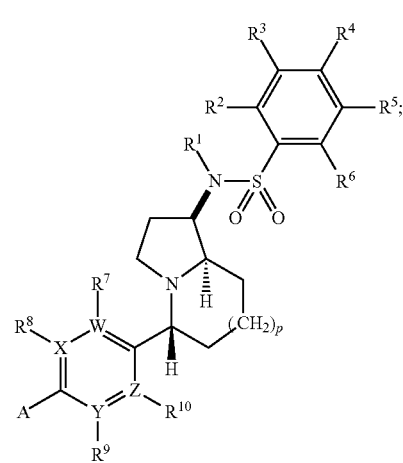
(IIIf)
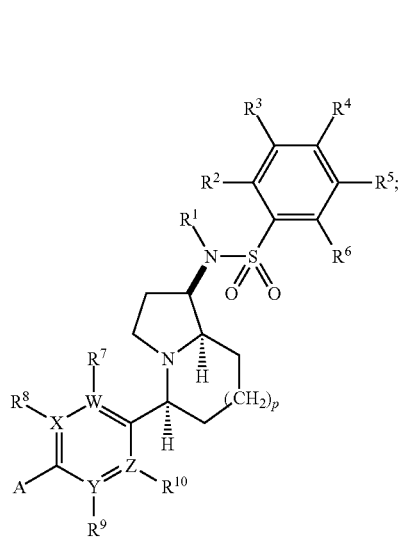
(IIId)
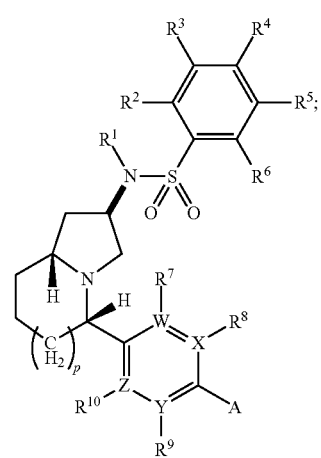
(IIIg)
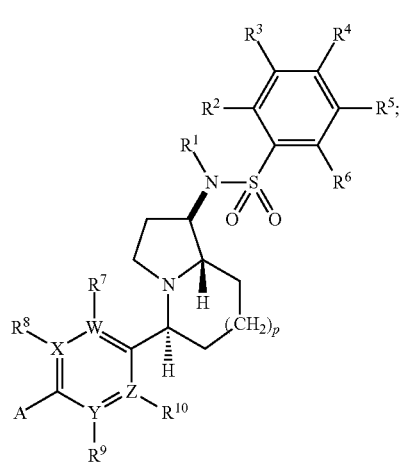
(IIIe)
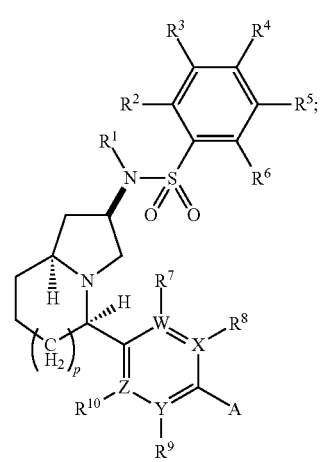
(IIIh)

-continued
(IIIi)
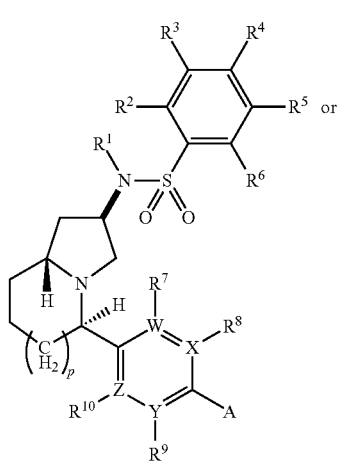
(IIIj)
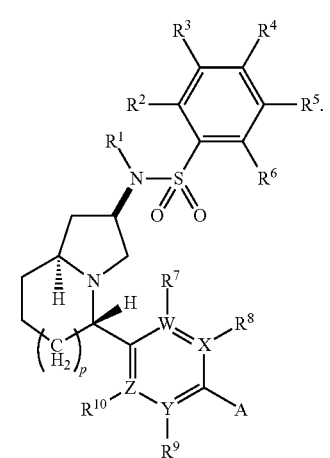
In some of the embodiments of the compounds having a structure selected from IIIa, IIIb, IIIc, IIId, IIIe, IIIf, IIIg, IIIh, IIIi, or IIIj, the compound has a structure selected from:
(IVa)
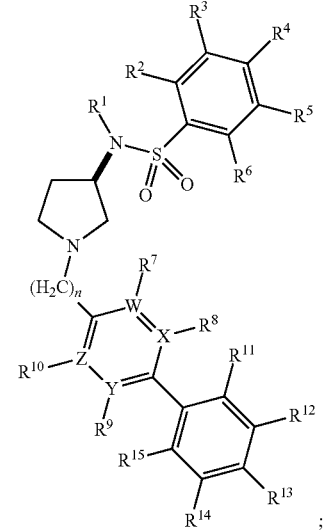
;
-continued
(IVb)
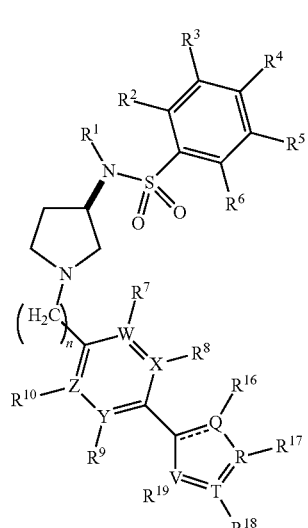
;
(IVc)
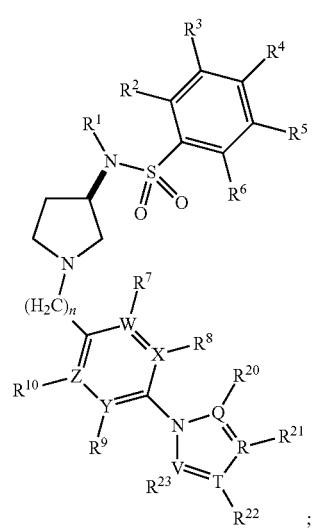
;
(IVd)
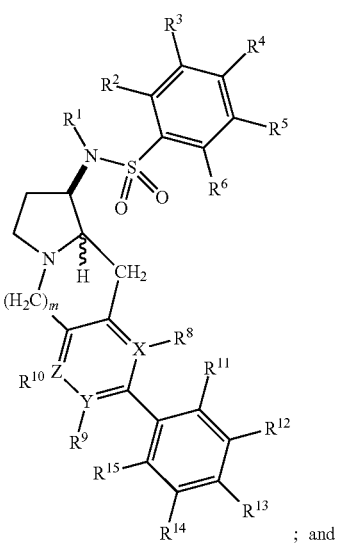
; and

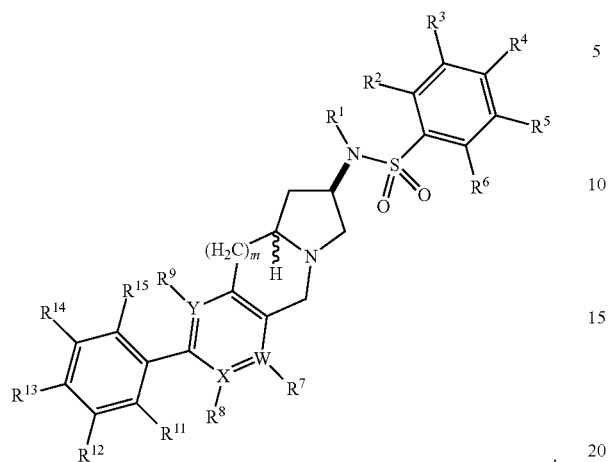
(IVe)
In some other embodiments of the compounds described above, the compounds has a structure selected from:
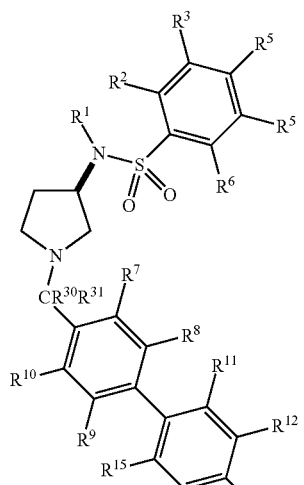
(Va)
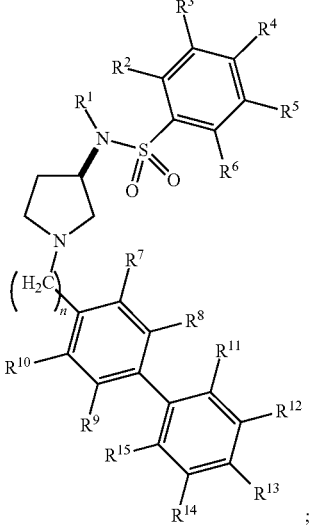
(Vb)
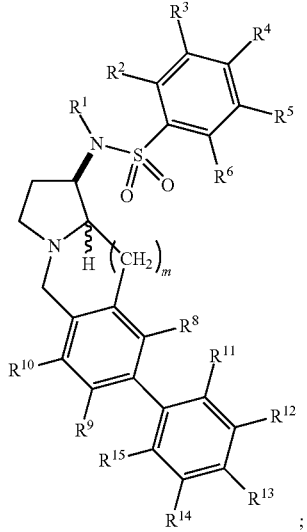
(Vc)
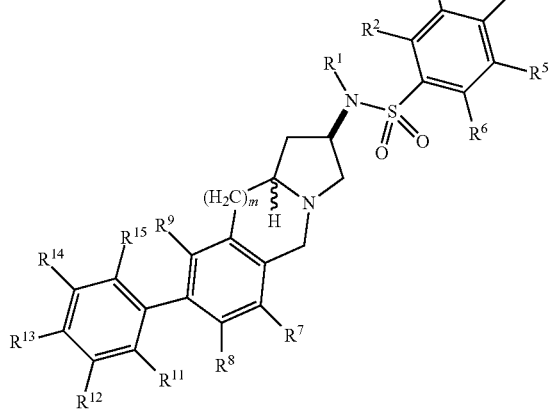
(Vd)
In some of the embodiments described above, the compound has the following structure:
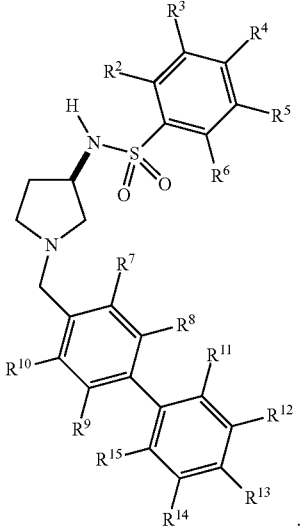
(VI)

In certain embodiments, $R^3$ is cyano and at least one of $R^7$, $R^8$, $R^9$, $R^{10}$, $R^{11}$, $R^{12}$, $R^{13}$, $R^{14}$ and $R^{15}$ is other than hydrogen.

In some embodiments, each $R^2$, $R^3$, $R^4$, $R^5$, and $R^6$ is independently selected from hydrogen, $C_{1-6}$alkyl, $C_{1-6}$alkoxy, cyano, halo$C_{1-6}$alkyl, halogen, halo$C_{1-6}$alkoxy. In some embodiments, each $R^2$, $R^3$, $R^4$, $R^5$, and $R^6$ is independently selected from hydrogen, chloro, trifluoromethyl, and trifluoromethoxy.

In compounds of formula (Ia), (Ib), (Ic), (Id), and (Ie), any A group can be combined with any $R^1$ group; any combination of $R^2$, $R^3$, $R^4$, $R^5$, and $R^6$ groups; any combination of $R^7$, $R^8$, $R^9$, and $R^{10}$ groups; and any combination of $R^{30}$ and $R^{31}$ groups; provided that when A is phenyl, optionally substituted phenyl, methyl, or butyl, and $R^3$ or $R^5$ is halo, then $R^2$ and $R^6$ are other than methyl or chloro; and provided that when A is phenyl, optionally substituted phenyl, methyl, or butyl, and $R^4$ is iodo or ethynyl, then at least one of $R^2$, $R^3$, $R^5$, and $R^6$ is other than hydrogen.

In some embodiments, the invention provides compounds according to formula Ia:

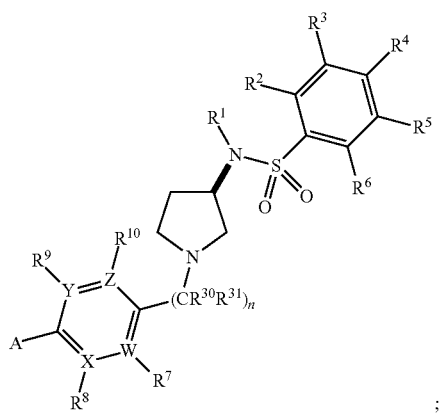

(Ia)

wherein A is selected from phenyl, substituted phenyl, thiophenyl, and pyrazolyl; and each $R^2$, $R^3$, $R^4$, $R^5$, and $R^6$ is independently selected from hydrogen, $C_{1-6}$alkyl, $C_{1-6}$alkoxy, cyano, halo$C_{1-6}$alkyl, halogen, halo$C_{1-6}$alkoxy. In some of these embodiments, both $R^{30}$ and $R^{31}$ are hydrogen and subscript n is 1.

In some embodiments, the invention provides compounds according to formula Ia:

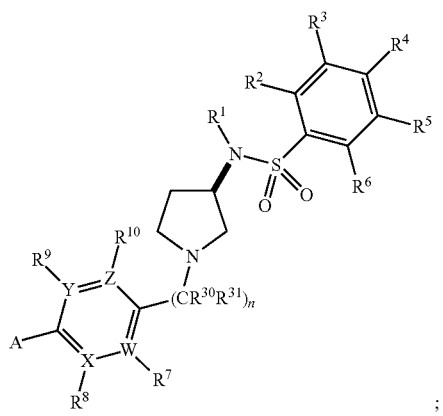

(Ia)

wherein A is selected from phenyl, substituted phenyl, thiophenyl, and pyrazolyl; and each $R^2$, $R^3$, $R^4$, $R^5$, and $R^6$ is independently selected from hydrogen, chloro, trifluoromethyl, and trifluoromethoxy. In some of these embodiments, both $R^{30}$ and $R^{31}$ are hydrogen and subscript n is 1.

In some embodiments, the invention provides compounds according to formula Ia:

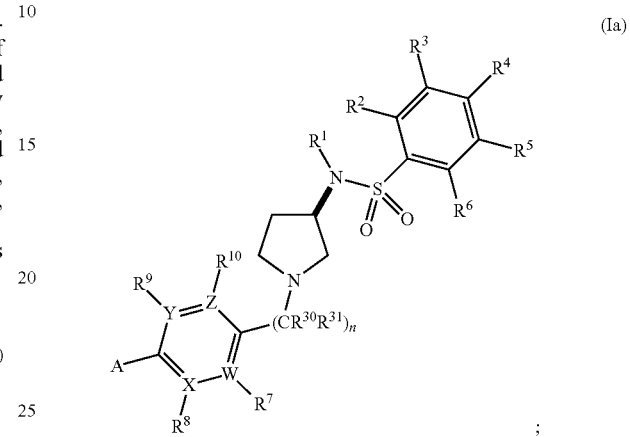

(Ia)

wherein A is selected from the group consisting of —$OC_{1-12}$alkyl, —$OC_{6-10}$aryl, —$OC_{4-9}$heteroaryl, —$OC_{3-8}$cycloalkyl, and —$OC_{3-8}$heterocycloalkyl; and each $R^2$, $R^3$, $R^4$, $R^5$, and $R^6$ is independently selected from the group consisting of hydrogen, $C_{1-6}$alkyl, $C_{1-6}$alkoxy, cyano, halo$C_{1-6}$alkyl, halogen, halo$C_{1-6}$alkoxy. In some of these embodiments, both $R^{30}$ and $R^{31}$ are hydrogen and subscript n is 1.

In some embodiments, the invention provides compounds according to formula Ia:

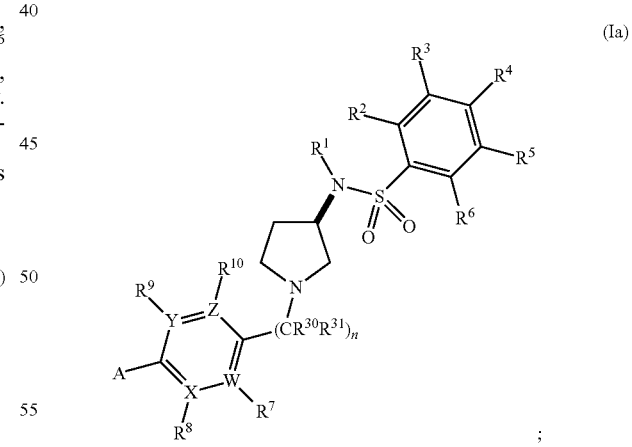

(Ia)

wherein A is selected from the group consisting of —$OC_{1-12}$alkyl, —$OC_{6-10}$aryl, —$OC_{4-9}$heteroaryl, —$OC_{3-8}$cycloalkyl, and —$OC_{3-8}$heterocycloalkyl; and each $R^2$, $R^3$, $R^4$, $R^5$, and $R^6$ is independently selected from the group consisting of hydrogen, chloro, trifluoromethyl, and trifluoromethoxy. In some of these embodiments, both $R^{30}$ and $R^{31}$ are hydrogen and subscript n is 1.

In some embodiments, the invention provides compounds according to formula Ia:

(Ia)

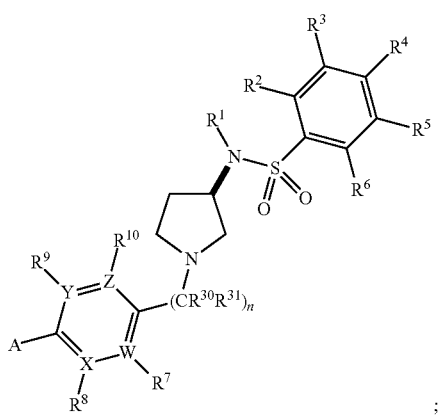

wherein A is selected from phenyl, 4-chlorophenyl, 3-chlorophenyl, thiophen-2-yl, and 1H-pyrazol-1-yl; and each $R^2$, $R^3$, $R^4$, $R^5$, and $R^6$ is independently selected from hydrogen, $C_{1-6}$alkyl, $C_{1-6}$alkoxy, cyano, halo$C_{1-6}$alkyl, halogen, halo$C_{1-6}$alkoxy. In some of these embodiments, both $R^{30}$ and $R^{31}$ are hydrogen and subscript n is 1.

In some embodiments, the invention provides compounds according to formula Ia:

(Ia)

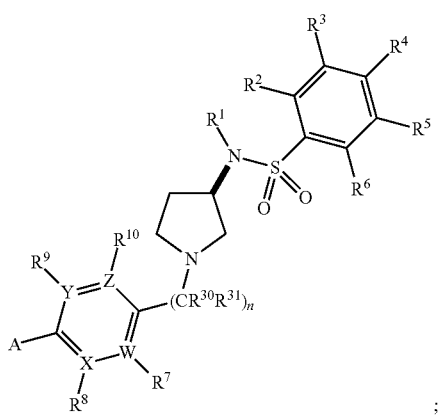

wherein A is selected from phenyl, 4-chlorophenyl, 3-chlorophenyl, thiophen-2-yl, and 1H-pyrazol-1-yl; and each $R^2$, $R^3$, $R^4$, $R^5$, and $R^6$ is independently selected from hydrogen, chloro, trifluoromethyl, and trifluoromethoxy. In some of these embodiments, both $R^{30}$ and $R^{31}$ are hydrogen and subscript n is 1.

In some embodiments, the invention provides compounds according to formula Ia:

(Ia)

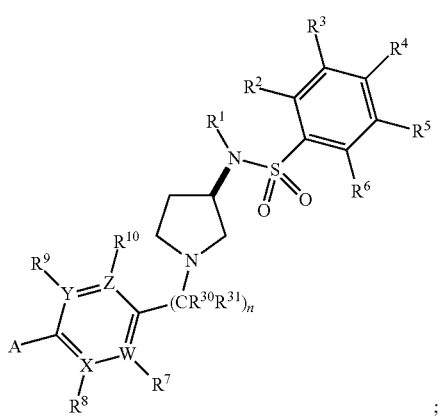

;

wherein A is selected from isobutyloxy, cyclopropyloxy, cyclobutyloxy, and cyclopentyloxy; and each $R^2$, $R^3$, $R^4$, $R^5$, and $R^6$ is independently selected from hydrogen, $C_{1-6}$alkyl, $C_{1-6}$alkoxy, cyano, halo$C_{1-6}$alkyl, halogen, halo$C_{1-6}$alkoxy. In some of these embodiments, both $R^{30}$ and $R^{31}$ are hydrogen and subscript n is 1.

In some embodiments, the invention provides compounds according to formula Ia:

(Ia)

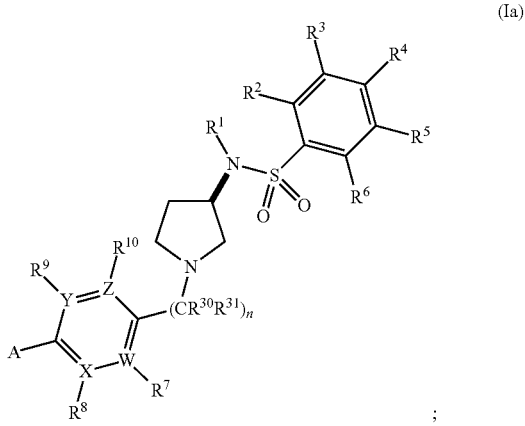

;

wherein A is selected from isobutyloxy, cyclopropyloxy, cyclobutyloxy, and cyclopentyloxy; and each $R^2$, $R^3$, $R^4$, $R^5$, and $R^6$ is independently selected from hydrogen, chloro, trifluoromethyl, and trifluoromethoxy. In some of these embodiments, both $R^{30}$ and $R^{31}$ are hydrogen and subscript n is 1.

In compounds of formula (Ia-h), (Ib-h), (Ic-h), (Id-h), and (Ie-h), any A group can be combined with any $R^1$ group; any combination of $R^7$, $R^8$, $R^9$, and $R^{10}$ groups; any combination of $R^{30}$ and $R^{31}$ groups; and any $Het^1$ group. $Het^1$, in turn, can be substituted with any combination of $R^2$, $R^3$, $R^4$, $R^5$, and $R^6$ groups.

In some embodiments, the invention provides compounds according to formula Ia-h:

(Ia-h)

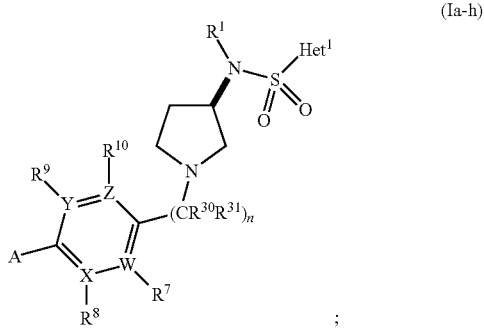

;

wherein A is selected from —$OC_{1-12}$alkyl, —$OC_{6-10}$aryl, —$OC_{4-9}$heteroaryl, —$OC_{3-8}$cycloalkyl, and —$OC_{3-8}$heterocycloalkyl; and $Het^1$ is selected from imidazolyl, pyridinyl, indolyl, benzofuranyl, pyrazolo[b]pyridinyl, thieno[b]pyridinyl, and benzo[b]thiophenyl. In some of these embodiments, both $R^{30}$ and $R^{31}$ are hydrogen.

In some embodiments, the invention provides compounds according to formula Ia-h:

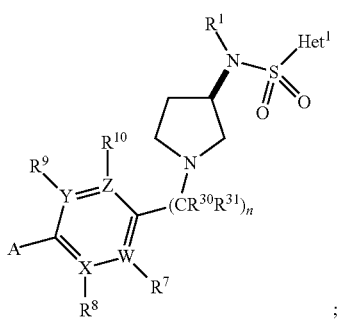
(Ia-h)

wherein A is selected from —OC$_{1-12}$alkyl, —OC$_{6-10}$aryl, —OC$_{4-9}$heteroaryl, —OC$_{3-8}$cycloalkyl, and —OC$_{3-8}$heterocycloalkyl; and Het$^1$ is 5-chloro-3-methylbenzo [b]thiophene-2-yl. In some of these embodiments, both R$^{30}$ and R$^{31}$ are hydrogen.

In some embodiments, the invention provides compounds according to formula Ia-h:

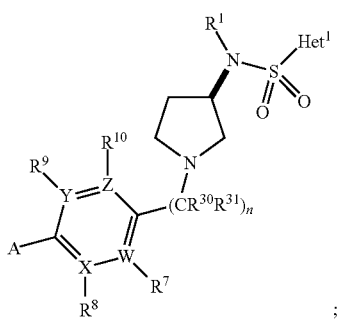
(Ia-h)

wherein A is selected from isobutyloxy, cyclopropyloxy, cyclobutyloxy, and cyclopentyloxy; and Het$^1$ is selected from imidazolyl, pyridinyl, indolyl, benzofuranyl, pyrazolo [b]pyridinyl, thieno[b]pyridinyl, and benzo[b]thiophenyl. In some of these embodiments, both R$^{30}$ and R$^{31}$ are hydrogen.

In some embodiments, the invention provides compounds according to formula Ia-h:

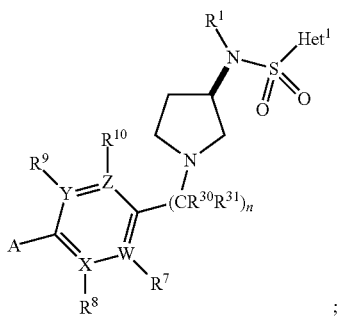
(Ia-h)

wherein A is selected from isobutyloxy, cyclopropyloxy, cyclobutyloxy, and cyclopentyloxy; and Het$^1$ is 5-chloro-3-methylbenzo [b]thiophene-2-yl. In some of these embodiments, both R$^{30}$ and R$^{31}$ are hydrogen.

In compounds of formula (Ia-h2), any Het$^2$ group can be optionally substituted with any A group and can be combined with any R$^1$ group; any combination of R$^7$, R$^8$, R$^9$, and R$^{10}$ groups; any combination of R$^{30}$ and R$^{31}$ groups; and any Het$^1$ group which can, in turn, be substituted with any combination of R$^2$, R$^3$, R$^4$, R$^5$, and R$^6$ groups. In compounds of formula (Ia-h3), any Het$^2$ group can be optionally substituted with any A group and can be combined with any R$^1$ group; any combination of R$^2$, R$^3$, R$^4$, R$^5$, and R$^6$ groups; any combination of R$^7$, R$^8$, R$^9$, and R$^{10}$ groups; and any combination of R$^{30}$ and R$^{31}$ groups.

In some embodiments, the invention provides one or more compound selected from those set forth in Table 1 and pharmaceutically acceptable salts thereof.

TABLE 1

Gyramide compounds.

| No. | Structure |
| --- | --- |
| 1 | 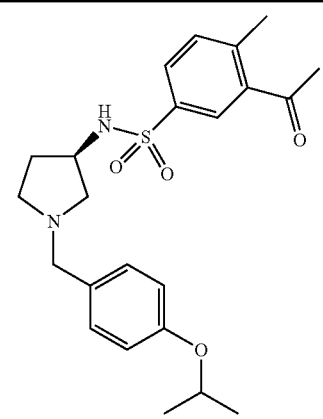 |
| 2 | 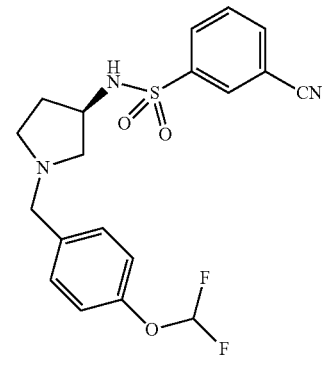 [SMILES: N#Cc1cccc(S(=O)(=O)N[C@@H]2CCN(Cc3ccc(OC(F)F)cc3)C2)c1] |
| 3 | 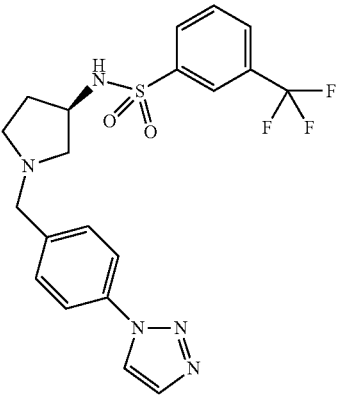 [SMILES: O=S(=O)(N[C@@H]1CCN(Cc2ccc(-n3ccnn3)cc2)C1)c1cccc(C(F)(F)F)c1] |

TABLE 1-continued

Gyramide compounds.

| No. | Structure |
|---|---|
| 4 | (structure) |
| 5 | (structure) |
| 6 | (structure) |
| 7 | (structure) |
| 8 | (structure) |
| 9 | (structure) |
| 10 | (structure) |

TABLE 1-continued
Gyramide compounds.
| No. | Structure |
|---|---|
| 11 | 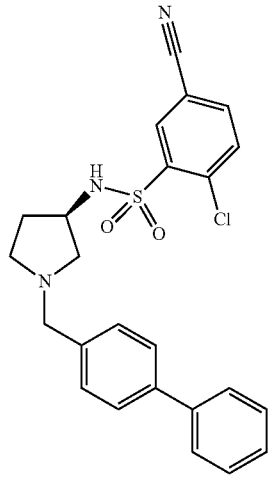 [SMILES: N#Cc1ccc(Cl)c(S(=O)(=O)N[C@@H]2CCN(Cc3ccc(-c4ccccc4)cc3)C2)c1] |
| 12 | 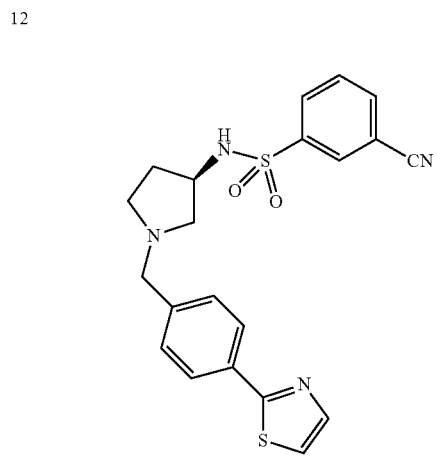 |
| 13 | 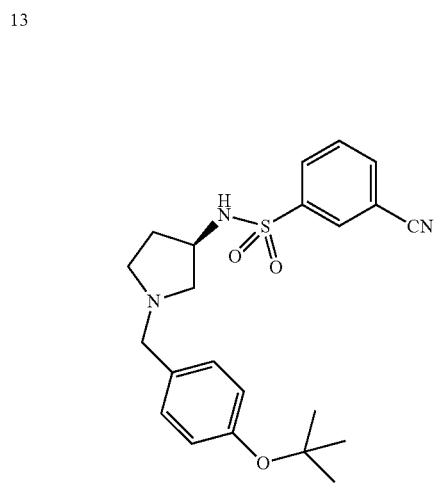 |
TABLE 1-continued
Gyramide compounds.
| No. | Structure |
|---|---|
| 14 | 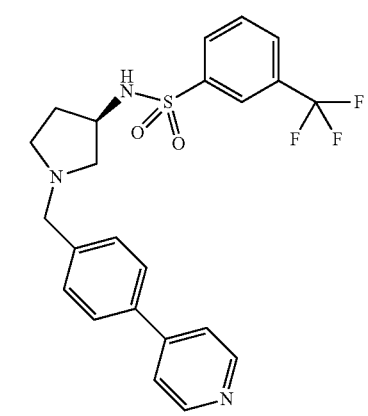 [SMILES: O=S(=O)(N[C@@H]1CCN(Cc2ccc(-c3ccncc3)cc2)C1)c1cccc(C(F)(F)F)c1] |
| 15 | 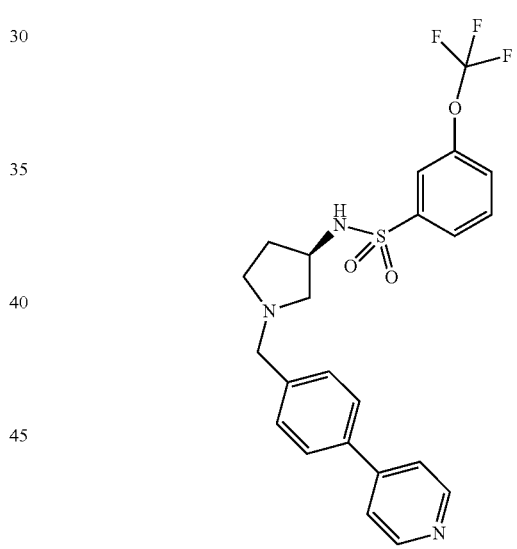 |
| 16 | 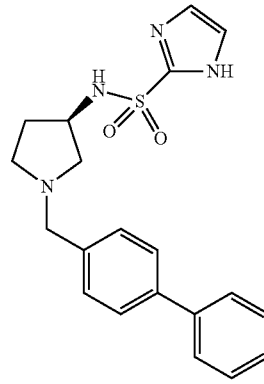 |

TABLE 1-continued
Gyramide compounds.
| No. | Structure |
|---|---|
| 17 | 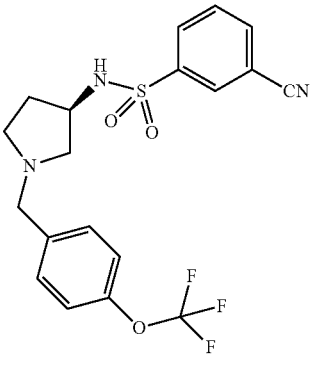 [SMILES: N#Cc1cccc(S(=O)(=O)N[C@@H]2CCN(Cc3ccc(OC(F)(F)F)cc3)C2)c1] |
| 18 | 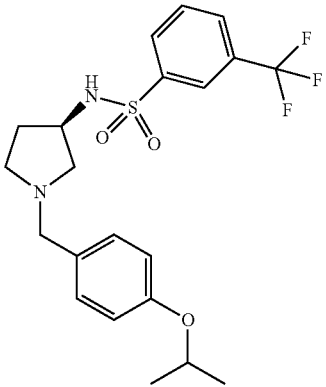 [SMILES: CC(C)Oc1ccc(CN2CC[C@@H](NS(=O)(=O)c3cccc(C(F)(F)F)c3)C2)cc1] |
| 19 | 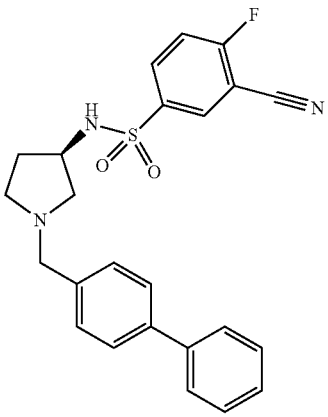 [SMILES: N#Cc1cc(S(=O)(=O)N[C@@H]2CCN(Cc3ccc(-c4ccccc4)cc3)C2)ccc1F] |
| 20 | 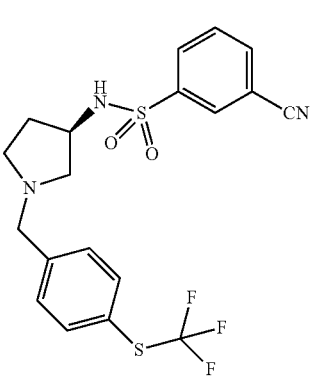 [SMILES: N#Cc1cccc(S(=O)(=O)N[C@@H]2CCN(Cc3ccc(SC(F)(F)F)cc3)C2)c1] |
| 21 | 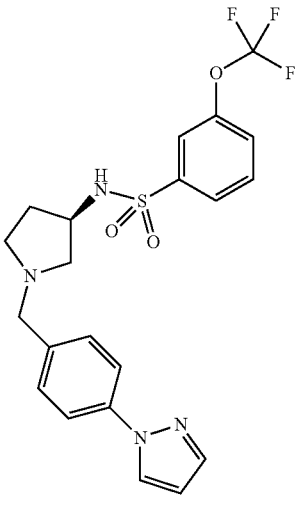 [SMILES: O=S(=O)(N[C@@H]1CCN(Cc2ccc(-n3cccn3)cc2)C1)c1cccc(OC(F)(F)F)c1] |
| 22 | 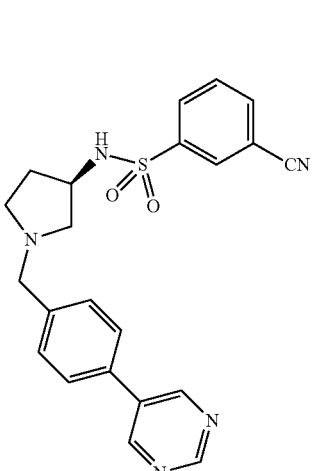 |
| 23 | 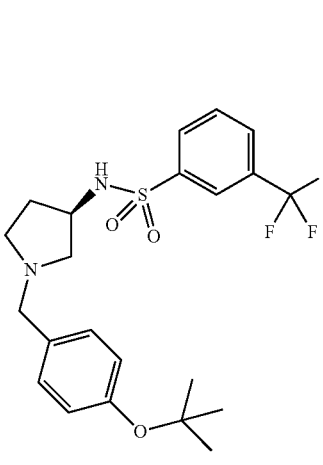 |

TABLE 1-continued
Gyramide compounds.
| No. | Structure |
|---|---|
| 24 | 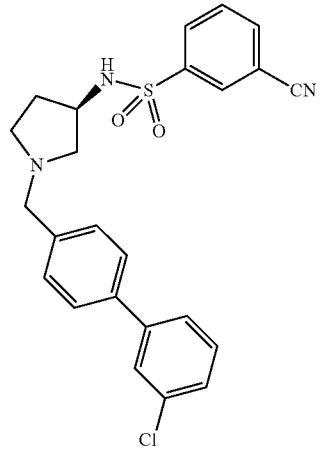 [SMILES: N#Cc1cccc(S(=O)(=O)N[C@@H]2CCN(Cc3ccc(-c4cccc(Cl)c4)cc3)C2)c1] |
| 25 | 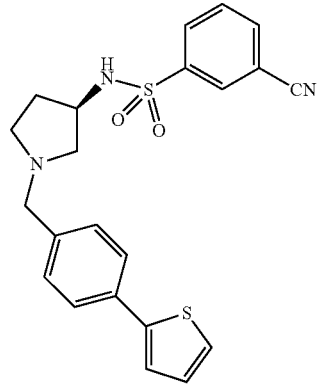 [SMILES: N#Cc1cccc(S(=O)(=O)N[C@@H]2CCN(Cc3ccc(-c4cccs4)cc3)C2)c1] |
| 26 | 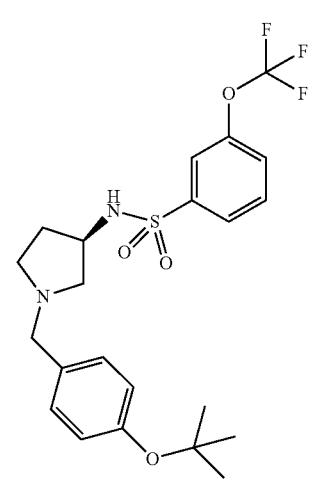 [SMILES: CC(C)(C)Oc1ccc(CN2CC[C@@H](NS(=O)(=O)c3cccc(OC(F)(F)F)c3)C2)cc1] |
| 27 | 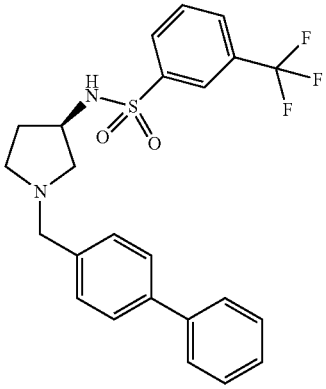 [SMILES: O=S(=O)(N[C@@H]1CCN(Cc2ccc(-c3ccccc3)cc2)C1)c1cccc(C(F)(F)F)c1] |
| 28 | 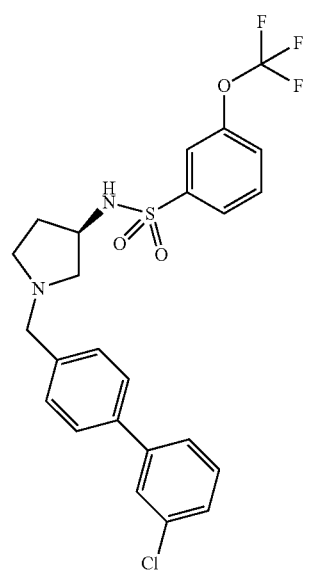 [SMILES: O=S(=O)(N[C@@H]1CCN(Cc2ccc(-c3cccc(Cl)c3)cc2)C1)c1cccc(OC(F)(F)F)c1] |
| 29 | 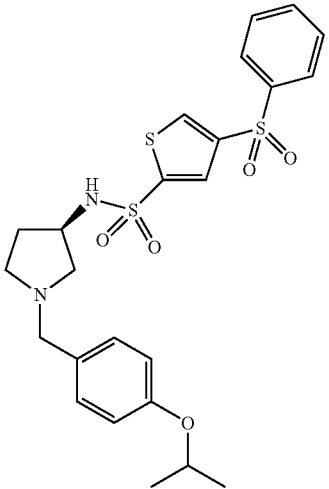 [SMILES: CC(C)Oc1ccc(CN2CC[C@@H](NS(=O)(=O)c3cc(S(=O)(=O)c4ccccc4)cs3)C2)cc1] |

TABLE 1-continued
Gyramide compounds.
| No. | Structure |
|---|---|
| 30 | 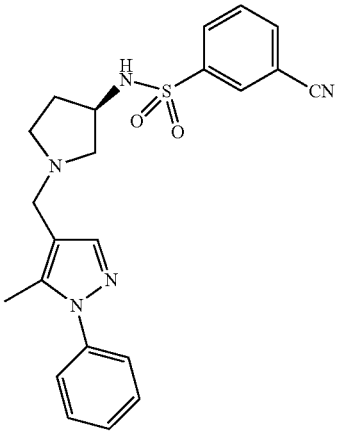 [SMILES: Cc1c(CN2CC[C@@H](NS(=O)(=O)c3cccc(C#N)c3)C2)cnn1-c1ccccc1] |
| 31 | 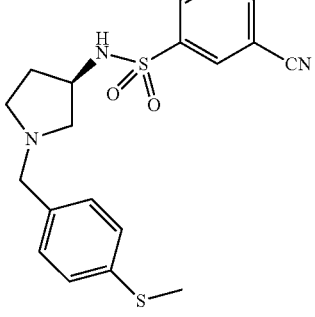 |
| 32 | 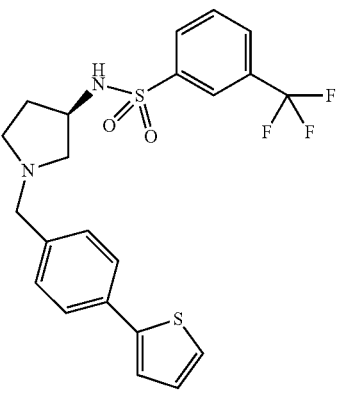 [SMILES: O=S(=O)(N[C@@H]1CCN(Cc2ccc(-c3cccs3)cc2)C1)c1cccc(C(F)(F)F)c1] |
| 33 | 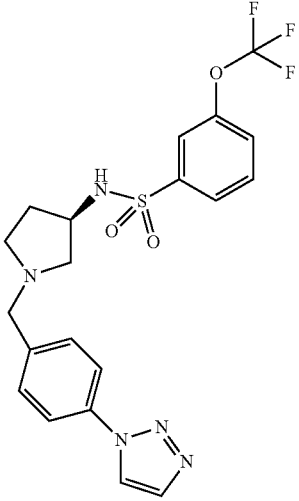 [SMILES: O=S(=O)(N[C@@H]1CCN(Cc2ccc(-n3ccnn3)cc2)C1)c1cccc(OC(F)(F)F)c1] |
| 34 | 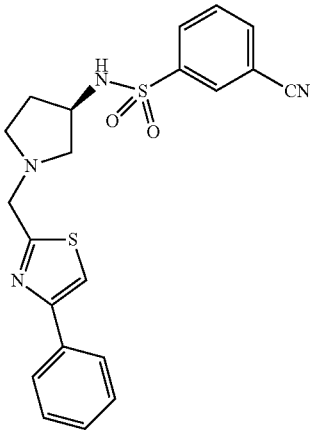 [SMILES: N#Cc1cccc(S(=O)(=O)N[C@@H]2CCN(Cc3nc(-c4ccccc4)cs3)C2)c1] |
| 35 | 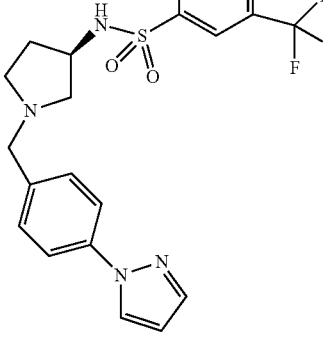 |

TABLE 1-continued

Gyramide compounds.

| No. | Structure |
|---|---|
| 36 | (structure) |
| 37 | (structure) |
| 38 | (structure) |
| 39 | (structure) |
| 40 | (structure) |
| 41 | (structure) |

TABLE 1-continued

Gyramide compounds.

| No. | Structure |
|---|---|
| 42 | 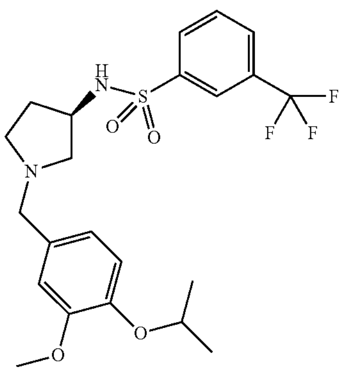 [SMILES: COc1cc(CN2CC[C@@H](NS(=O)(=O)c3cccc(C(F)(F)F)c3)C2)ccc1OC(C)C] |
| 43 | 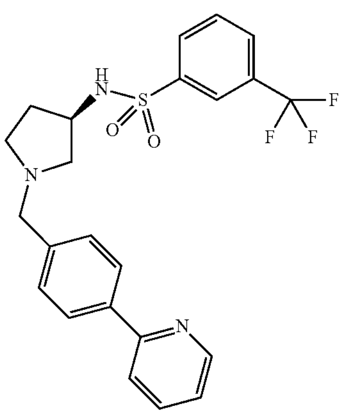 [SMILES: O=S(=O)(N[C@@H]1CCN(Cc2ccc(-c3ccccn3)cc2)C1)c1cccc(C(F)(F)F)c1] |
| 44 | 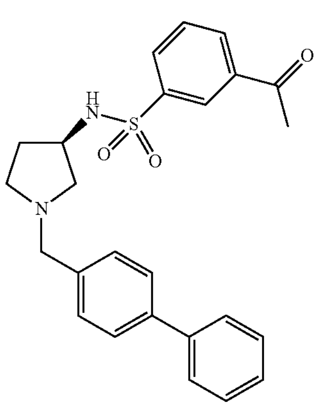 [SMILES: CC(=O)c1cccc(S(=O)(=O)N[C@@H]2CCN(Cc3ccc(-c4ccccc4)cc3)C2)c1] |
| 45 | |
| 46 | |
| 47 | |

TABLE 1-continued
| | Gyramide compounds. | | | Gyramide compounds. | |
|---|---|---|---|---|---|
| No. | Structure | | No. | Structure | |
| 48 | | | 51 | | |
| 49 | 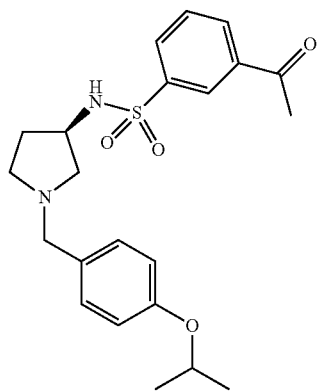 [SMILES: CC(=O)c1cccc(S(=O)(=O)N[C@@H]2CCN(Cc3ccc(OC(C)C)cc3)C2)c1] | | 52 | 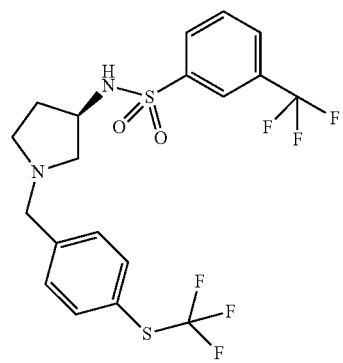 | |
| 50 | 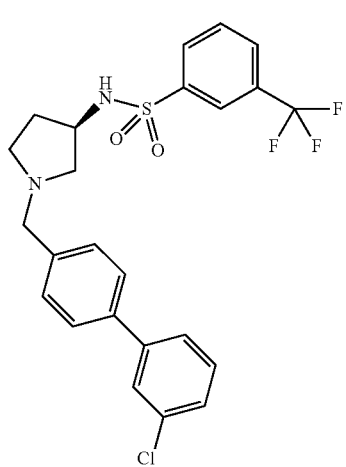 [SMILES: O=S(=O)(N[C@@H]1CCN(Cc2ccc(-c3cccc(Cl)c3)cc2)C1)c1cccc(C(F)(F)F)c1] | | 53 | 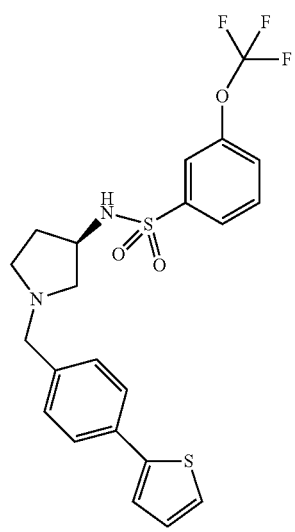 [SMILES: O=S(=O)(N[C@@H]1CCN(Cc2ccc(-c3cccs3)cc2)C1)c1cccc(OC(F)(F)F)c1] | |

TABLE 1-continued
Gyramide compounds.
| No. | Structure |
|---|---|
| 54 | 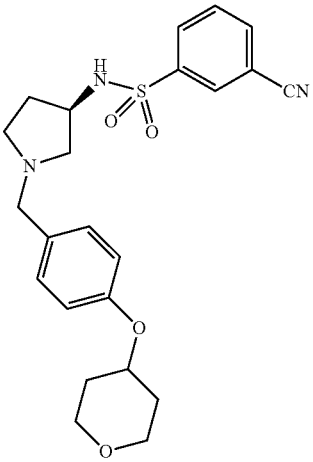 [SMILES: N#Cc1cccc(S(=O)(=O)N[C@@H]2CCN(Cc3ccc(OC4CCOCC4)cc3)C2)c1] |
| 55 | 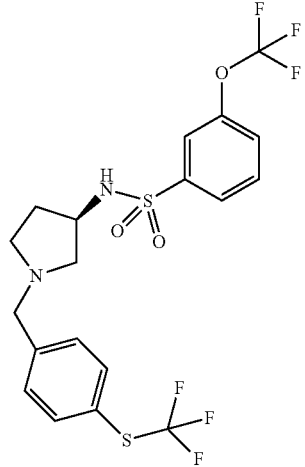 [SMILES: O=S(=O)(N[C@@H]1CCN(Cc2ccc(SC(F)(F)F)cc2)C1)c1cccc(OC(F)(F)F)c1] |
| 56 | 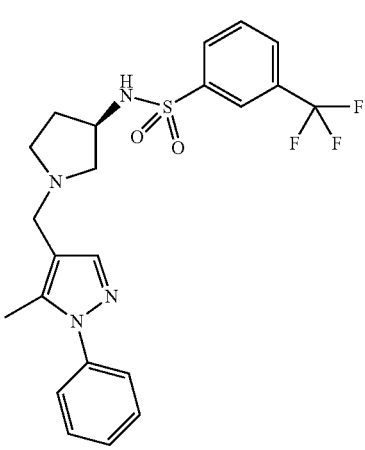 [SMILES: Cc1c(CN2CC[C@@H](NS(=O)(=O)c3cccc(C(F)(F)F)c3)C2)cnn1-c1ccccc1] |
| 57 | 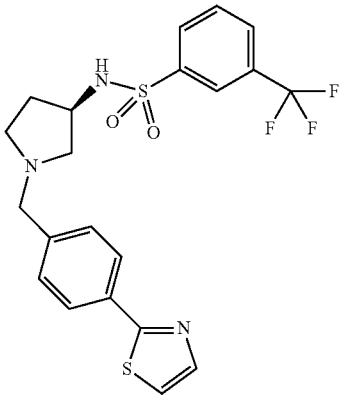 [SMILES: O=S(=O)(N[C@@H]1CCN(Cc2ccc(-c3nccs3)cc2)C1)c1cccc(C(F)(F)F)c1] |
| 58 | 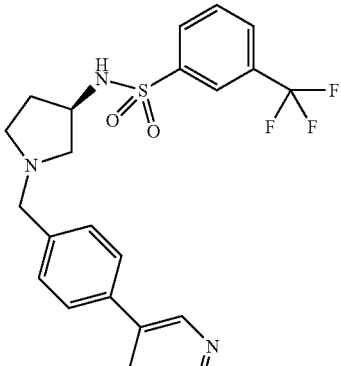 |
| 59 | 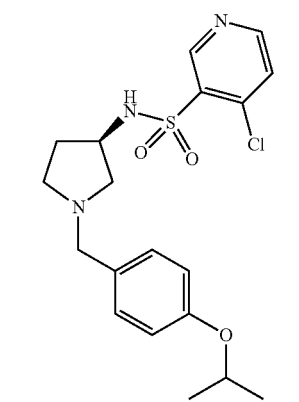 [SMILES: CC(C)Oc1ccc(CN2CC[C@@H](NS(=O)(=O)c3cnccc3Cl)C2)cc1] |

TABLE 1-continued
Gyramide compounds.
| No. | Structure |
|---|---|
| 60 | 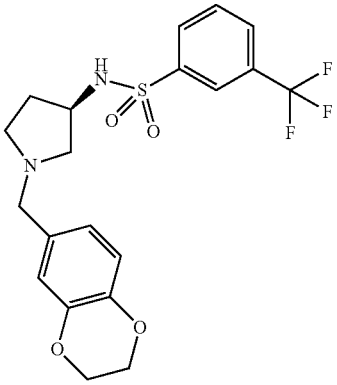 [SMILES: O=S(=O)(N[C@@H]1CCN(Cc2ccc3c(c2)OCCO3)C1)c1cccc(C(F)(F)F)c1] |
| 61 | 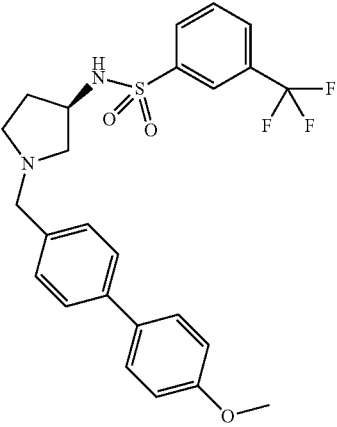 [SMILES: COc1ccc(-c2ccc(CN3CC[C@@H](NS(=O)(=O)c4cccc(C(F)(F)F)c4)C3)cc2)cc1] |
| 62 | 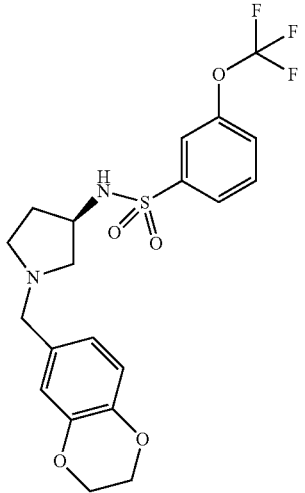 [SMILES: O=S(=O)(N[C@@H]1CCN(Cc2ccc3c(c2)OCCO3)C1)c1cccc(OC(F)(F)F)c1] |
| 63 | 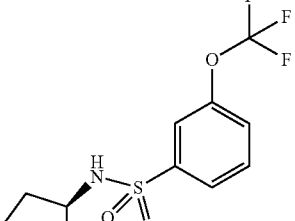 |
| 64 | 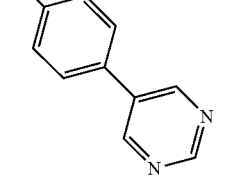 |
| 65 | 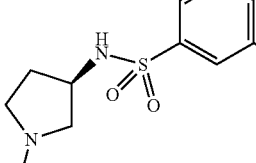 |

TABLE 1-continued
Gyramide compounds.
| No. | Structure |
|---|---|
| 66 | 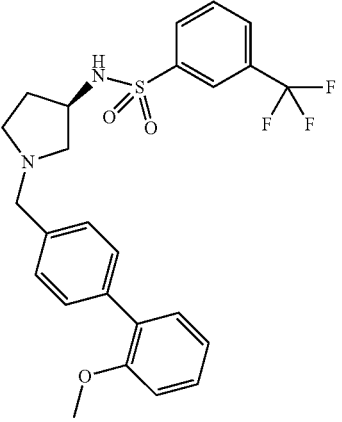 [SMILES: COc1ccccc1-c1ccc(CN2CC[C@@H](NS(=O)(=O)c3cccc(C(F)(F)F)c3)C2)cc1] |
| 67 | 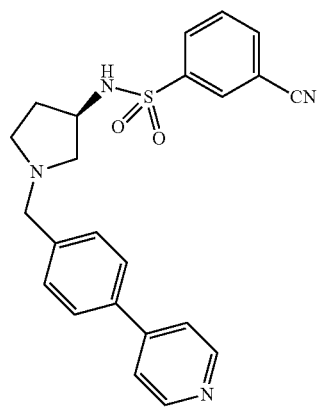 [SMILES: N#Cc1cccc(S(=O)(=O)N[C@@H]2CCN(Cc3ccc(-c4ccncc4)cc3)C2)c1] |
| 68 | 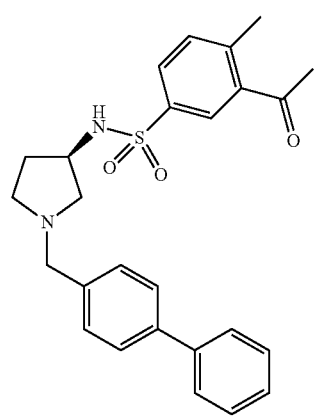 [SMILES: CC(=O)c1cc(S(=O)(=O)N[C@@H]2CCN(Cc3ccc(-c4ccccc4)cc3)C2)ccc1C] |
| 69 | 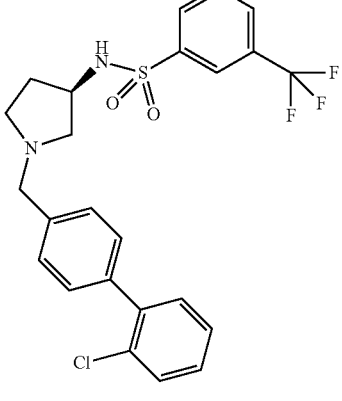 |
| 70 | 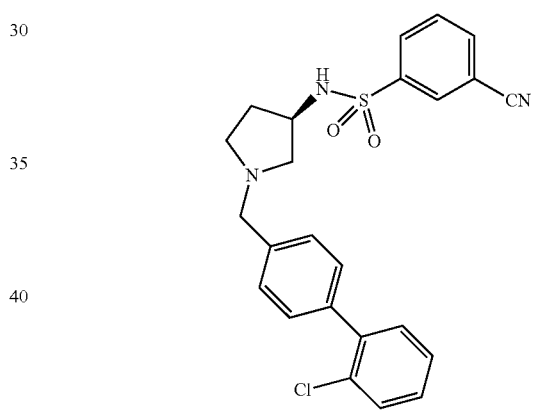 |
| 71 | 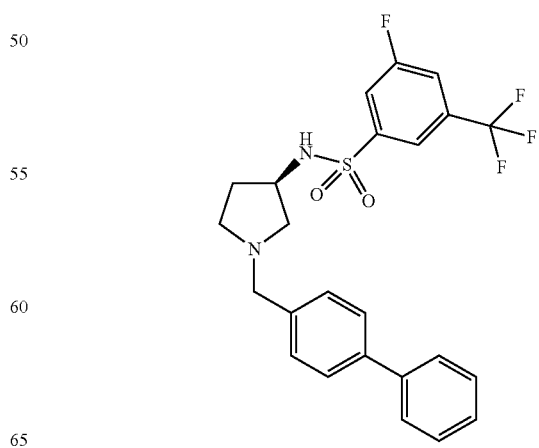 |
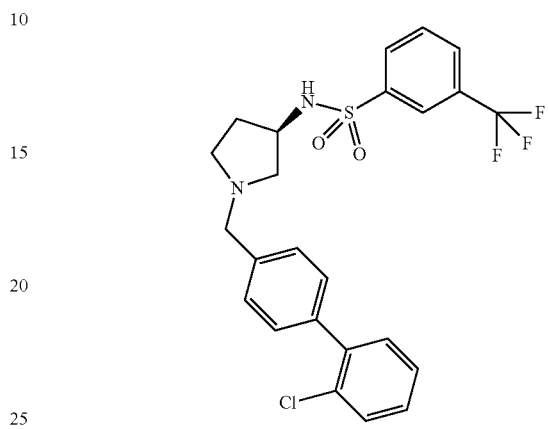

TABLE 1-continued
Gyramide compounds.
| No. | Structure |
|---|---|
| 72 | 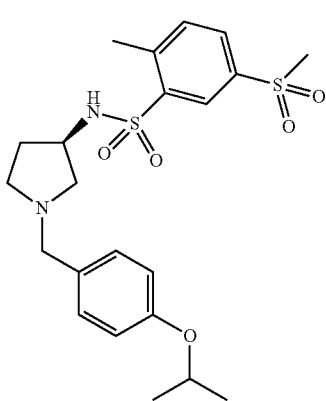 [SMILES: Cc1ccc(S(C)(=O)=O)cc1S(=O)(=O)N[C@@H]1CCN(Cc2ccc(OC(C)C)cc2)C1] |
| 73 | 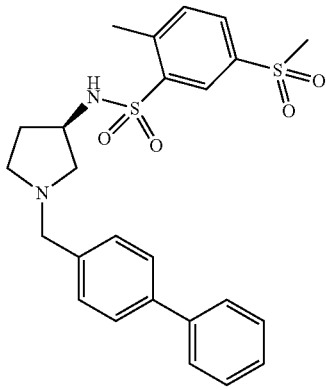 [SMILES: Cc1ccc(S(C)(=O)=O)cc1S(=O)(=O)N[C@@H]1CCN(Cc2ccc(-c3ccccc3)cc2)C1] |
| 74 | 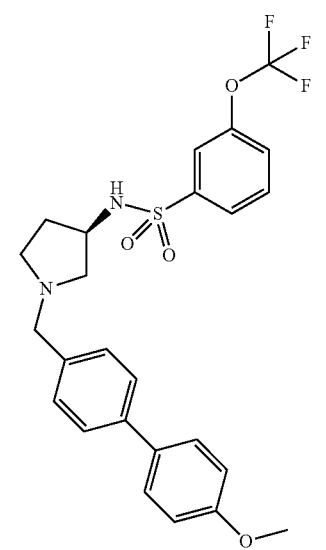 [SMILES: COc1ccc(-c2ccc(CN3CC[C@@H](NS(=O)(=O)c4cccc(OC(F)(F)F)c4)C3)cc2)cc1] |
| 75 | 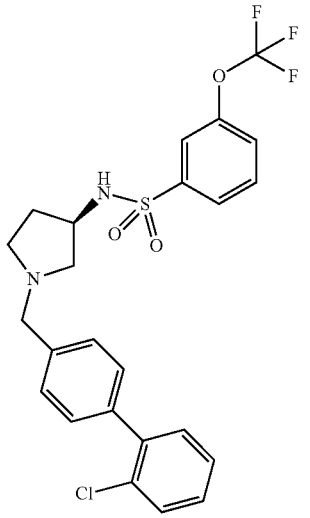 [SMILES: O=S(=O)(N[C@@H]1CCN(Cc2ccc(-c3ccccc3Cl)cc2)C1)c1cccc(OC(F)(F)F)c1] |
| 76 | 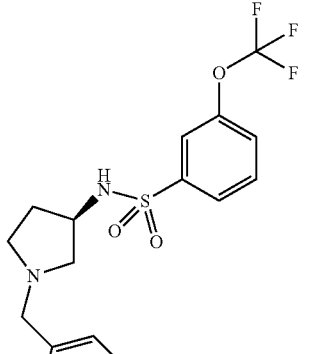 |
| 77 | 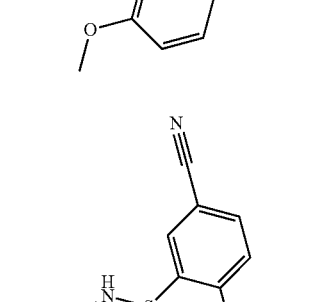 |

TABLE 1-continued
Gyramide compounds.
| No. | Structure |
|---|---|
| 78 | 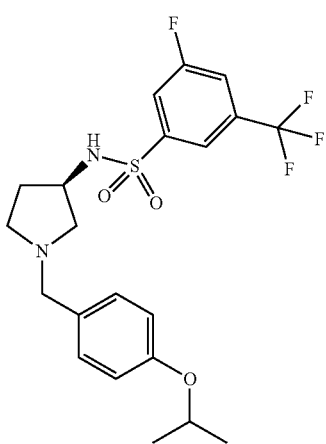 [SMILES: CC(C)Oc1ccc(CN2CC[C@@H](NS(=O)(=O)c3cc(F)cc(C(F)(F)F)c3)C2)cc1] |
| 79 | 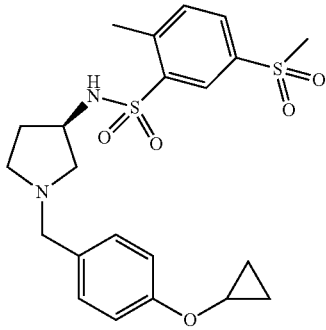 [SMILES: Cc1ccc(S(C)(=O)=O)cc1S(=O)(=O)N[C@@H]1CCN(Cc2ccc(OC3CC3)cc2)C1] |
| 80 | 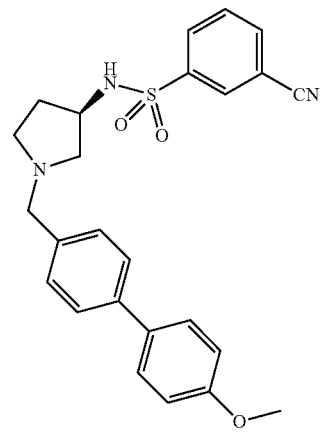 [SMILES: COc1ccc(-c2ccc(CN3CC[C@@H](NS(=O)(=O)c4cccc(C#N)c4)C3)cc2)cc1] |
| 81 | 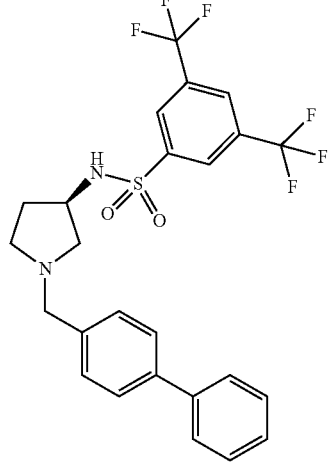 |
| 82 | 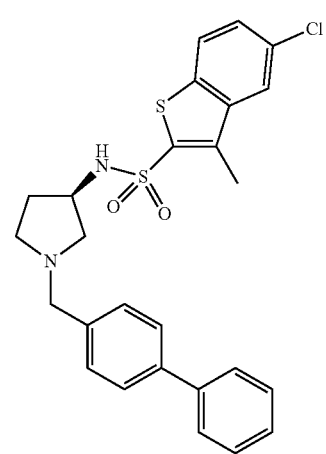 [SMILES: Cc1c(S(=O)(=O)N[C@@H]2CCN(Cc3ccc(-c4ccccc4)cc3)C2)sc2ccc(Cl)cc12] |
| 83 | 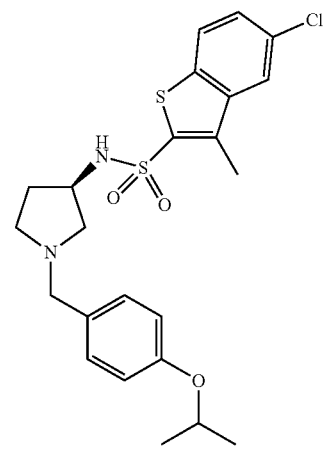 [SMILES: Cc1c(S(=O)(=O)N[C@@H]2CCN(Cc3ccc(OC(C)C)cc3)C2)sc2ccc(Cl)cc12] |

TABLE 1-continued

Gyramide compounds.

| No. | Structure |
|---|---|
| 84 | 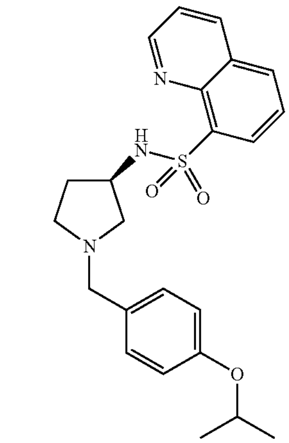 [SMILES: CC(C)Oc1ccc(CN2CC[C@@H](NS(=O)(=O)c3cccc4cccnc34)C2)cc1] |
| 85 | 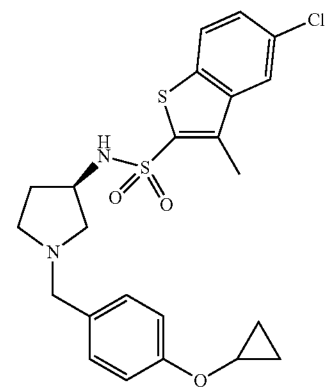 [SMILES: Cc1c(S(=O)(=O)N[C@@H]2CCN(Cc3ccc(OC4CC4)cc3)C2)sc2ccc(Cl)cc12] |
| 86 | 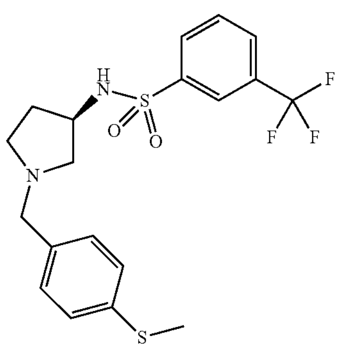 [SMILES: CSc1ccc(CN2CC[C@@H](NS(=O)(=O)c3cccc(C(F)(F)F)c3)C2)cc1] |
| 87 | 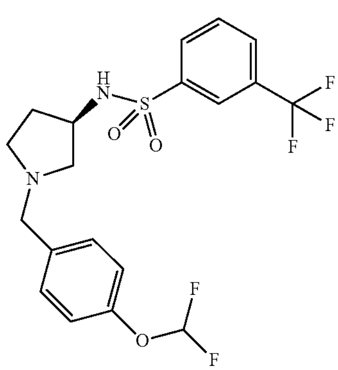 [SMILES: O=S(=O)(N[C@@H]1CCN(Cc2ccc(OC(F)F)cc2)C1)c1cccc(C(F)(F)F)c1] |
| 88 | |
| 89 | |
| 90 | |

TABLE 1-continued

Gyramide compounds.

| No. | Structure |
|---|---|
| 91 | 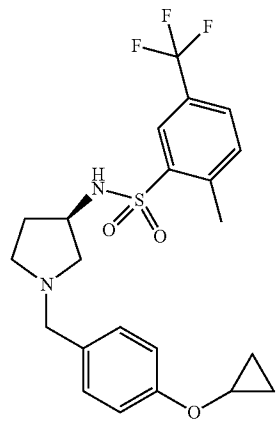 [SMILES: Cc1ccc(C(F)(F)F)cc1S(=O)(=O)N[C@@H]1CCN(Cc2ccc(OC3CC3)cc2)C1] |
| 92 | 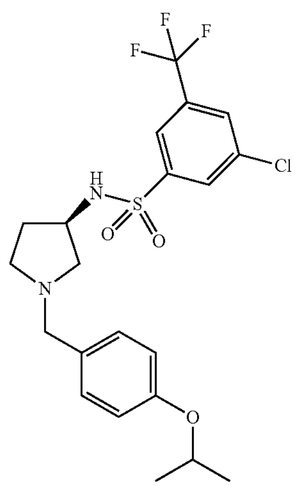 [SMILES: CC(C)Oc1ccc(CN2CC[C@@H](NS(=O)(=O)c3cc(Cl)cc(C(F)(F)F)c3)C2)cc1] |
| 93 | 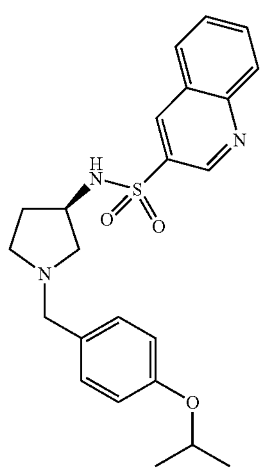 [SMILES: CC(C)Oc1ccc(CN2CC[C@@H](NS(=O)(=O)c3cnc4ccccc4c3)C2)cc1] |
| 94 | |
| 95 | |
| 96 | |

TABLE 1-continued
Gyramide compounds.
| No. | Structure |
|---|---|
| 97 | 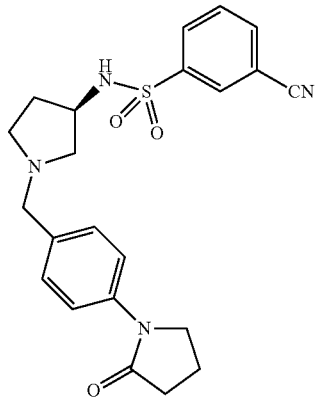 [SMILES: N#Cc1cccc(S(=O)(=O)N[C@@H]2CCN(Cc3ccc(N4CCCC4=O)cc3)C2)c1] |
| 98 | 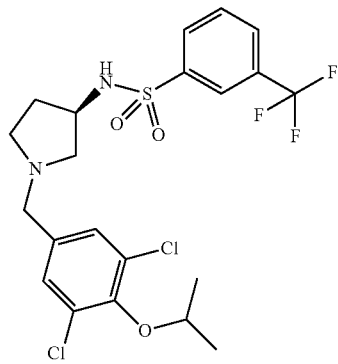 [SMILES: CC(C)Oc1c(Cl)cc(CN2CC[C@@H](NS(=O)(=O)c3cccc(C(F)(F)F)c3)C2)cc1Cl] |
| 99 | 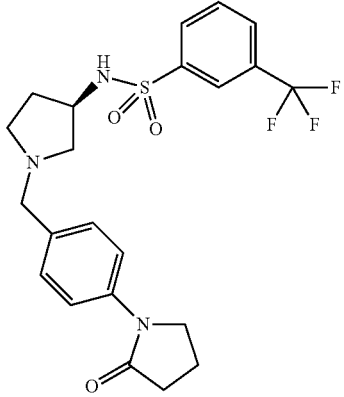 [SMILES: O=C1CCCN1c1ccc(CN2CC[C@@H](NS(=O)(=O)c3cccc(C(F)(F)F)c3)C2)cc1] |
TABLE 1-continued
Gyramide compounds.
| No. | Structure |
|---|---|
| 100 | 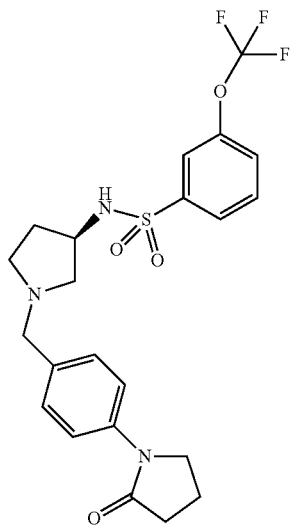 [SMILES: O=C1CCCN1c1ccc(CN2CC[C@@H](NS(=O)(=O)c3cccc(OC(F)(F)F)c3)C2)cc1] |
| 101 | 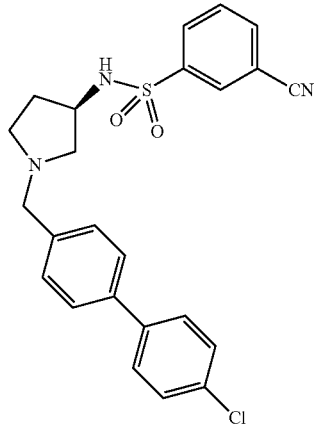 |
| 102 | 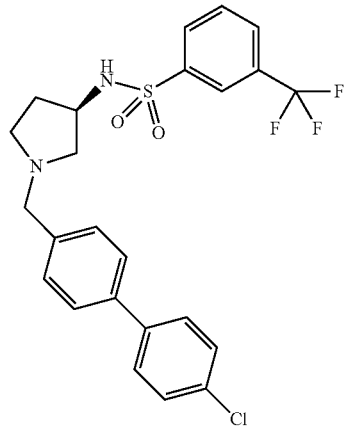 [SMILES: O=S(=O)(N[C@@H]1CCN(Cc2ccc(-c3ccc(Cl)cc3)cc2)C1)c1cccc(C(F)(F)F)c1] |

TABLE 1-continued
Gyramide compounds.
| No. | Structure |
|---|---|
| 103 | 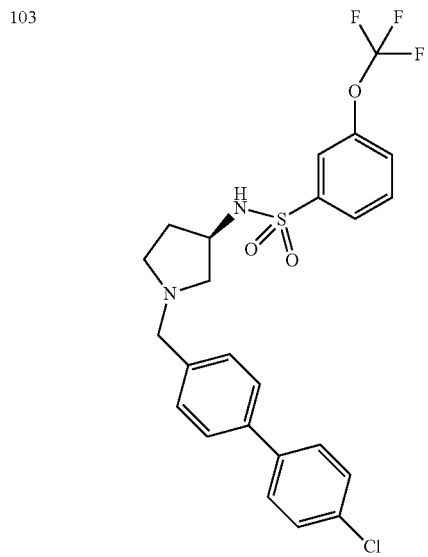 |
| 104 | 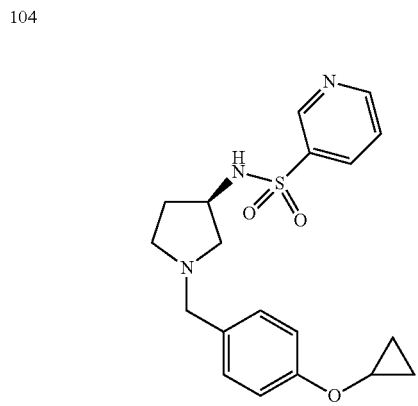 |
| 105 | 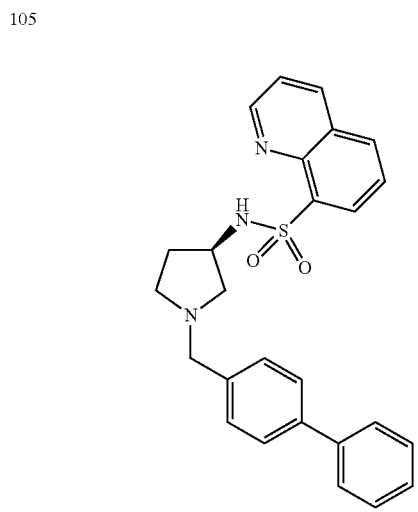 |
TABLE 1-continued
Gyramide compounds.
| No. | Structure |
|---|---|
| 106 | 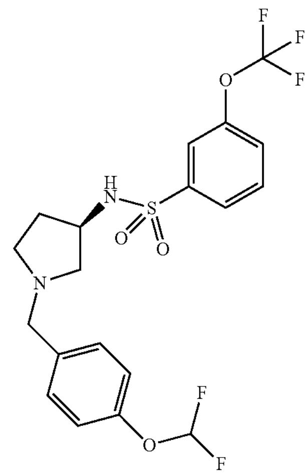 [SMILES: O=S(=O)(N[C@@H]1CCN(Cc2ccc(OC(F)F)cc2)C1)c1cccc(OC(F)(F)F)c1] |
| 107 | 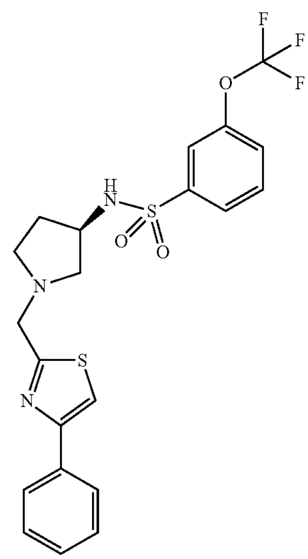 [SMILES: O=S(=O)(N[C@@H]1CCN(Cc2nc(-c3ccccc3)cs2)C1)c1cccc(OC(F)(F)F)c1] |
| 108 | 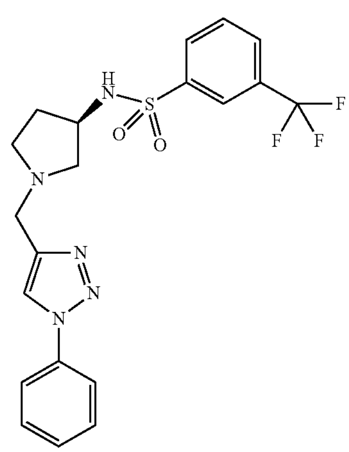 [SMILES: O=S(=O)(N[C@@H]1CCN(Cc2cn(-c3ccccc3)nn2)C1)c1cccc(C(F)(F)F)c1] |

TABLE 1-continued
Gyramide compounds.
| No. | Structure |
|---|---|
| 109 | 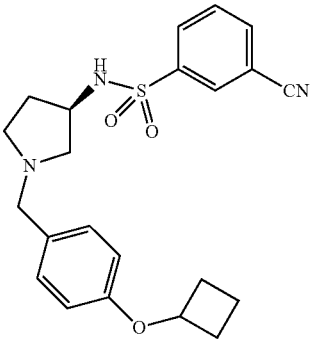 [SMILES: N#Cc1cccc(S(=O)(=O)N[C@@H]2CCN(Cc3ccc(OC4CCC4)cc3)C2)c1] |
| 110 | 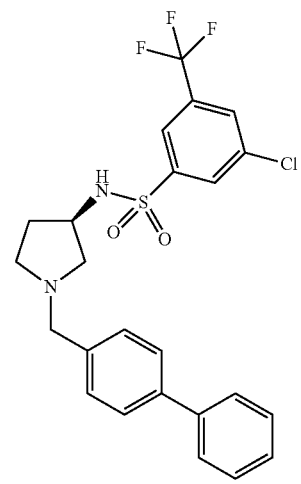 [SMILES: O=S(=O)(N[C@@H]1CCN(Cc2ccc(-c3ccccc3)cc2)C1)c1cc(Cl)cc(C(F)(F)F)c1] |
| 111 | 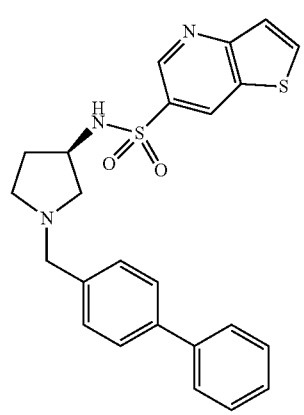 [SMILES: O=S(=O)(N[C@@H]1CCN(Cc2ccc(-c3ccccc3)cc2)C1)c1cnc2ccsc2c1] |
TABLE 1-continued
Gyramide compounds.
| No. | Structure |
|---|---|
| 112 | 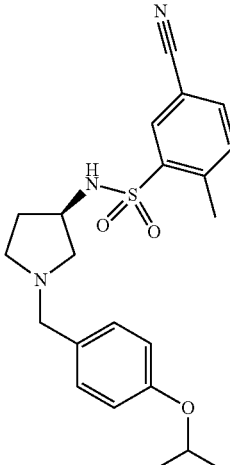 |
| 113 | 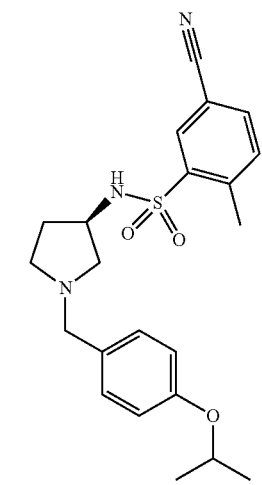 [SMILES: Cc1ccc(C#N)cc1S(=O)(=O)N[C@@H]1CCN(Cc2ccc(OC(C)C)cc2)C1] |
| 114 | 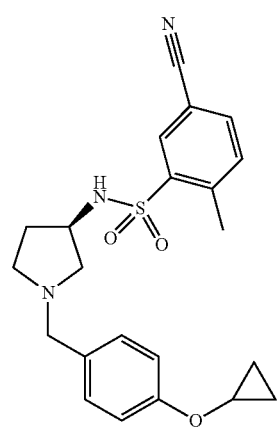 [SMILES: Cc1ccc(C#N)cc1S(=O)(=O)N[C@@H]1CCN(Cc2ccc(OC3CC3)cc2)C1] |

TABLE 1-continued

Gyramide compounds.

| No. | Structure |
|---|---|
| 115 | 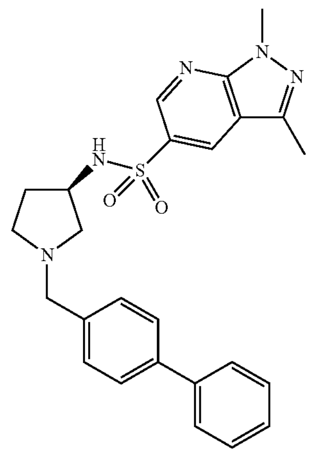 [SMILES: Cc1nn(C)c2ncc(S(=O)(=O)N[C@@H]3CCN(Cc4ccc(-c5ccccc5)cc4)C3)cc12] |
| 116 | 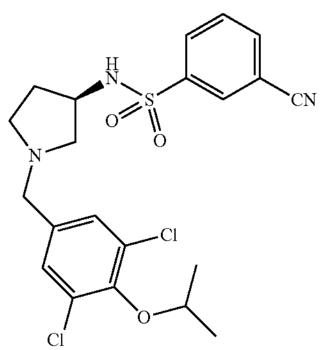 [SMILES: CC(C)Oc1c(Cl)cc(CN2CC[C@@H](NS(=O)(=O)c3cccc(C#N)c3)C2)cc1Cl] |
| 117 | 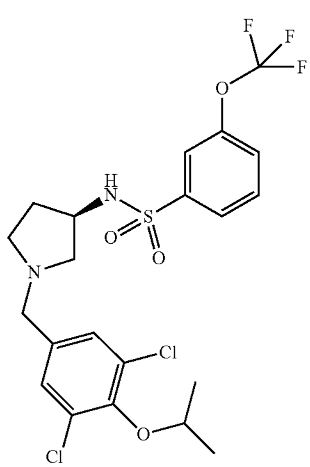 [SMILES: CC(C)Oc1c(Cl)cc(CN2CC[C@@H](NS(=O)(=O)c3cccc(OC(F)(F)F)c3)C2)cc1Cl] |
| 118 | |
| 119 | |
| 120 | |

TABLE 1-continued
Gyramide compounds.
| No. | Structure |
|---|---|
| 121 | 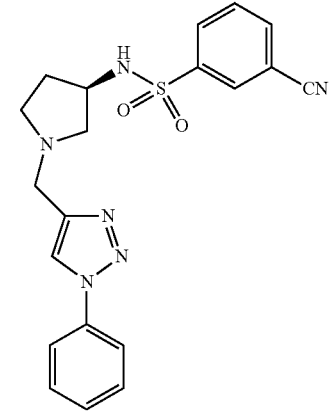 [SMILES: N#Cc1cccc(S(=O)(=O)N[C@@H]2CCN(Cc3cn(-c4ccccc4)nn3)C2)c1] |
| 122 | 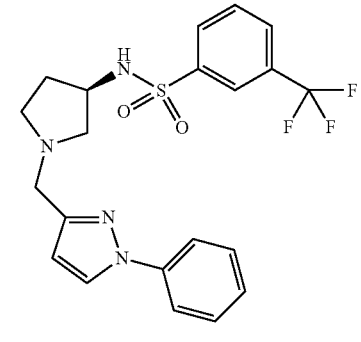 |
| 123 | 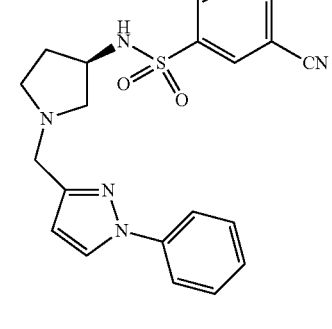 |
| 124 | 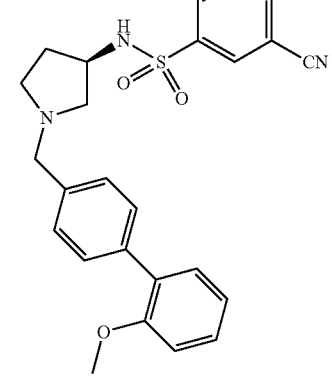 |
| 125 | 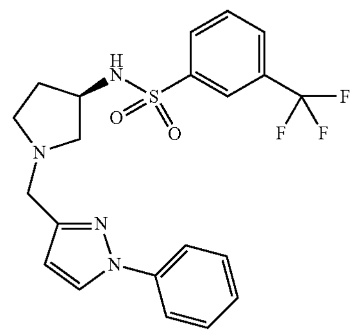 [SMILES: O=S(=O)(N[C@@H]1CCN(Cc2ccn(-c3ccccc3)n2)C1)c1cccc(C(F)(F)F)c1] |
| 126 | 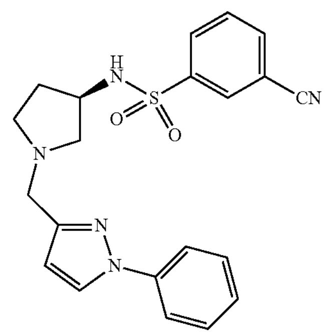 [SMILES: N#Cc1cccc(S(=O)(=O)N[C@@H]2CCN(Cc3ccn(-c4ccccc4)n3)C2)c1] |
| 127 | 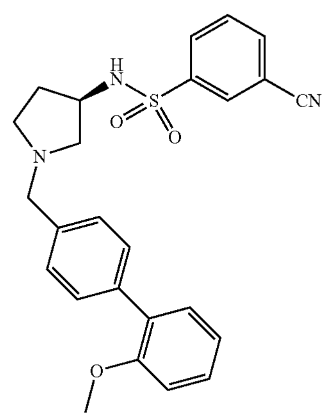 [SMILES: COc1ccccc1-c1ccc(CN2CC[C@@H](NS(=O)(=O)c3cccc(C#N)c3)C2)cc1] |

TABLE 1-continued
Gyramide compounds.
| No. | Structure |
|---|---|
| 128 | 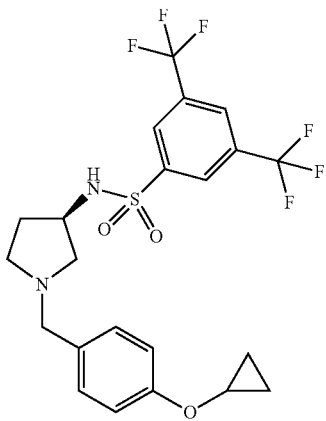 [SMILES: O=S(=O)(N[C@@H]1CCN(Cc2ccc(OC3CC3)cc2)C1)c1cc(C(F)(F)F)cc(C(F)(F)F)c1] |
| 129 | 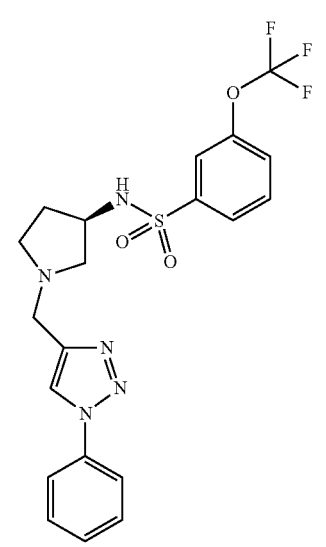 [SMILES: O=S(=O)(N[C@@H]1CCN(Cc2cn(-c3ccccc3)nn2)C1)c1cccc(OC(F)(F)F)c1] |
| 130 | 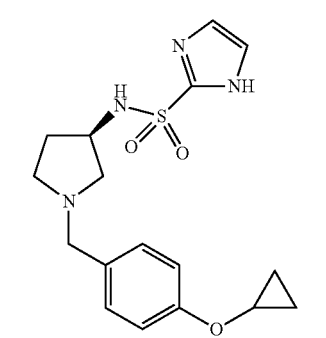 [SMILES: O=S(=O)(N[C@@H]1CCN(Cc2ccc(OC3CC3)cc2)C1)c1ncc[nH]1] |
| 131 | 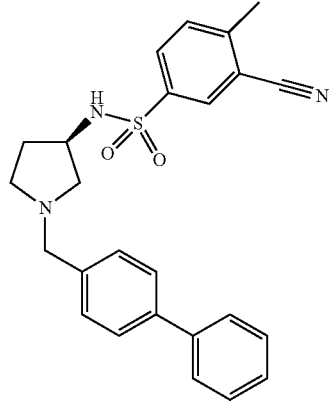 [SMILES: Cc1ccc(S(=O)(=O)N[C@@H]2CCN(Cc3ccc(-c4ccccc4)cc3)C2)cc1C#N] |
| 132 | 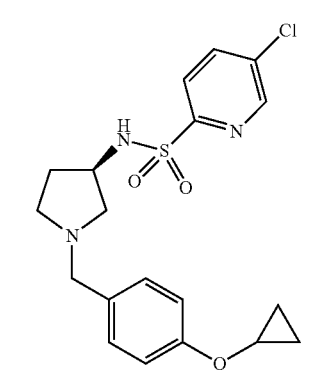 [SMILES: O=S(=O)(N[C@@H]1CCN(Cc2ccc(OC3CC3)cc2)C1)c1ccc(Cl)cn1] |
| 133 | 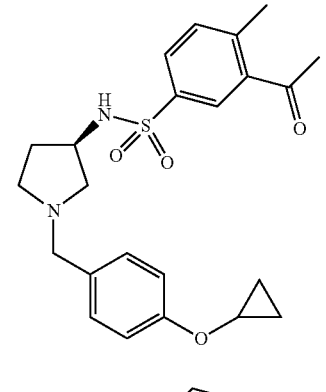 |
| 134 | 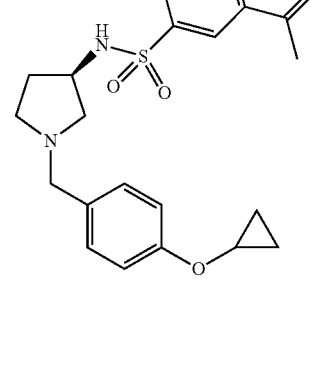 |

TABLE 1-continued
Gyramide compounds.
| No. | Structure |
|---|---|
| 135 | 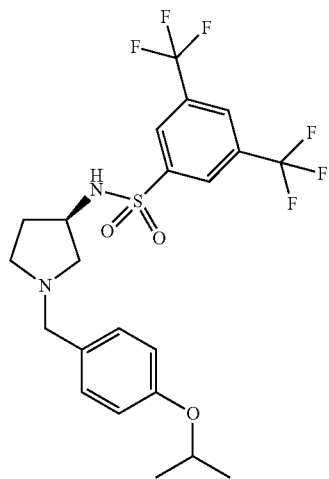 [SMILES: CC(C)Oc1ccc(CN2CC[C@@H](NS(=O)(=O)c3cc(C(F)(F)F)cc(C(F)(F)F)c3)C2)cc1] |
| 136 | 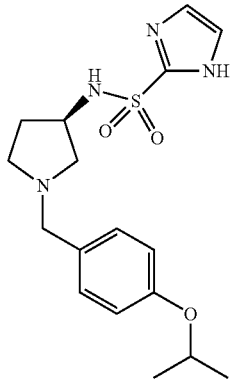 [SMILES: CC(C)Oc1ccc(CN2CC[C@@H](NS(=O)(=O)c3ncc[nH]3)C2)cc1] |
| 137 | 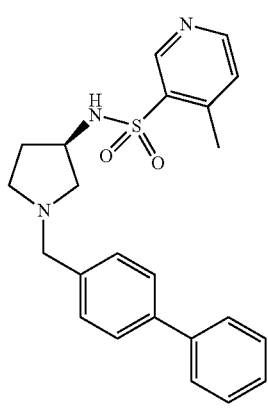 [SMILES: Cc1ccncc1S(=O)(=O)N[C@@H]1CCN(Cc2ccc(-c3ccccc3)cc2)C1] |
TABLE 1-continued
Gyramide compounds.
| No. | Structure |
|---|---|
| 138 | 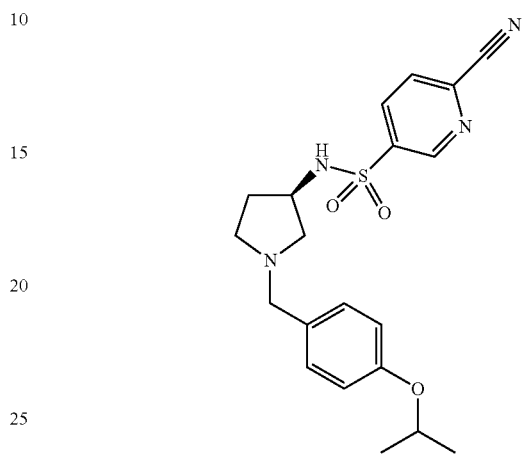 |
| 139 | 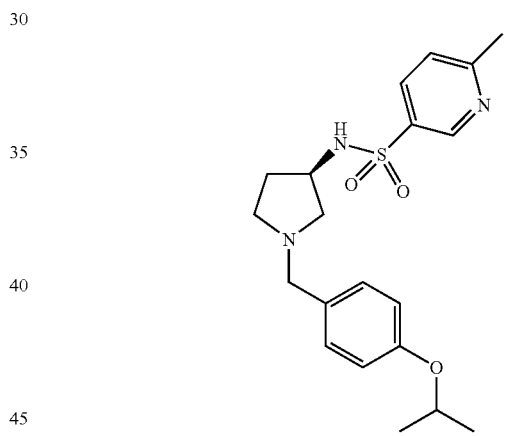 |
| 140 | 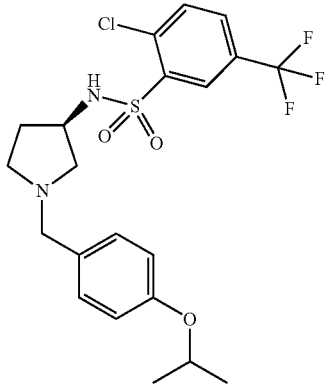 [SMILES: CC(C)Oc1ccc(CN2CC[C@@H](NS(=O)(=O)c3cc(C(F)(F)F)ccc3Cl)C2)cc1] |

TABLE 1-continued
Gyramide compounds.
| No. | Structure |
|---|---|
| 141 | 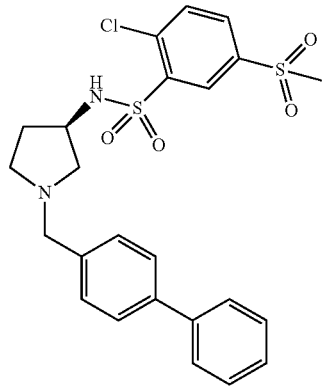 [SMILES: CS(=O)(=O)c1ccc(Cl)c(S(=O)(=O)N[C@@H]2CCN(Cc3ccc(-c4ccccc4)cc3)C2)c1] |
| 142 | 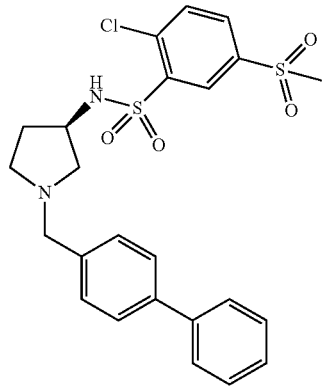 [SMILES: CS(=O)(=O)c1ccc(Cl)c(S(=O)(=O)N[C@@H]2CCN(Cc3ccc(-c4ccccc4)cc3)C2)c1] |
| 143 | 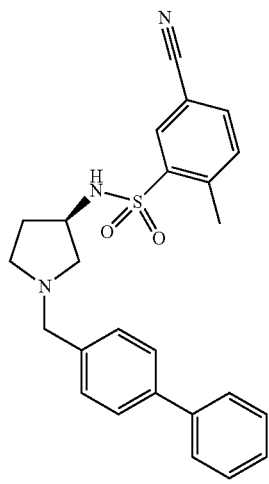 [SMILES: Cc1ccc(C#N)cc1S(=O)(=O)N[C@@H]1CCN(Cc2ccc(-c3ccccc3)cc2)C1] |
| 144 | 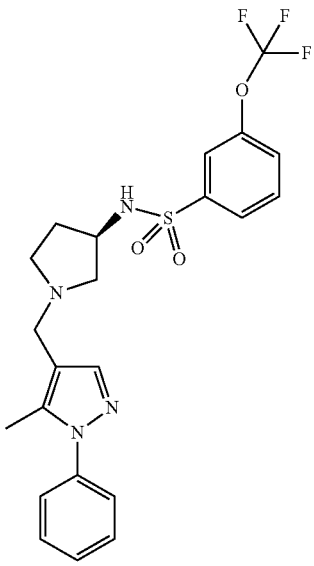 [SMILES: Cc1c(CN2CC[C@@H](NS(=O)(=O)c3cccc(OC(F)(F)F)c3)C2)cnn1-c1ccccc1] |
| 145 | 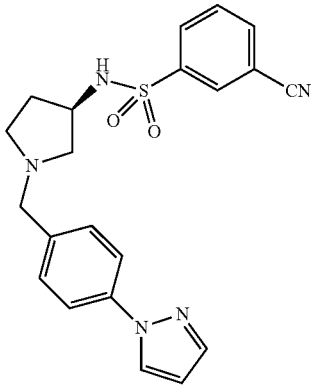 [SMILES: N#Cc1cccc(S(=O)(=O)N[C@@H]2CCN(Cc3ccc(-n4cccn4)cc3)C2)c1] |
| 146 | 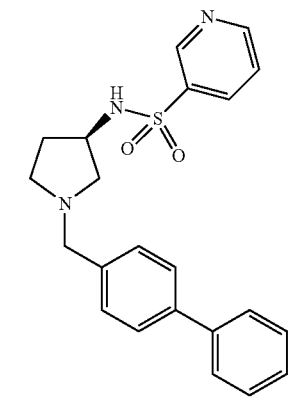 [SMILES: O=S(=O)(N[C@@H]1CCN(Cc2ccc(-c3ccccc3)cc2)C1)c1cccnc1] |

TABLE 1-continued
Gyramide compounds.
| No. | Structure |
|---|---|
| 147 | 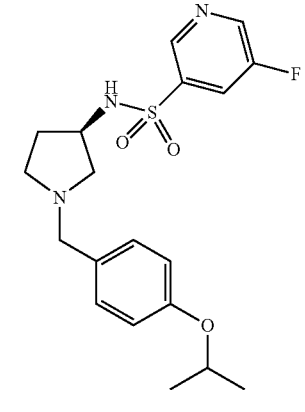 |
| 148 | 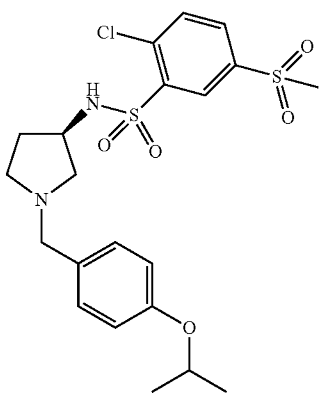 [SMILES: CC(C)Oc1ccc(CN2CC[C@@H](NS(=O)(=O)c3cc(S(C)(=O)=O)ccc3Cl)C2)cc1] |
| 149 | 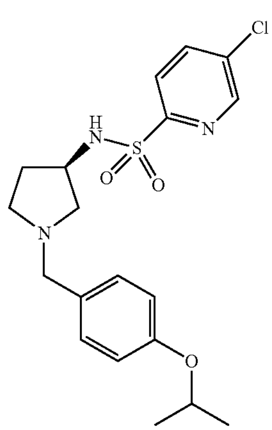 [SMILES: CC(C)Oc1ccc(CN2CC[C@@H](NS(=O)(=O)c3ccc(Cl)cn3)C2)cc1] |
TABLE 1-continued
Gyramide compounds.
| No. | Structure |
|---|---|
| 150 | 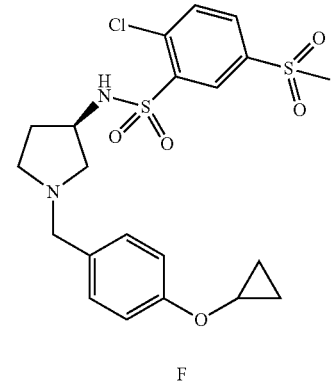 |
| 151 | 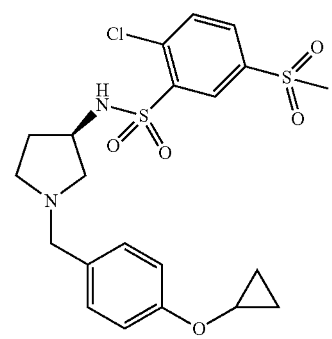 [SMILES: CS(=O)(=O)c1ccc(Cl)c(S(=O)(=O)N[C@@H]2CCN(Cc3ccc(OC4CC4)cc3)C2)c1] |
| 152 | 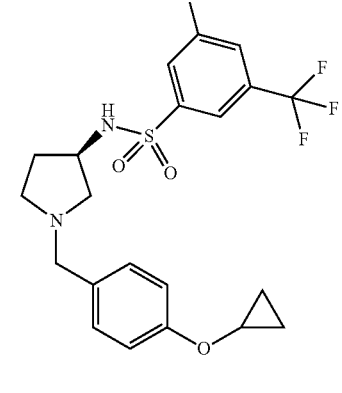 |
| 153 | 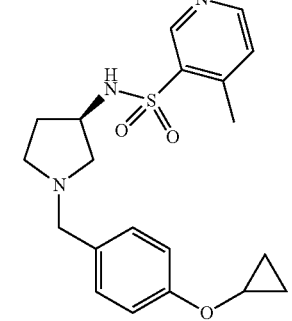 |

TABLE 1-continued

Gyramide compounds.

| No. | Structure |
|-----|-----------|
| 154 | 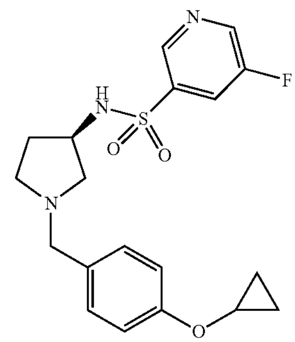 [SMILES: O=S(=O)(N[C@@H]1CCN(Cc2ccc(OC3CC3)cc2)C1)c1cncc(F)c1] |
| 155 | 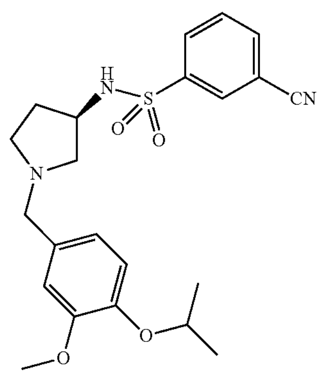 [SMILES: COc1cc(CN2CC[C@@H](NS(=O)(=O)c3cccc(C#N)c3)C2)ccc1OC(C)C] |
| 156 | 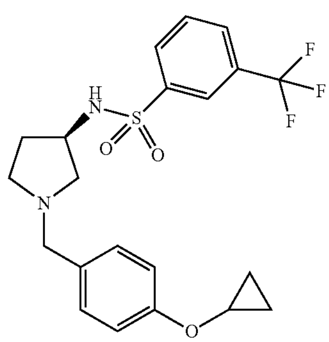 [SMILES: O=S(=O)(N[C@@H]1CCN(Cc2ccc(OC3CC3)cc2)C1)c1cccc(C(F)(F)F)c1] |
| 157 | 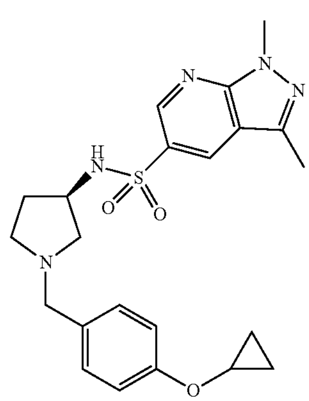 [SMILES: Cc1nn(C)c2ncc(S(=O)(=O)N[C@@H]3CCN(Cc4ccc(OC5CC5)cc4)C3)cc12] |
| 158 | |
| 159 | |
| 160 | |
| 161 | |

TABLE 1-continued

Gyramide compounds.

| No. | Structure |
|---|---|
| 162 | 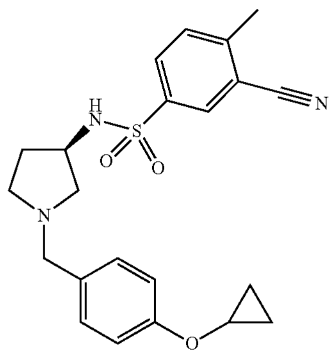 [SMILES: Cc1ccc(S(=O)(=O)N[C@@H]2CCN(Cc3ccc(OC4CC4)cc3)C2)cc1C#N] |
| 163 | 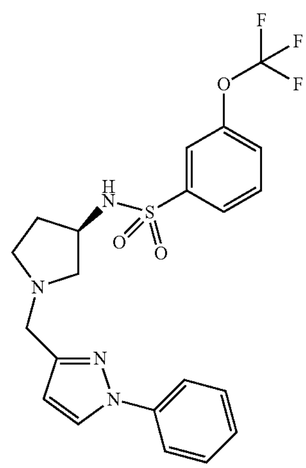 [SMILES: O=S(=O)(N[C@@H]1CCN(Cc2ccn(-c3ccccc3)n2)C1)c1cccc(OC(F)(F)F)c1] |
| 164 | 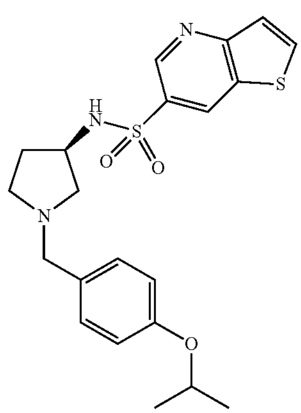 [SMILES: CC(C)Oc1ccc(CN2CC[C@@H](NS(=O)(=O)c3cnc4ccsc4c3)C2)cc1] |
| 165 | 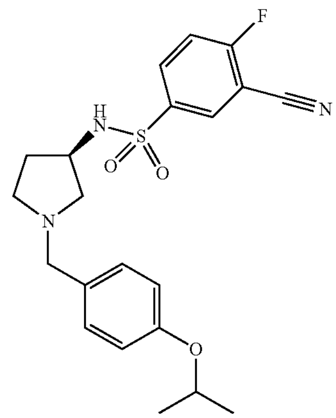 [SMILES: CC(C)Oc1ccc(CN2CC[C@@H](NS(=O)(=O)c3ccc(F)c(C#N)c3)C2)cc1] |
| 166 | 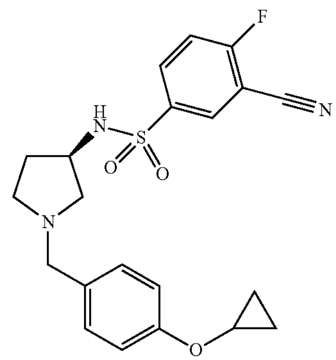 [SMILES: N#Cc1cc(S(=O)(=O)N[C@@H]2CCN(Cc3ccc(OC4CC4)cc3)C2)ccc1F] |
| 167 | 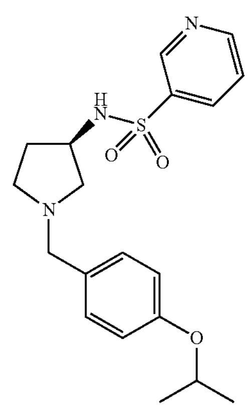 [SMILES: CC(C)Oc1ccc(CN2CC[C@@H](NS(=O)(=O)c3cccnc3)C2)cc1] |
| 168 | 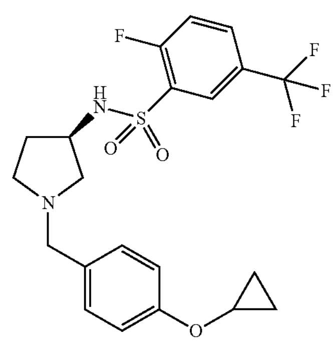 [SMILES: O=S(=O)(N[C@@H]1CCN(Cc2ccc(OC3CC3)cc2)C1)c1cc(C(F)(F)F)ccc1F] |

TABLE 1-continued
Gyramide compounds.
| No. | Structure |
|-----|-----------|
| 169 | 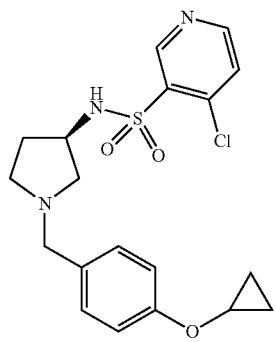 |
| 170 | 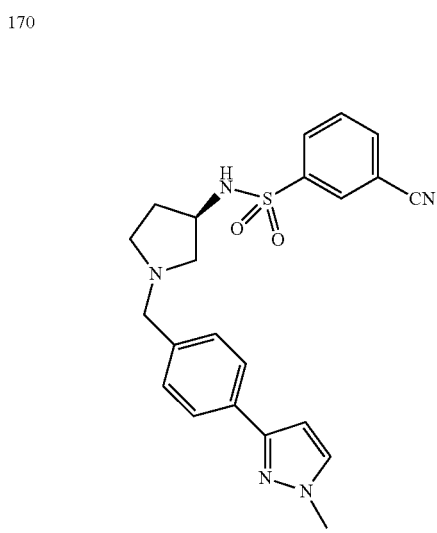 |
| 171 | 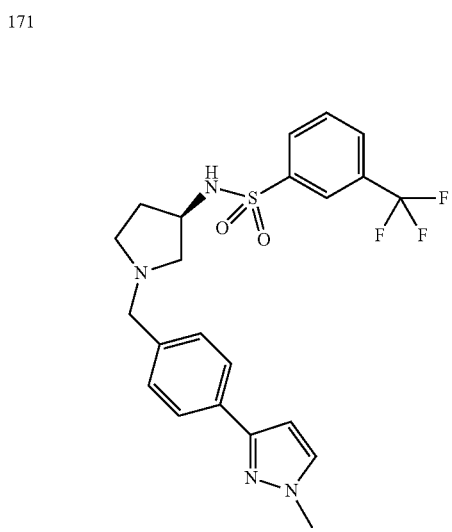 |"
TABLE 1-continued
Gyramide compounds.
| No. | Structure |
|-----|-----------|
| 172 | 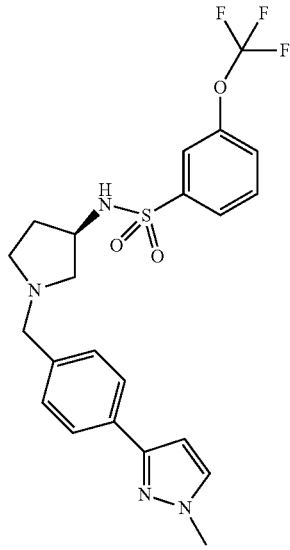 [SMILES: Cn1ccc(-c2ccc(CN3CC[C@@H](NS(=O)(=O)c4cccc(OC(F)(F)F)c4)C3)cc2)n1] |
| 173 | 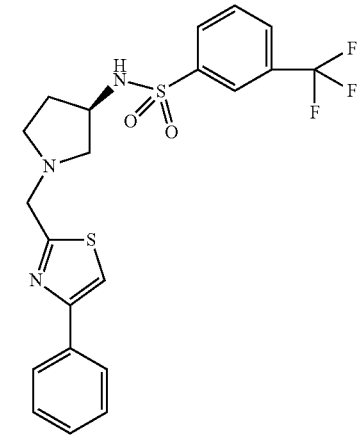 [SMILES: O=S(=O)(N[C@@H]1CCN(Cc2nc(-c3ccccc3)cs2)C1)c1cccc(C(F)(F)F)c1] |
| 174 | 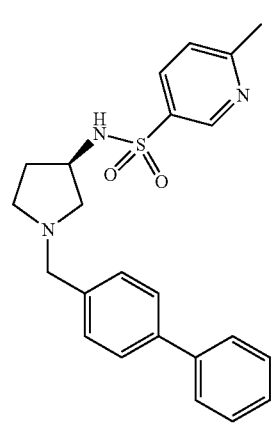 [SMILES: Cc1ccc(S(=O)(=O)N[C@@H]2CCN(Cc3ccc(-c4ccccc4)cc3)C2)cn1] |

TABLE 1-continued
Gyramide compounds.
| No. | Structure |
|---|---|
| 175 | 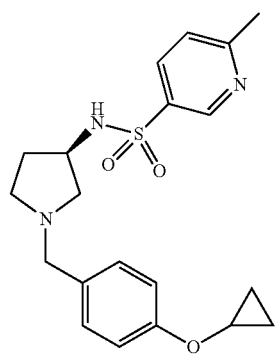 [SMILES: Cc1ccc(S(=O)(=O)N[C@@H]2CCN(Cc3ccc(OC4CC4)cc3)C2)cn1] |
| 176 | 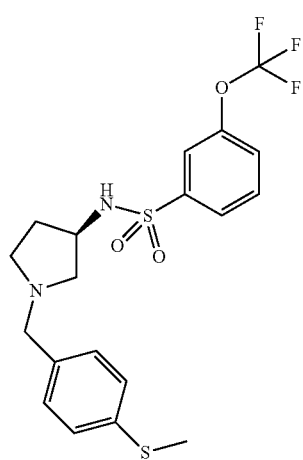 [SMILES: CSc1ccc(CN2CC[C@@H](NS(=O)(=O)c3cccc(OC(F)(F)F)c3)C2)cc1] |
| 177 | 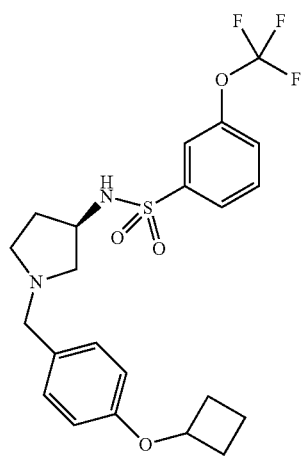 [SMILES: O=S(=O)(N[C@@H]1CCN(Cc2ccc(OC3CCC3)cc2)C1)c1cccc(OC(F)(F)F)c1] |
| 178 | 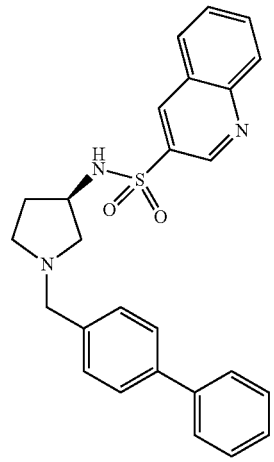 [SMILES: O=S(=O)(N[C@@H]1CCN(Cc2ccc(-c3ccccc3)cc2)C1)c1cnc2ccccc2c1] |
| 179 | 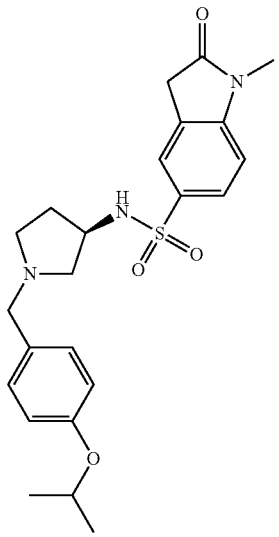 [SMILES: CC(C)Oc1ccc(CN2CC[C@@H](NS(=O)(=O)c3ccc4c(c3)CC(=O)N4C)C2)cc1] |
| 180 | 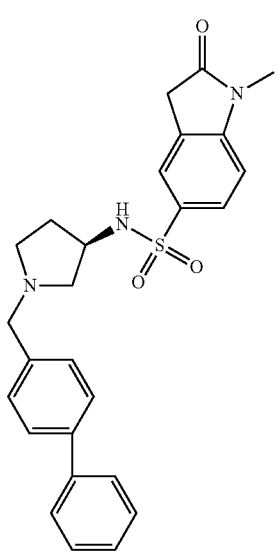 [SMILES: CN1C(=O)Cc2cc(S(=O)(=O)N[C@@H]3CCN(Cc4ccc(-c5ccccc5)cc4)C3)ccc21] |

TABLE 1-continued

Gyramide compounds.

| No. | Structure |
|---|---|
| 181 | (structure) |
| 182 | (structure) |
| 183 | (structure) |

In some embodiments, the invention provides a compound selected from:

(structures)

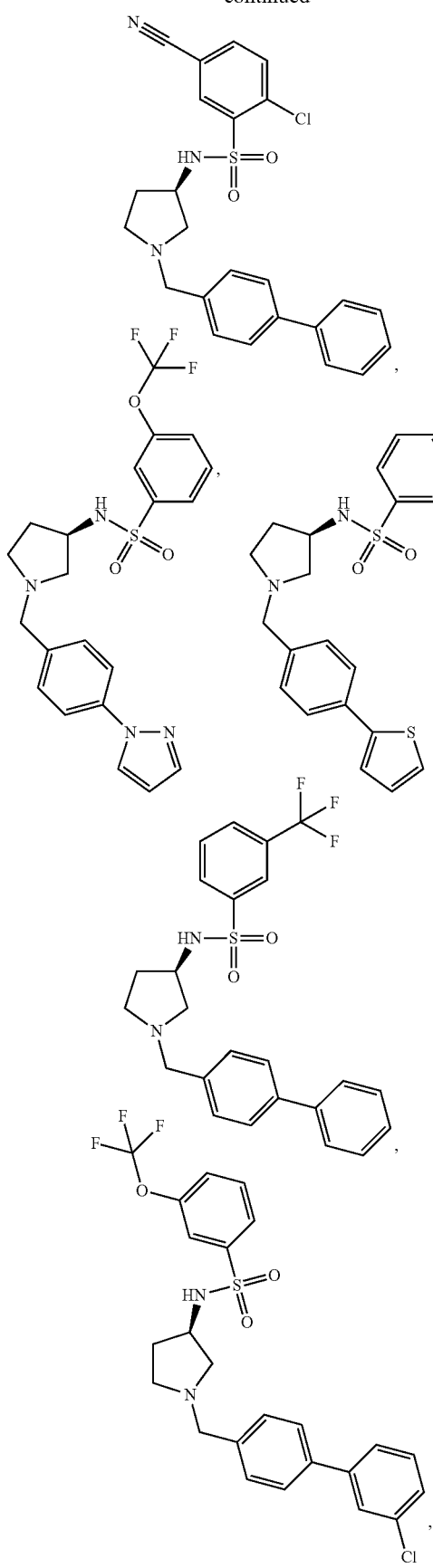
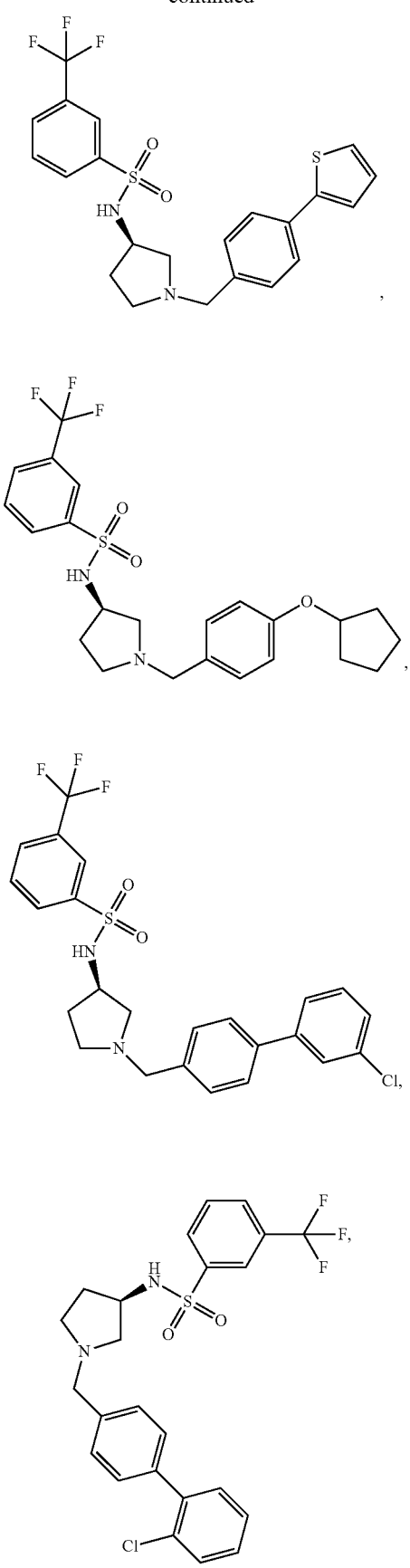

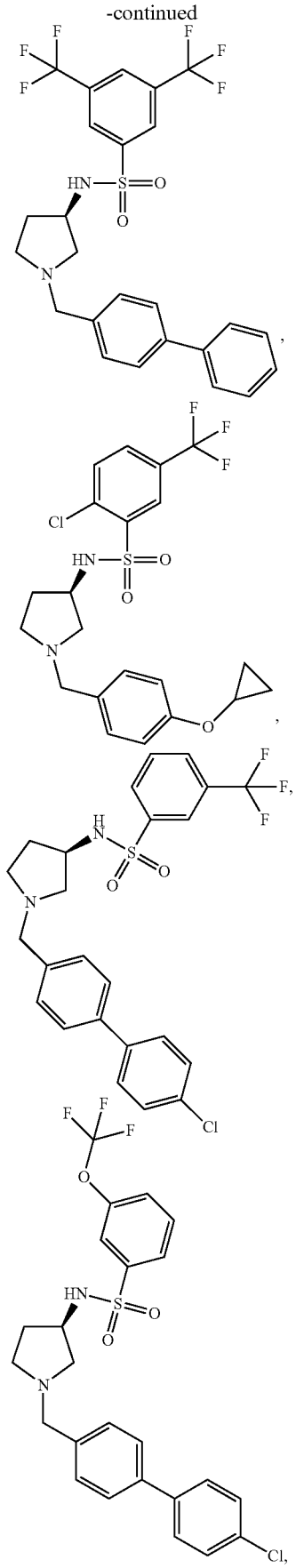
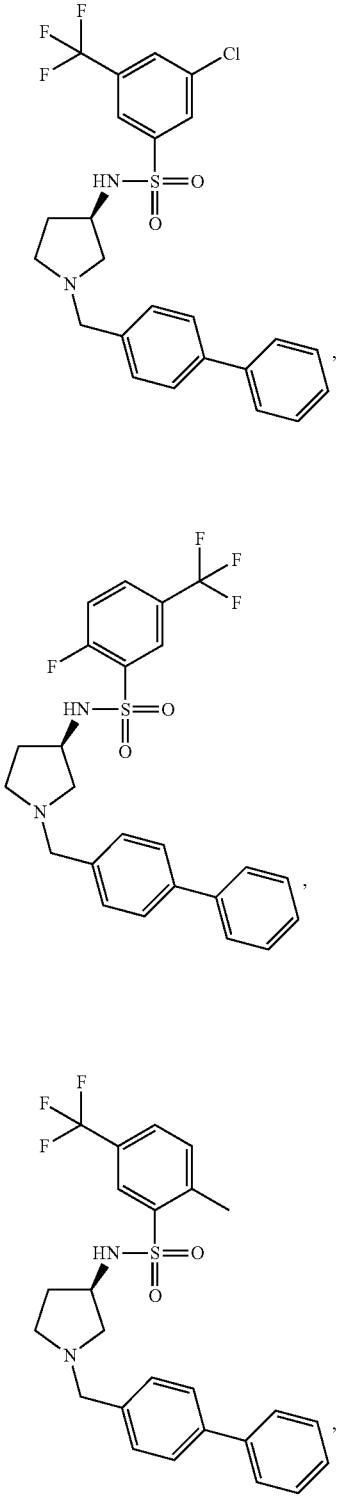
or a pharmaceutically acceptable salt thereof.
In some embodiments, the invention provides a compound selected from:

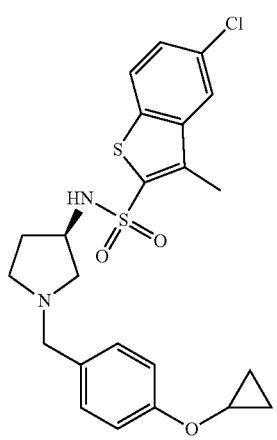
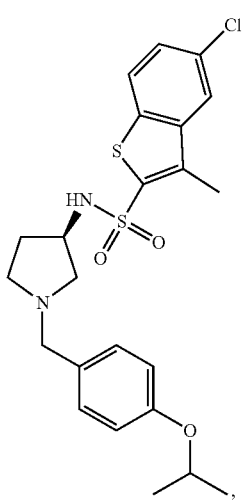
or a pharmaceutically acceptable salt thereof.
In some embodiments, the invention provides a compound selected from:
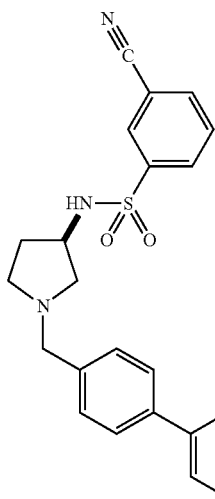
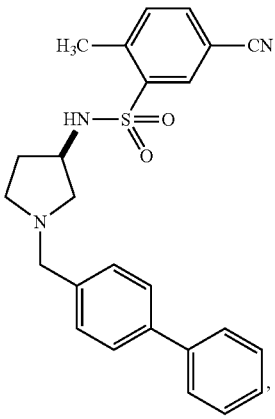
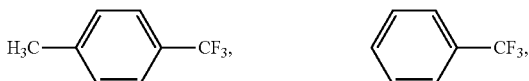
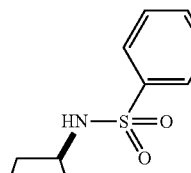
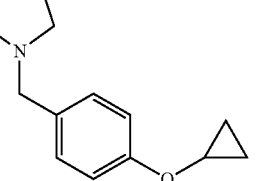
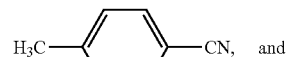
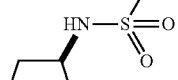
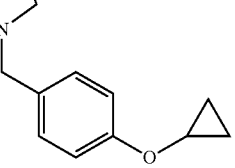
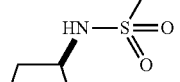
or a pharmaceutically acceptable salt thereof.
In some embodiments, the invention provides a compound selected from:
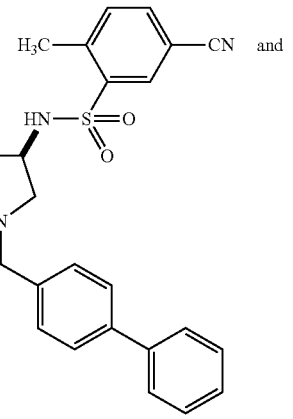

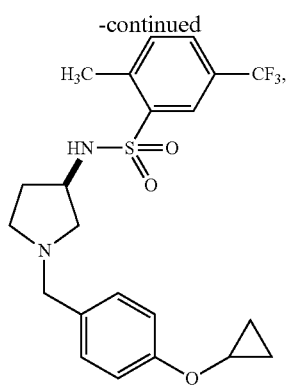

or a pharmaceutically acceptable salt thereof.

In certain embodiments, the present application sets forth a compound having the following structure:

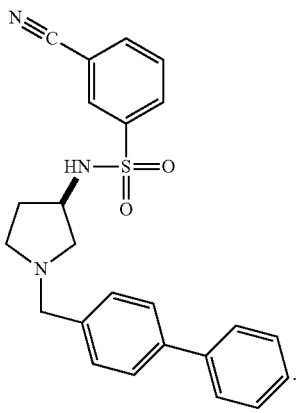

In some of the above embodiments, the invention further provides a pharmaceutical composition comprising a compound having any one of the structures selected from Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI, and a pharmaceutically acceptable excipient.

In some other embodiments, the invention provides a composition comprising a compound having any one of the structures selected from Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI and a second antibiotic.

In some other embodiments, the invention provides a composition comprising one or more of the compounds listed in Table 1 and a second antibiotic.

In some of the compositions described above, the second antibiotic is an erythromycin class (macrolide) antibiotic.

In certain compositions described above, the antibiotic is selected from ansamycin, azithromycin (ZITHROMAX/ZITROMAX/SUMAMED), carbomycin (Magnamycin), cethromycin, clarithromycin (BIAXIN), dirithromycin (Dynabac), erythromycin, erythromycin ethylsuccinate, mitemcinal, oleandomycin (Sigmamycine), roxithromycin (RULID/SURLID/ROXID), spiramycin (Rovamycine), telithromycin (KETEK), or tylocine.

In certain other compositions described above, the antibiotic is selected from a gyrase inhibitor, a β-lactam antibiotic, an FDA-approved antibiotic, a penicillin, a cephalosporin, a polymyxin, a rifamycin, a lipiarmycin, a quinolone antibiotic, a fluoroquinolone antibiotic, a sulfonamide antibiotic, a macrolide, a lincosamide and a tetracycline, an antibiotic specific for targeting Gram-negative bacteria, an antibiotic specific for targeting a Gram-positive bacteria, a cyclic lipopeptide (e.g., daptomycin), a glycylcycline (e.g., tigecycline), an oxazolidinone (e.g., linezolid), or a lipiarmycin (e.g., fidaxomicin).

In some other embodiments, the invention provides compositions that include a compound having a structure selected from Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI; an efflux inhibitor, and optionally a pharmaceutically acceptable excipient.

In some embodiments, the invention provides compositions that include a one or more of the compounds listed in Table 1; an efflux inhibitor, and optionally a pharmaceutically acceptable excipient.

IV. Compound Preparation

Compounds provided herein can be prepared by the methods described in the Examples, or in a component assembly fashion as outlined in the synthetic schemes of FIG. 1. Briefly, a Boc-protected 3-amino pyrrolidine can be combined with a suitable (aromatic)aldehyde and a reducing agent such as NaB(OAc)₃ to provide the 'benzyl substituted' pyrrolidine framework shown. Removal of the Boc protecting group, followed by sulfonamide formation (using a suitable sulfonyl chloride) provides selected compounds of the invention. A synthetic approach in which the sulfonamide formation step and the aldehyde condensation steps are reversed is also shown (beginning with the analogous protected pyrrolidine) in the lower scheme of FIG. 1.

V. Compounds not Embraced by the Claimed Invention

The following compounds are not included in the claimed compounds:

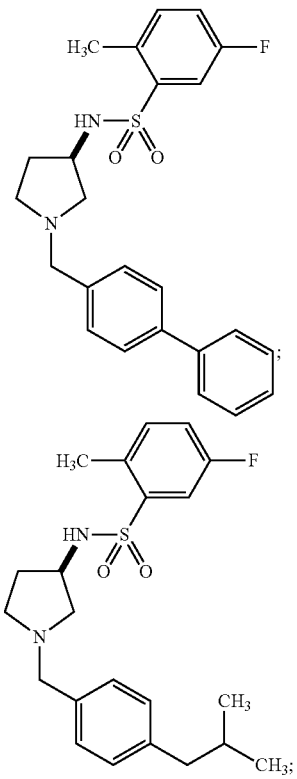

101
-continued

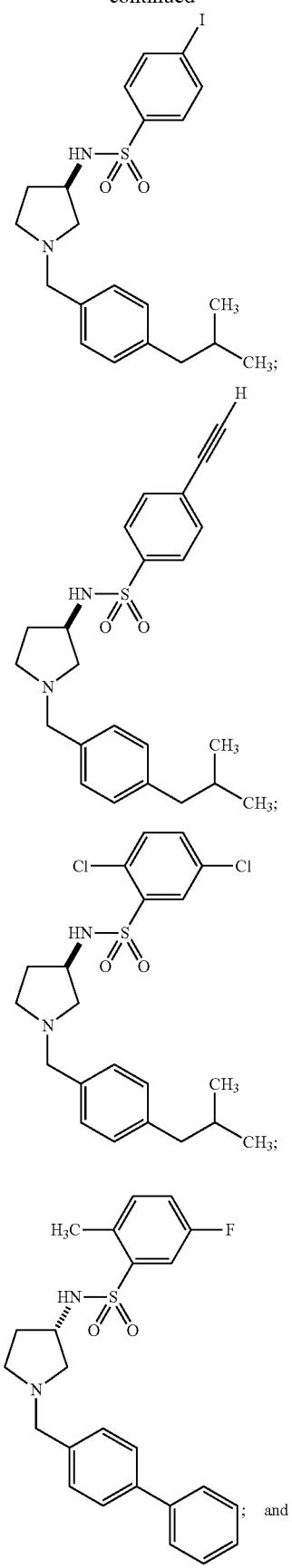

102
-continued

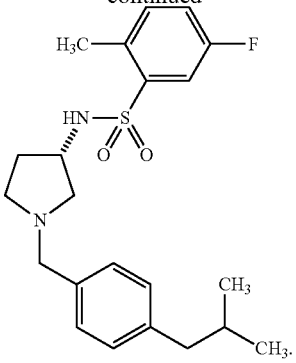

and

VI. Pharmaceutical Compositions and Administration

In another aspect, the invention provides compositions including an effective amount of a compound described herein and a pharmaceutically acceptable excipient. A pharmaceutical composition may optionally contain other therapeutic ingredients. Such compositions are suitable for pharmaceutical use in an animal or human.

A pharmaceutical composition or medicament of the present invention comprises (i) an effective amount of a compound described herein, and (ii) optionally a second antibiotic agent, described herein, or combinations thereof. Therapeutic agents may be used individually, sequentially, or in combination with one or more other such therapeutic agents (e.g., a first therapeutic agent, a second therapeutic agent, and a compound of the present invention).

Pharmaceutical compositions of the present invention can be formulated by standard techniques, including any of the methods well-known in the art. In general, the compounds of the present invention are combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein. Suitable pharmaceutical carriers are described herein and in *Remington: The Science and Practice of Pharmacy,* 21$^{st}$ Ed., University of the Sciences in Philadelphia, Lippencott Williams & Wilkins (2005). Preferred pharmaceutical carriers depend upon the intended mode of administration of the active agent. In some embodiments, the composition is formulated for oral administration or intravenous administration and includes a compound described herein and at least one member selected from the group consisting of an aqueous solution and a buffer solution.

Pharmaceutically acceptable carriers suitable for use with the present invention include any of the standard pharmaceutical carriers, buffers and excipients, including phosphate-buffered saline solution, water, and emulsions (such as an oil/water or water/oil emulsion), and various types of wetting agents and/or adjuvants.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral or rectal is also contemplated.

Suitable formulations for transdermal application, e.g., treatment of localized infection on the exterior of a subject's skin, include an effective amount of a compound or composition described herein optionally with a carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. The invention provides tablets and gelatin capsules comprising a compound or composition described herein, alone or in combination with a second antibiotic, or a dried solid powder of these drugs, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

The compositions and formulations set forth herein can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, or about 1 to 50%, of the active ingredient.

For administration by inhalation, the compositions of the present invention may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compositions set forth herein can also be formulated in rectal compositions, for example, suppositories or retention enemas, for example, containing conventional suppository bases, for example, cocoa butter or other glycerides.

In some embodiments, the invention provides compositions further including a pharmaceutical surfactant. In some embodiments, the invention provides compositions further including a cryoprotectant. In some embodiments, the cryoprotectant is selected from the group consisting of glucose, sucrose, trehalose, lactose, sodium glutamate, PVP, HPβCD, CD, glycerol, maltose, mannitol, and saccharose.

Controlled release parenteral formulations of the compositions of the present invention can be made as implants, oily injections, or as particulate systems. For a broad overview of delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles.

Polymers can be used for ion-controlled release of compositions of the present invention. Various degradable and nondegradable polymeric matrices for use in controlled drug delivery are known in the art (Langer R., Accounts Chem. Res., 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin 2 and urease (Johnston et al., Pharm. Res., 9:425-434 (1992); and Pec et al., J. Parent. Sci. Tech., 44(2):58 65 (1990)). Alternatively, hydroxyapatite has been used as a microcarrier for controlled release of proteins (Ijntema et al., Int. J. Pharm., 112:215-224 (1994)). In yet another aspect, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Furthermore, the active ingredient can be formulated as a depot preparation. Such long-acting formulations can be administered by implantation (for example, subcutaneously or intramuscularly) or by intramuscular injection. Thus, for example, the a compound or composition described herein can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions or medicaments can be administered to a subject at a therapeutically effective dose to prevent, treat, or control a disease or condition (e.g., a bacterial infection) as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular formulation in a particular subject. A unit dosage for oral administration to a mammal of about 50 to 70 kg may contain between about 5 and 500 mg of the active ingredient. Typically, a dosage of the active compounds of the present invention is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents described herein may be administered for multiple days at the therapeutically effective daily dose. Thus, therapeutically effective administration of compounds to treat a disease or condition in a subject may require periodic (e.g., daily) administration that continues for a period ranging from three days to two weeks or longer. Compositions set forth herein may be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compositions including a compound or composition described herein may vary depending on the relative potency of the administered composition and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

In some embodiments, the methods include sequentially administering a compound or composition described herein following by a member selected from an antibiotic described herein.

In some embodiments of the present invention, a pharmaceutical composition or medicament is administered to a patient at a therapeutically effective dose to prevent, treat, or control a disease or condition set forth herein. The pharmaceutical composition or medicament is administered to a patient in an amount sufficient to elicit an effective therapeutic or diagnostic response in the patient. An effective therapeutic or diagnostic response is, for example, a response that at least partially arrests or slows the symptoms or complications of a disease or condition set forth herein. An amount adequate to accomplish this is defined as "therapeutically effective dose."

The dosage of a compound or composition described herein is dependent on the species of warm-blooded animal (mammal), the body weight, age, individual condition, and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the compound of the present invention, is a dosage that is sufficient to achieve the desired effect.

Optimal dosing schedules can be calculated from measurements of active ingredient accumulation in the body of a subject. In general, dosage is from 1 ng to 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of a compound or composition described herein to a human being following established protocols known in the art and the disclosure herein.

Optimum dosages, toxicity, and therapeutic efficacy of compositions may vary depending on the relative potency of individual compositions and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g., rodents and monkeys) can be used to formulate a dosage range for use in humans. The dosage of compounds of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of DNA gyrase activity) as determined in cell culture. Such information can be used to more accurately determine useful doses in humans. Levels in plasma can be measured, for example, by high performance liquid chromatography (HPLC). In general, the dose equivalent of a composition containing a compound of the invention is from about 1 ng/kg to 100 mg/kg for a typical subject.

A typical composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as *Remington: The Science and Practice of Pharmacy*, 21$^{st}$ Ed., University of the Sciences in Philadelphia, Lippencott Williams & Wilkins (2005).

Exemplary doses of the compositions described herein, include milligram or microgram amounts of the composition per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a composition depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In one embodiment of the present invention, a pharmaceutical composition or medicament, described herein, is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Determination of an effective amount is well within the capability of those skilled in the art, especially in light of the detailed disclosure provided herein. Generally, an efficacious or effective amount of an composition is determined by first administering a low dose or small amount of the composition, and then incrementally increasing the administered dose or dosages, adding a second or third medication as needed, until a desired effect of is observed in the treated subject with minimal or no toxic side effects.

Single or multiple administrations of the compositions are administered depending on the dosage and frequency as required and tolerated by the patient. In any event, the composition should provide a sufficient quantity of the compositions of this invention to effectively treat the patient. Generally, the dose is sufficient to treat or ameliorate symptoms or signs of disease without producing unacceptable toxicity to the patient.

Dosages contemplated herein include those that include a compound or composition set forth herein.

VII. Methods of Using Compounds of the Invention

In another aspect, the present invention provides a method of killing bacteria, wherein the method includes contacting the bacteria with a compound having a structure selected from Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI.

In some embodiments, the method includes contacting the bacteria with a compound having structure Ia. In certain other embodiments, the method includes contacting the bacteria with a compound having structure Ib. In other embodiments, the method includes contacting the bacteria with a compound having structure Ic. In certain embodiments, the method includes contacting the bacteria with a compound having structure Id. In some embodiments, the method includes contacting the bacteria with a compound having structure Ie.

In yet certain other embodiments, the method includes contacting the bacteria with a compound having structure II. In some embodiments, the method includes contacting the bacteria with a compound having structure IIIa. In other embodiments, the method includes contacting the bacteria with a compound having structure IIIb. In certain embodiments, the method includes contacting the bacteria with a compound having structure IIIc. In some embodiments, the method includes contacting the bacteria with a compound having structure IIId. In some other embodiments, the method includes contacting the bacteria with a compound having structure IIIe. In certain embodiments, the method includes contacting the bacteria with a compound having structure IIIf. In some embodiments, the method includes contacting the bacteria with a compound having structure IIIg. In other embodiments, the method includes contacting the bacteria with a compound having structure IIIh. In certain other embodiments, the method includes contacting the bacteria with a compound having structure IIIi.

In some embodiments, the method includes contacting the bacteria with a compound having structure Iva. In certain embodiments, the method includes contacting the bacteria with a compound having structure IVb. In some embodiments, the method includes contacting the bacteria with a compound having structure IVc. In certain embodiments, the method includes contacting the bacteria with a compound having structure IVd. In certain embodiments, the method includes contacting the bacteria with a compound having structure IVe. In other embodiments, the method includes contacting the bacteria with a compound having structure Va. In certain embodiments, the method includes contacting the bacteria with a compound having structure Vb. In some embodiments, the method includes contacting the bacteria with a compound having structure Vc. In some other embodiments, the method includes contacting the bacteria with a compound having structure Vd. In yet other embodiments, the method includes contacting the bacteria with a compound having structure, or VI.

In some embodiments, the method of killing bacteria includes contacting the bacteria with a compound selected from:

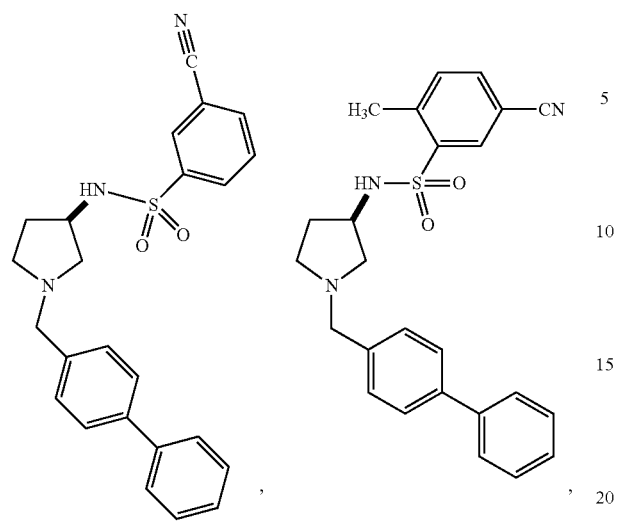
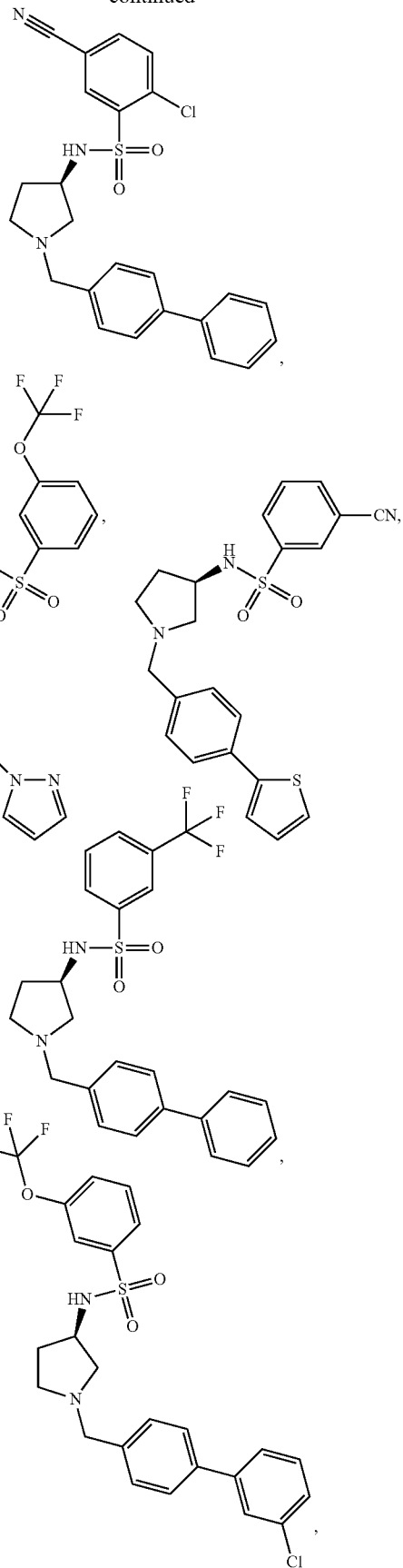

111
-continued
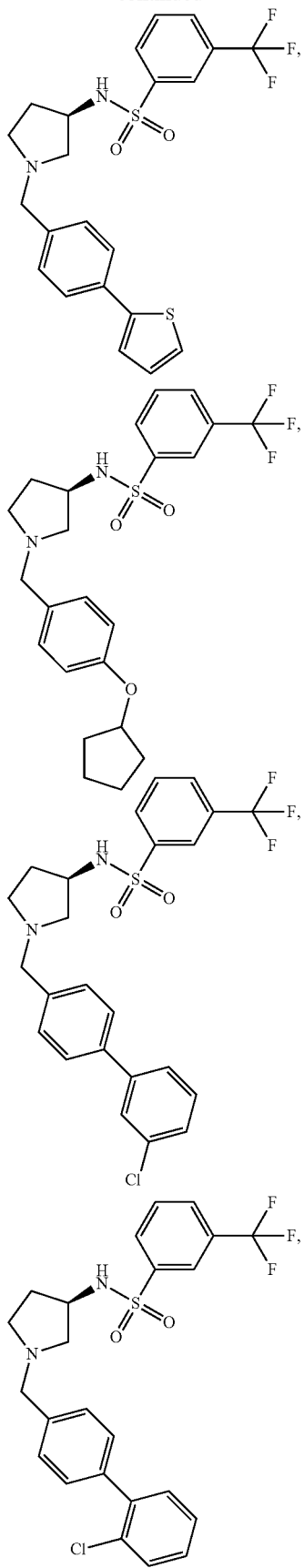
112
-continued
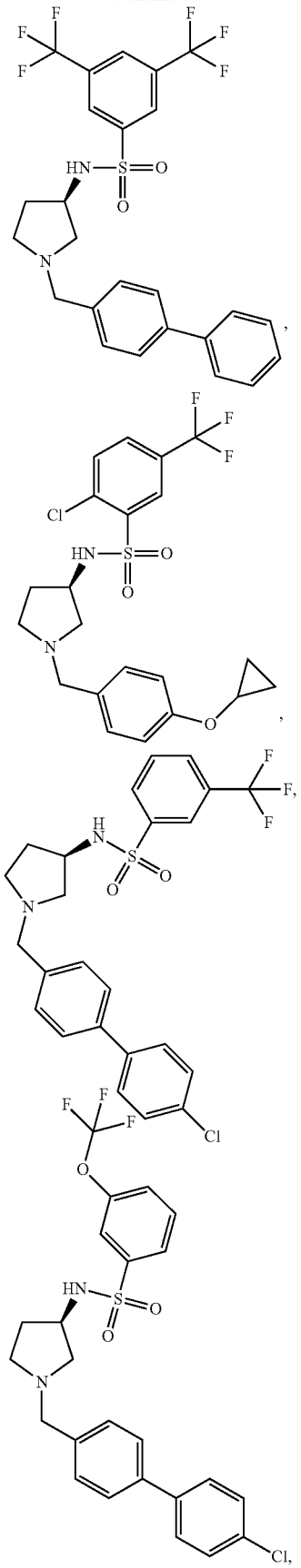

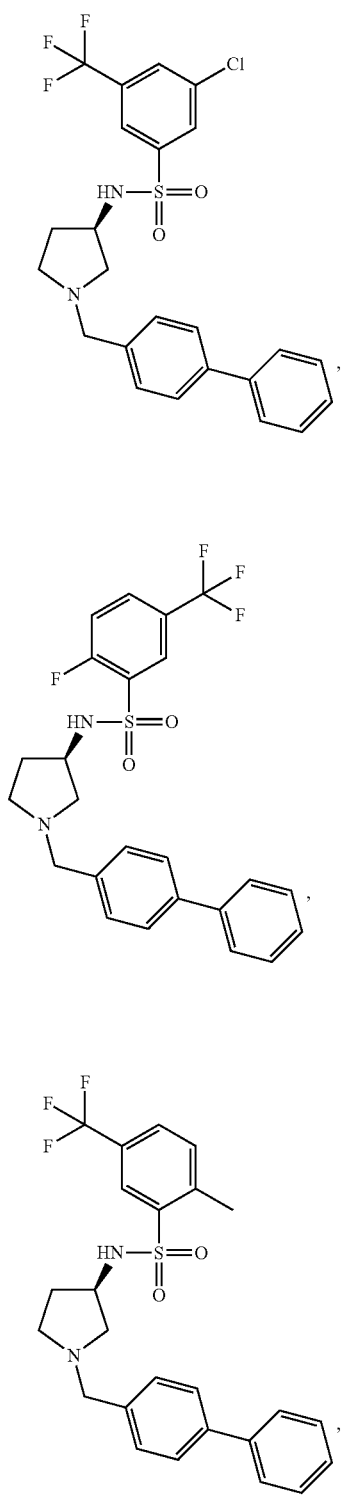
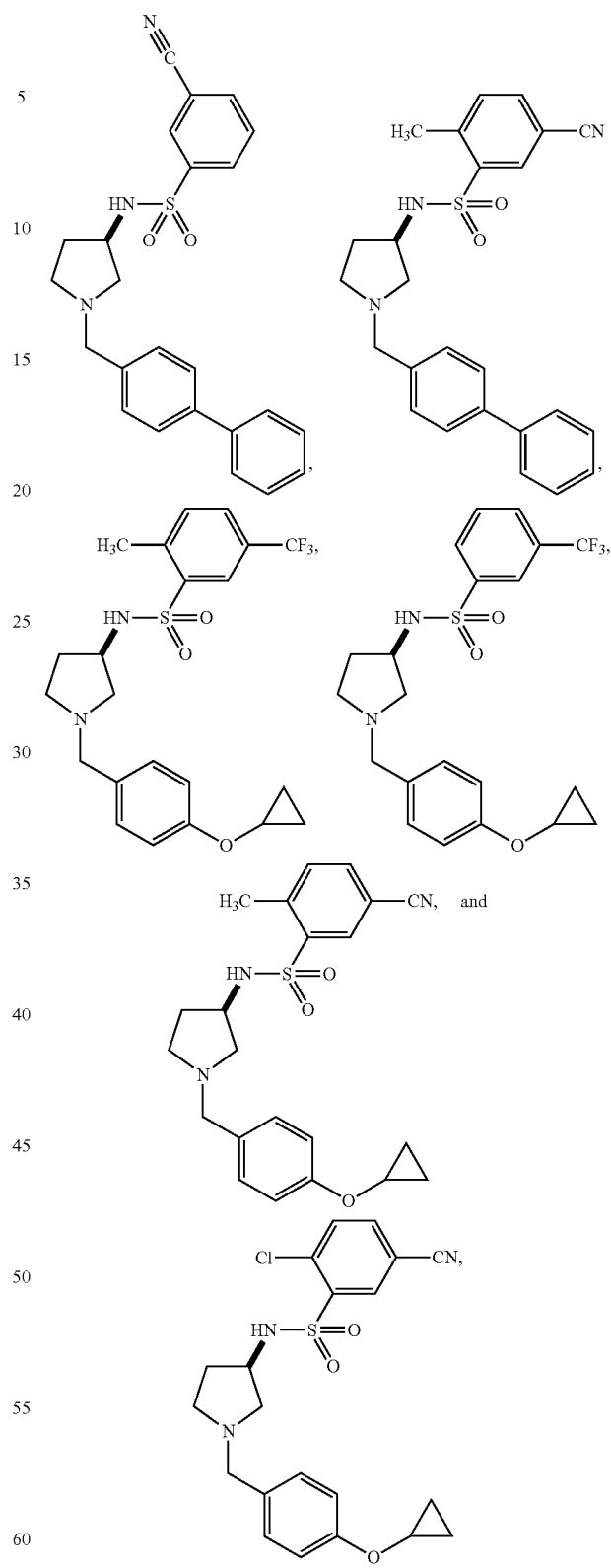
or a pharmaceutically acceptable salt thereof.
In some embodiments, the method of killing bacteria includes contacting the bacteria with a compound selected from:
or a pharmaceutically acceptable salt thereof.
In any of the above methods, the methods may include contacting the bacteria with a compound or composition set forth above.

In some of the methods set forth herein, the bacteria are Gram-negative bacteria. In some embodiments, the bacteria are Gram-positive bacteria.

In some other methods which are set forth herein, the bacteria are *Escherichia coli, Enterococcus faecium, Salmonella enterica, Staphylococcus aureus, Streptococcus pneumonia, Klebsiella pneumoniae, Acinetobacter baumannii, Pseudomonas aeruginosa*, or *Enterobacter* species.

In certain embodiments, the invention provides methods wherein the bacteria are resistant to vancomycin. In other embodiments, the bacteria are resistant to fluoroquinolone antibiotics.

In a related aspect, the invention provides a method of inhibiting bacterial growth, wherein the method includes contacting a bacteria set forth in this application with a compound having a structure selected from Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI. In certain embodiments, the method includes contacting the bacteria with a compound having structure Ia. In certain other embodiments, the method includes contacting the bacteria with a compound having structure Ib. In other embodiments, the method includes contacting the bacteria with a compound having structure Ic. In certain embodiments, the method includes contacting the bacteria with a compound having structure Id. In certain other embodiments, the method includes contacting the bacteria with a compound having structure Ie.

In some embodiments, the method includes contacting the bacteria with a compound having structure II. In some embodiments, the method includes contacting the bacteria with a compound having structure IIIa. In other embodiments, the method includes contacting the bacteria with a compound having structure IIIb. In certain embodiments, the method includes contacting the bacteria with a compound having structure IIIc. In some embodiments, the method includes contacting the bacteria with a compound having structure IIId. In some other embodiments, the method includes contacting the bacteria with a compound having structure IIIe. In certain embodiments, the method includes contacting the bacteria with a compound having structure IIIf. In some embodiments, the method includes contacting the bacteria with a compound having structure IIIg. In other embodiments, the method includes contacting the bacteria with a compound having structure IIIh. In certain other embodiments, the method includes contacting the bacteria with a compound having structure IIIi.

In some embodiments, the method includes contacting the bacteria with a compound having structure IVa. In certain embodiments, the method includes contacting the bacteria with a compound having structure IVb. In some embodiments, the method includes contacting the bacteria with a compound having structure IVc. In certain embodiments, the method includes contacting the bacteria with a compound having structure IVd. In other embodiments, the method includes contacting the bacteria with a compound having structure Va. In certain embodiments, the method includes contacting the bacteria with a compound having structure Vb. In some embodiments, the method includes contacting the bacteria with a compound having structure Vc. In some other embodiments, the method includes contacting the bacteria with a compound having structure Vd. In certain embodiments, the method includes contacting the bacteria with a compound having structure IVe. In yet other embodiments, the method includes contacting the bacteria with a compound having structure VI.

In some embodiments, the methods include bacteria that are Gram-negative bacteria. In some other of the above embodiments, the methods include bacteria that are Gram-positive bacteria. In certain other embodiments, the methods of inhibiting bacterial growth include bacteria selected from *Escherichia coli, Enterococcus faecium, Salmonella enterica, Staphylococcus aureus, Streptococcus pneumonia, Klebsiella pneumoniae, Acinetobacter baumannii, Pseudomonas aeruginosa*, or *Enterobacter* species. In certain embodiments, the bacteria are resistant to vancomycin. In yet other embodiments, the methods of inhibiting bacterial growth include bacteria that are resistant to fluoroquinolone antibiotics.

In some embodiments, the invention provides a method of inhibiting bacterial growth, wherein the method includes contacting the bacteria with a compound having structure Ia, Ib, Ic, Id, or Ie.

In some embodiments, the invention provides a method of inhibiting bacterial growth, wherein the method includes contacting the bacteria with a compound having a structure selected from Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI.

In some embodiments, the method of inhibiting bacterial growth includes contacting the bacteria with a compound selected from:

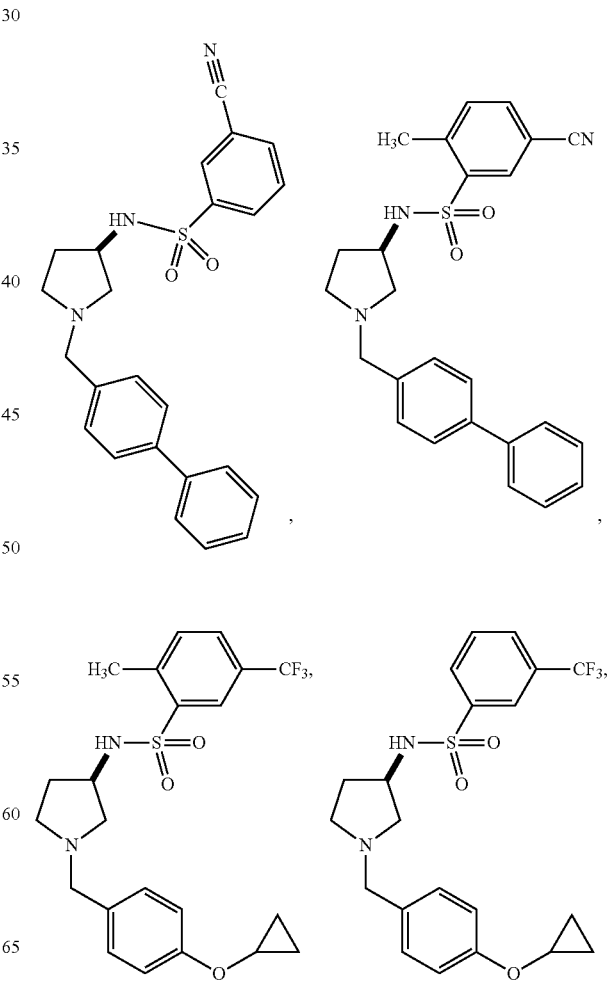

117
-continued
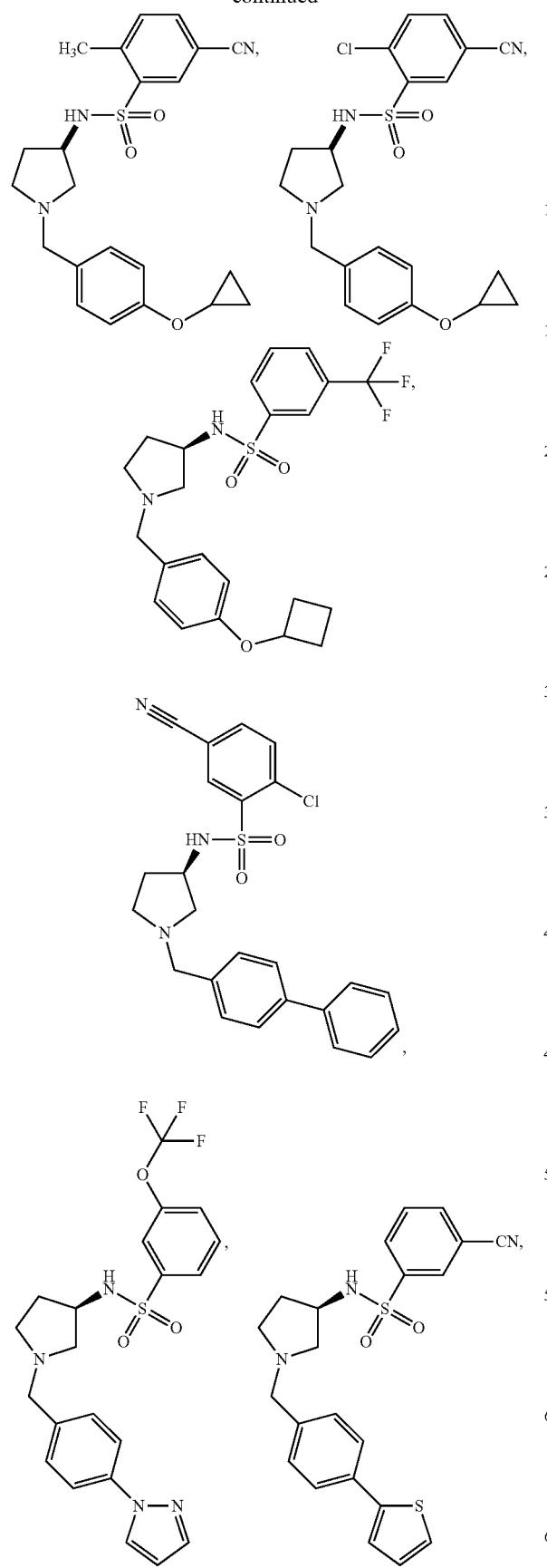
118
-continued
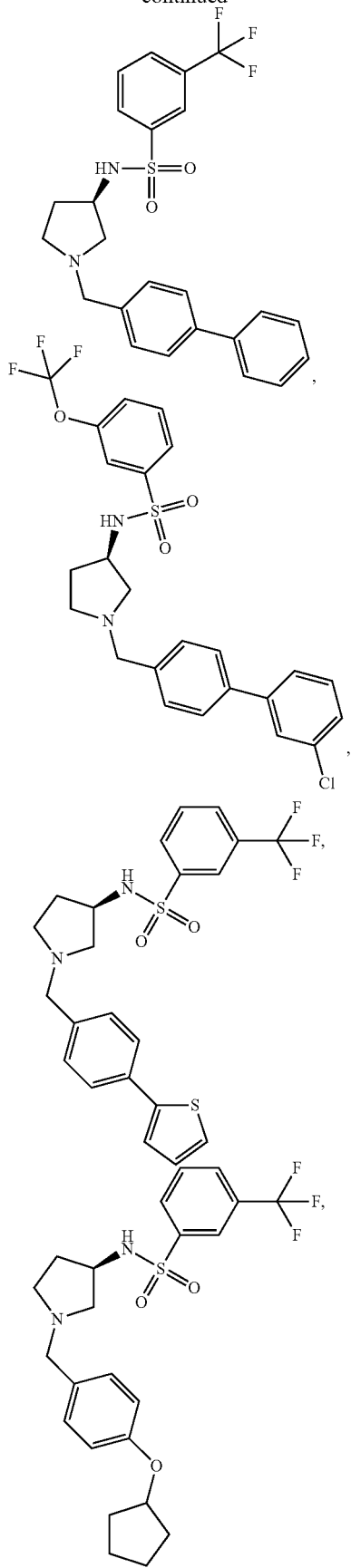

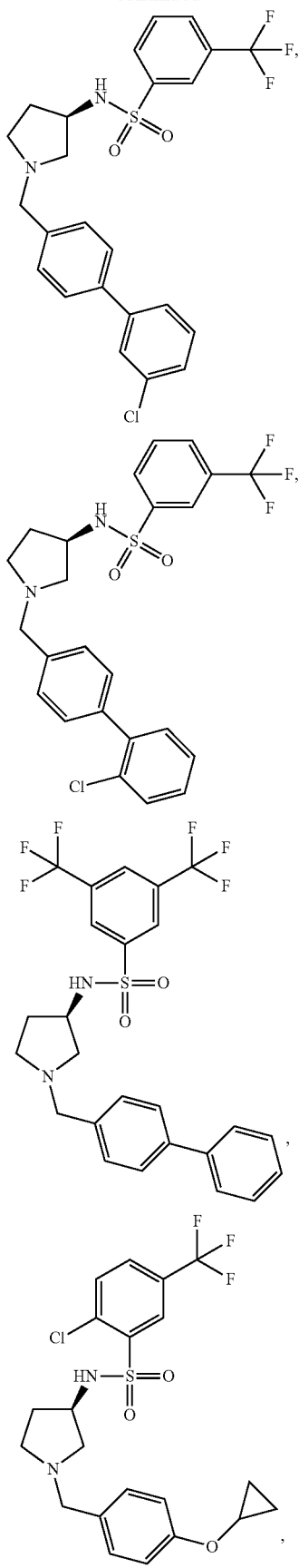

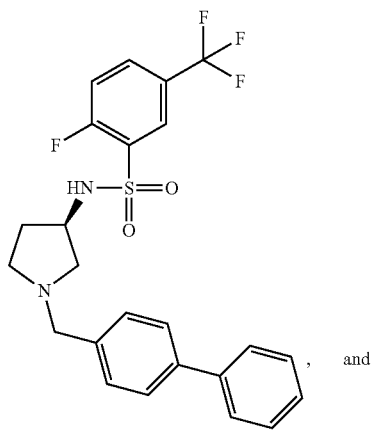

, and

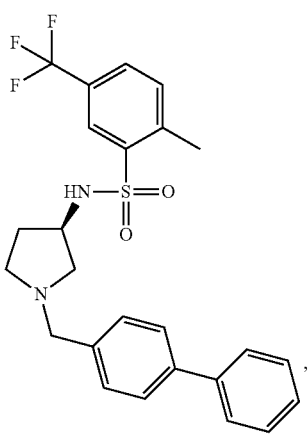

, or a pharmaceutically acceptable salt thereof.

In some embodiments, the method of inhibiting bacterial growth includes contacting the bacteria with a compound selected from:

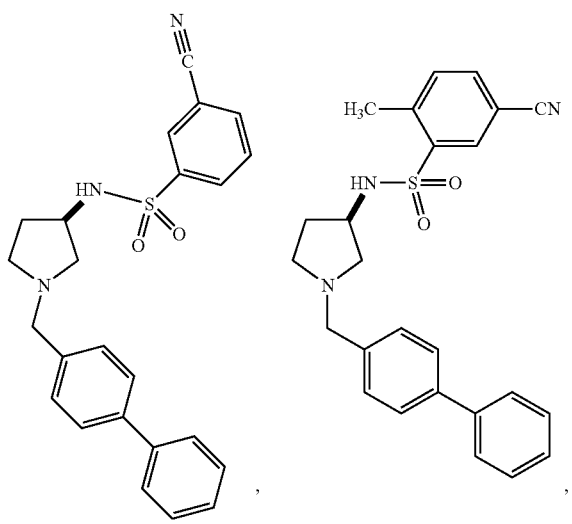

,

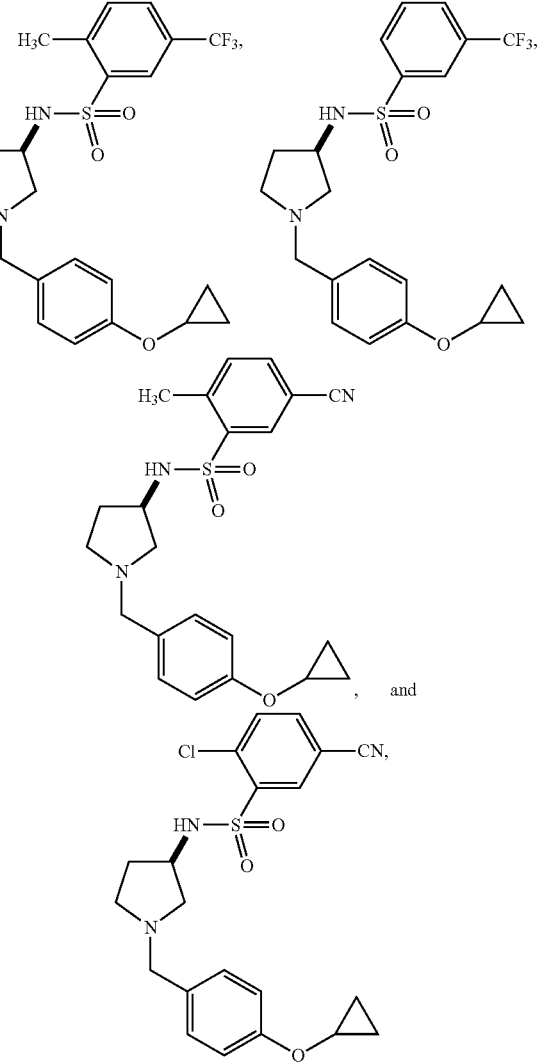

or a pharmaceutically acceptable salt thereof.

In another related aspect, the invention provides methods of treating a disease in a subject in need thereof, wherein the method includes administering to the subject an effective amount of a compound having structure Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI or a pharmaceutical composition thereof. In certain embodiments, the method includes contacting the bacteria with a compound having structure Ia. In certain other embodiments, the method includes contacting the bacteria with a compound having structure Ib. In other embodiments, the method includes contacting the bacteria with a compound having structure Ic. In certain embodiments, the method includes contacting the bacteria with a compound having structure Id. In certain other embodiments, the method includes contacting the bacteria with a compound having structure Ie.

In some embodiments, the method includes contacting the bacteria with a compound having structure II. In some embodiments, the method includes contacting the bacteria with a compound having structure IIIa. In other embodiments, the method includes contacting the bacteria with a compound having structure IIIb. In certain embodiments, the method includes contacting the bacteria with a compound having structure IIIc. In some embodiments, the method includes contacting the bacteria with a compound having structure IIId. In some other embodiments, the method includes contacting the bacteria with a compound having structure IIIe. In certain embodiments, the method includes contacting the bacteria with a compound having structure IIIf. In some embodiments, the method includes contacting the bacteria with a compound having structure IIIg. In other embodiments, the method includes contacting the bacteria with a compound having structure IIIh. In certain other embodiments, the method includes contacting the bacteria with a compound having structure IIIi.

In some embodiments, the method includes contacting the bacteria with a compound having structure Iva. In certain embodiments, the method includes contacting the bacteria with a compound having structure IVb. In some embodiments, the method includes contacting the bacteria with a compound having structure IVc. In certain embodiments, the method includes contacting the bacteria with a compound having structure IVd. In certain embodiments, the method includes contacting the bacteria with a compound having structure IVe. In other embodiments, the method includes contacting the bacteria with a compound having structure Va. In certain embodiments, the method includes contacting the bacteria with a compound having structure Vb. In some embodiments, the method includes contacting the bacteria with a compound having structure Vc. In some other embodiments, the method includes contacting the bacteria with a compound having structure Vd. In yet other embodiments, the method includes contacting the bacteria with a compound having structure, or VI.

In some embodiments, the method of treating the disease includes contacting the bacteria with a compound selected from:

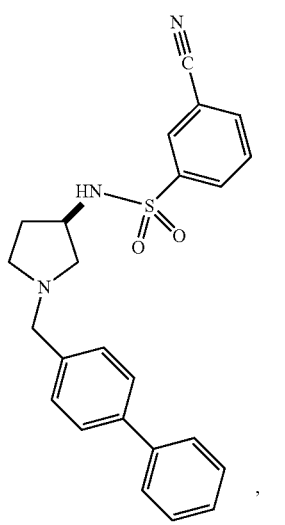

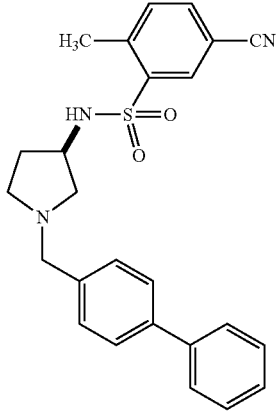

-continued

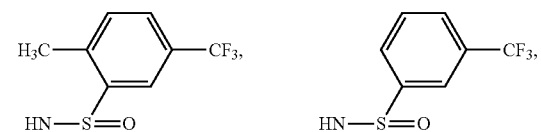

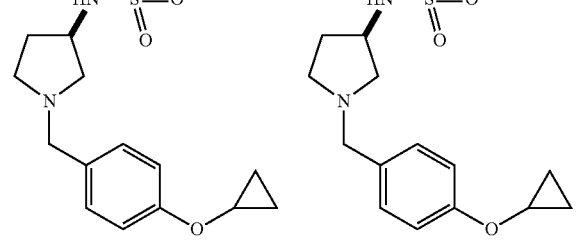

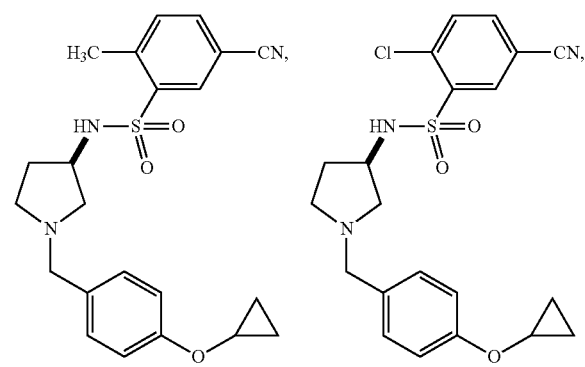

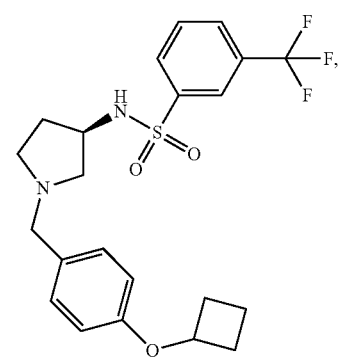

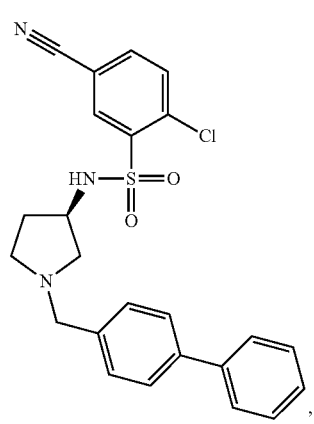

125
-continued
126
-continued
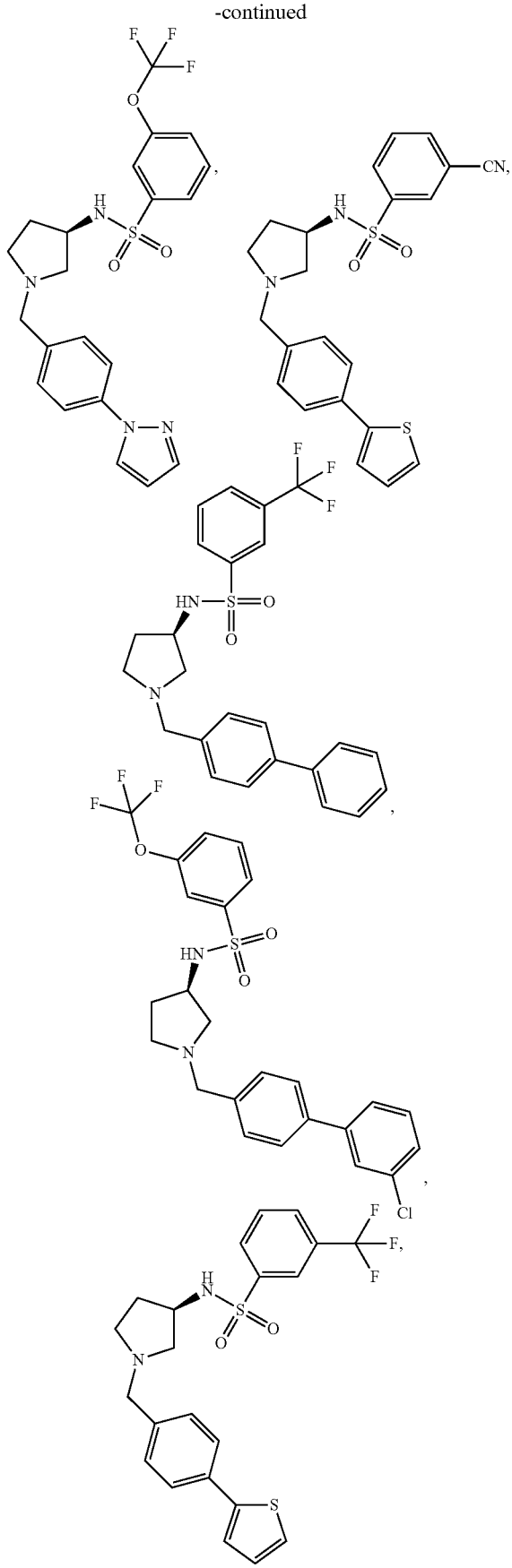
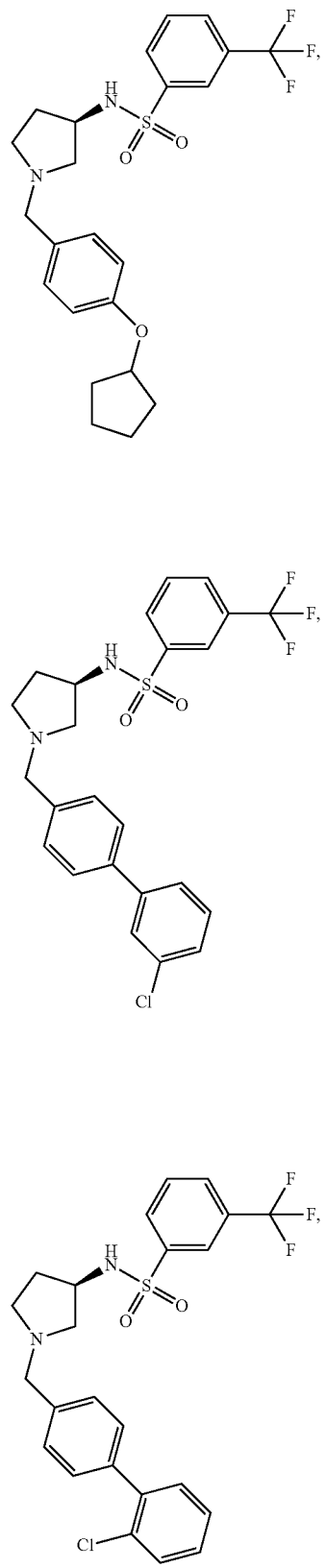

127
-continued
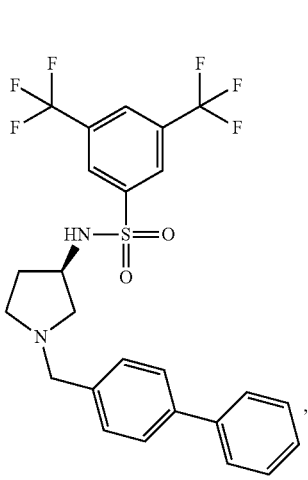
,
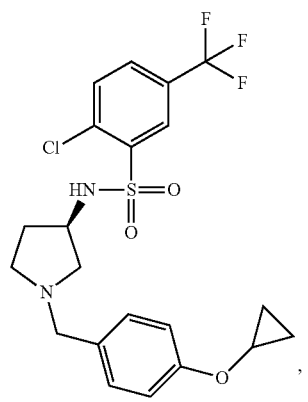
,
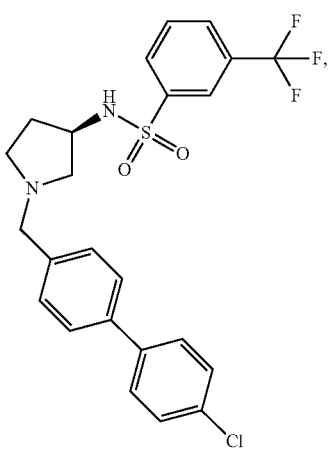
128
-continued
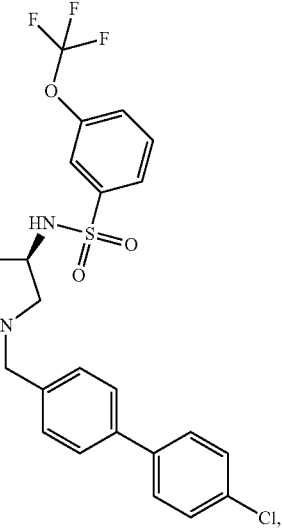
,
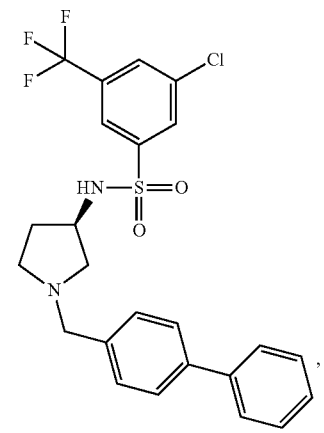
,
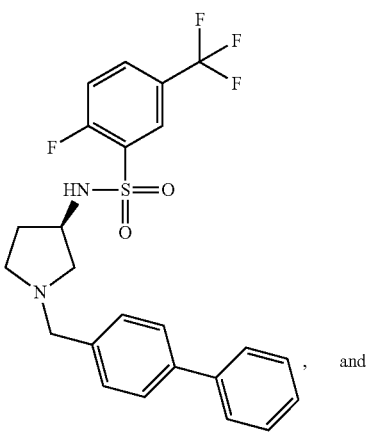
, and -continued

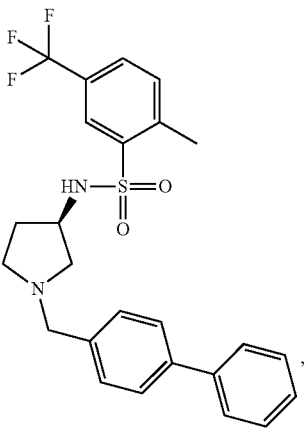

or a pharmaceutically acceptable salt thereof.

In some embodiments, the method of treating the disease includes contacting the bacteria with a compound selected from:

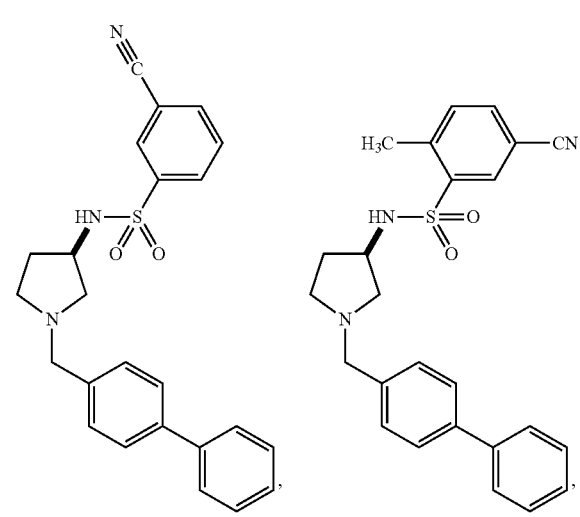

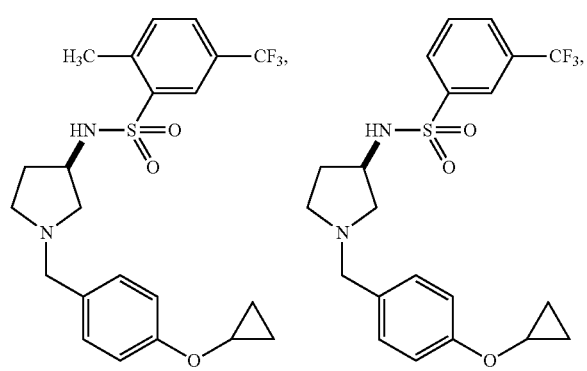

-continued

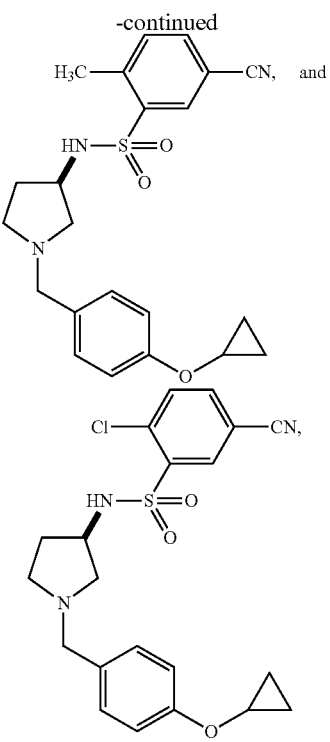

or a pharmaceutically acceptable salt thereof.

In some embodiments of the above methods, the disease is a bacterial infection. In some other embodiments, the bacterial infection is resistant to vancomycin. In yet other embodiments, the bacterial infection is resistant to fluoroquinolone antibiotics.

In some of the above methods, the claimed compounds may be formulated with an efflux pump inhibitor when the bacteria are Gram-negative bacteria.

VIII. Products Containing Compounds of the Invention

In another aspect, the present invention provides compounds and compositions that have antibacterial properties. Accordingly, the present application also contemplates embodiments wherein these compounds and compositions are included in products for disinfecting or sanitizing surfaces.

The present application contemplates liquid and solid compositions that include the compounds described herein and which are useful for decontaninating, disinfecting, and, or, sanitizing surfaces. Examples include, but are not limited to, solutions and solvents for household or medical cleaning applications.

The present application contemplates compositions wherein the compounds set forth herein are incorporated into medical devices, medical device coatings, opthalmic solutions, and wound dressings in order to impart antibacterial properties to the medical devices, opthalmic solutions, and wound dressings.

IX. Kits

In another aspect, the present invention provides a kit that includes a compound or composition described herein. In certain embodiments, the kit includes a compound having a structure selected from Ia, Ib, Ic, Id, Ie, II, IIIa, IIIb, IIIc, IIId, IIIe, IIIf, IIIg, IIIh, IIIi, IIIj, IVa, IVb, IVc, IVd, IVe, Va, Vb, Vc, Vd, or VI or a pharmaceutical composition thereof.

Some of the kits described herein include a label describing a method of administering a compound or composition described herein. Other kits described herein include a label describing a method of treating a bacterial infection.

The compositions of the present invention, including but not limited to compositions including a compound or composition described herein, may, if desired, be presented in a bottle, jar, or other container-closure system approved by the Food and Drug Administration or other regulatory body, which may provide one or more dosages containing the active ingredient. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as taught herein, a container closure system including the formulation or a dosage unit form including the formulation, and a notice or instructions describing a method of use as taught herein.

In some embodiments, the kit includes a container which is compartmentalized for holding the various elements of a formulation (e.g., the dry ingredients and the liquid ingredients) or composition, instructions for making the formulation or composition, and instructions for treating a bacterial infection. In certain embodiments, the kit may include the pharmaceutical preparation in dehydrated or dry form, with instructions for its rehydration (or reconstitution) and administration.

For use in diagnostic, research, and therapeutic applications described above, kits and systems are also provided by the invention. Kits of the present invention may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

A wide variety of kits, systems, and compositions can be prepared according to the present invention, depending upon the intended user of the kit and system and the particular needs of the user.

Kits with unit doses of the active composition, e.g., in oral, rectal, transdermal, or injectable doses (e.g., for intramuscular, intravenous, or subcutaneous injection), are provided. In such kits, in addition to the containers containing the unit doses will be an informational package insert describing the use and attendant benefits of the composition in treating a disease or condition set forth herein. Suitable active compositions and unit doses are those described herein above.

Some embodiments of the present invention include packages that include a compound or composition described herein packaged together with an antibiotic set forth above.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

X. Examples

Example 1. Preparation of Gyramide C2

The compounds described herein can be prepared by methods similar to those described in Foss, et al., *ACS Med. Chem. Lett.* 2011, 2, 289-292. Gyramide C2 can be synthesized according to Scheme 1.

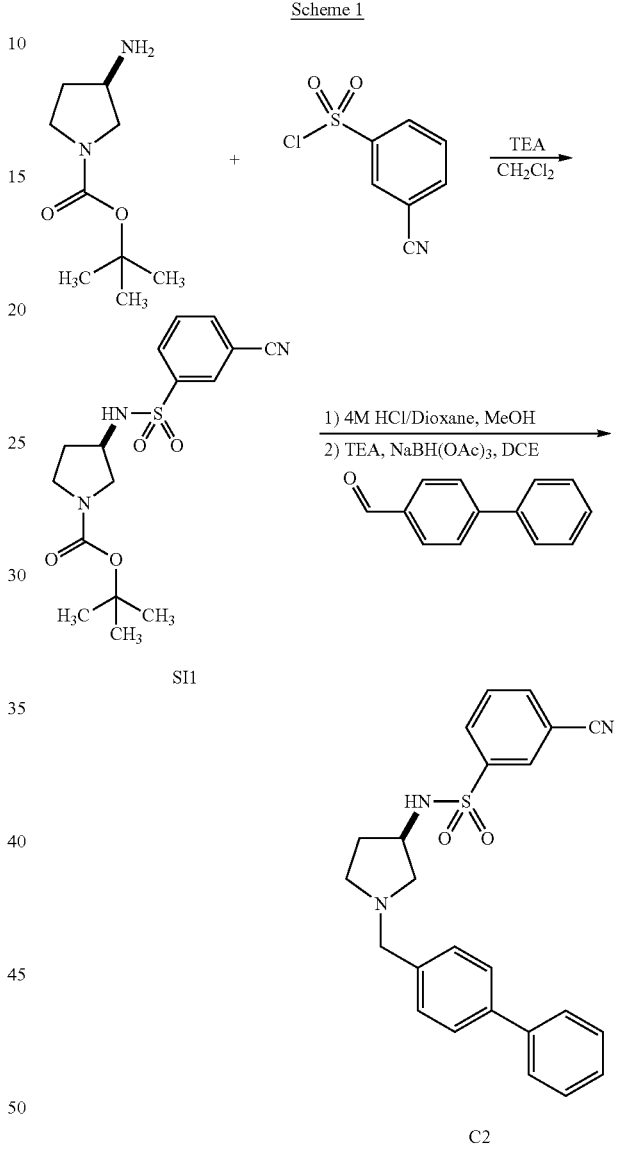

Preparation of SI1: To a solution of (R)-3-amino-1-N—BOC-pyrrolidine (1.00 g, 5.37 mmol) in CH$_2$Cl$_2$ (40.0 mL, 0.134 M) was added triethylamine (2.25 mL, 16.11 mmol) followed by 3-cyanobenzenesulfonyl chloride (1.21 g, 6.0 mmol) at room temperature. The mixture was stirred overnight. The following morning the mixture was diluted with CH$_2$Cl$_2$ (40 mL) and washed with water (40 mL). The aqueous layer was extracted CH$_2$Cl$_2$ (2×20 mL). The combined organic layers were dried with sodium sulfate, filtered, and concentrated. The crude residue was purified by flash chromatography (40-60% EtOAc/hexanes) to provide SI1 as a clear oil (1.70 g, 90%).

Preparation of C2: To a solution of SI1 (148 mg, 0.421 mmol) in methanol (6.00 mL) was added 4.0 M HCl in dioxane (6.00 mL, 6.0 mmol) drop-wise at room temperature. The mixture was stirred for 3 h and the solvent was removed by rotary evaporation followed by 2 h on the high-vac. DCE (12.0 mL, 0.035M) was added to the residue followed by triethylamine (0.180 mL, 1.26 mmol). The residue did not go fully into solution. Biphenyl-4-carboxaldehyde (77 mg, 0.42 mmol) was added and the reaction mixture was stirred for 20 minutes. Sodium triacetoxyborohydride (134 mg, 0.63 mmol) was added and the mixture was stirred for 24 h. The reaction mixture was partitioned between 1 M NaOH (30 mL) and CH$_2$Cl$_2$ (30 mL). The aqueous layer was extracted with CH$_2$Cl$_2$ (2×30 mL). The combined organic layers were dried with sodium sulfate, filtered and concentrated. The residue was purified by flash chromatography (2-3% CH$_3$OH/CH$_2$Cl$_2$) to provide the product as a clear oil that solidified upon cooling (150 mg, 85%); $^1$H NMR (400 MHz, CDCl$_3$) δ 8.15-8.13 (m, 1H), 8.05-8.01 (m, 1H), 7.80-7.76 (m, 1H), 7.62-7.57 (m, 3H), 7.54 (d, J=8.1 Hz, 2H), 7.48-7.42 (m, 2H), 7.40-7.31 (m, 1H), 7.30 (d, J=8.1 Hz, 2H), 3.91 (bs, 1H), 3.62 (d, J=12.7 Hz, 1H), 3.53 (d, J=12.8 Hz, 1H), 2.88-2.80 (m, 1H), 2.48-2.36 (m, 2H), 2.28-2.11 (m, 2H), 1.65-1.54 (m, 1H) (N—H proton not observed).

The compounds of the invention are observed to inhibit wild-type *E. coli*. Certain compounds. e.g., Gyramide C2, were observed to kill mutant *E. coli* at 300 nanomolar concentration and also to kill wild-type *E. coli* at 20 micromolar. It is worth noting that previously known compounds only killed mutant *E. coli* (i.e., with a drug pump knock out) in the low micromolar range and showed no efficacy against wild-type *E. coli*.

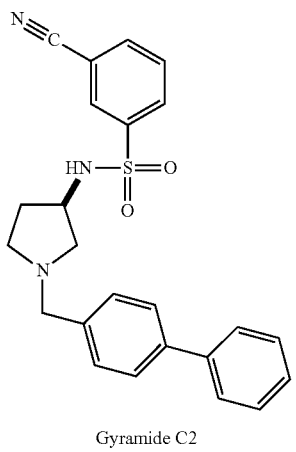

Gyramide C2

Example 2. Preparation of Gyramide Compounds

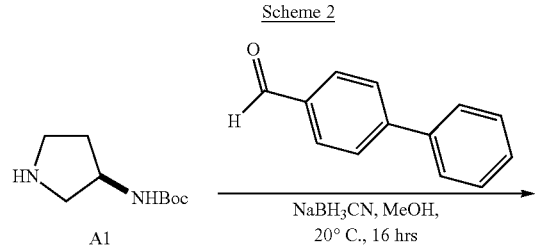

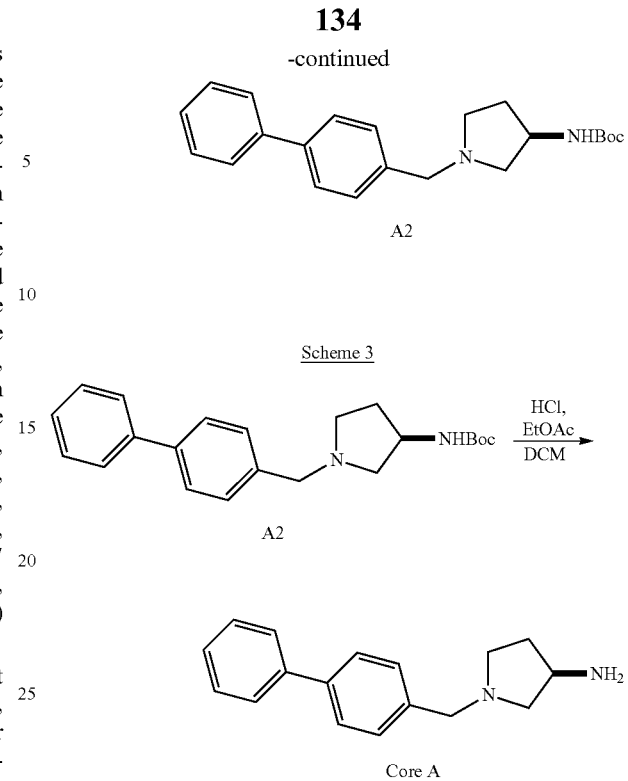

Preparation of Core A. Core A was prepared as shown in Scheme 2 and Scheme 3. To a solution of A1 (4.00 g, 21.48 mmol, 1.00 eq.) in MeOH (50.00 mL) was added. 4-phenylbenzaldehyde (4.11 g, 22.55 mmol, 1.05 eq.) at 15° C., the mixture was stirred at 15° C. for 2 hrs. Then NaBH$_3$CN (1.75 g, 27.92 mmol, 1.30 eq.) was added portionwise. The mixture was stirred at 15° C. for 16 hrs. The mixture was concentrated and the residue was dissolved in EA (200 mL), washed with water (200 mL), brine (200 mL), dried over Na2SO4, concentrated to give A2 as colorless oil. To a solution of A2 (6.00 g, 17.02 mmol, 1.00 eq.) in DCM (20.00 mL) was added HCl/EtOAc (100.00 mL) and the mixture was stirred at 15° C. for 12 hrs. The mixture was concentrated and the residue was washed with EtOAc, filtered and the solid was concentrated in vacuuo to obtain Core A (5.0 g crude, HCl) as a white solid.

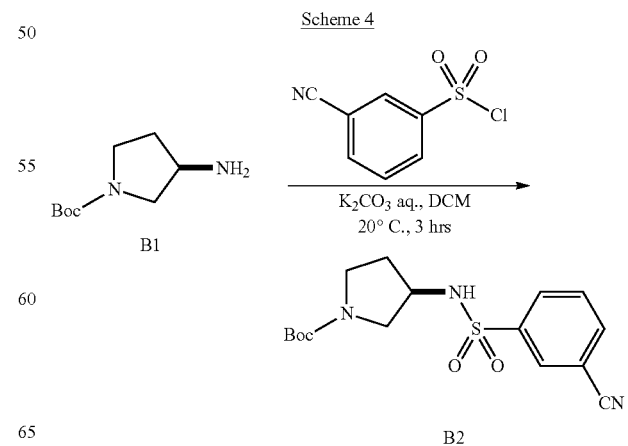

Scheme 5

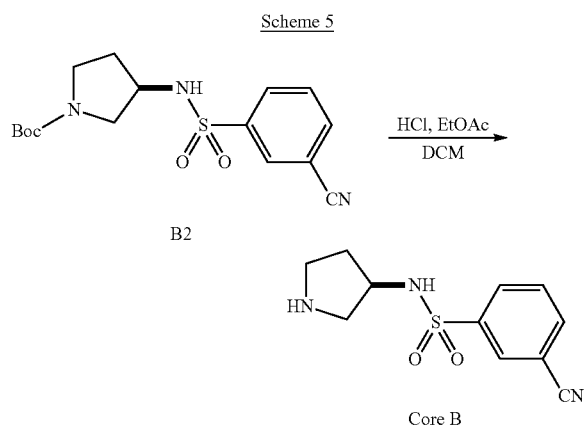

Preparation of Core B. Core B was prepared as shown in Scheme 4 and Scheme 5. To the mixture of B2 (3.00 g, 16.11 mmol, 1.00 eq.) in 2N K2CO3 (50.00 mL) and DCM (50.00 mL) was added 3-cyanobenzenesulfonyl chloride (3.41 g, 16.92 mmol, 1.05 eq.). The mixture was stirred at 20° C. for 3 hrs. The mixture was washed with water (100 mL), brine (100 mL), dried over Na2SO4, filtered and concentrated to give B2 (20 g, crude). To the solution of B2 (5.20 g, 14.80 mmol, 1.00 eq.) in DCM (30.00 mL) was added HCl/EtOAc (100.00 mL), the mixture was stirred at 20° C. for 3 hrs. The reaction was concentrated to give Core B (4.20 g, 14.59 mmol, 98.61% yield, HCl) as a white solid.

Scheme 6

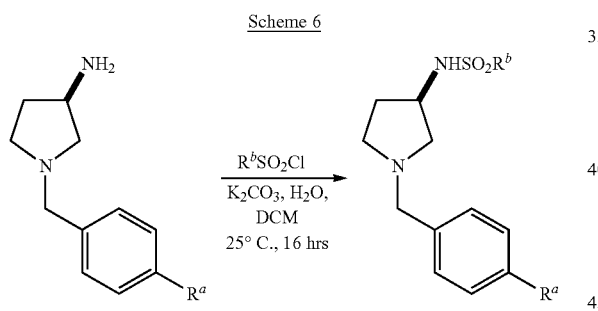

General Procedure for Preparation of Compounds via sulfonylation of pyrrolidine-amines. Several compounds were prepared as summarized in Scheme 6. To a mixture of a pyrrolidine-amine core intermediate and a sulfonyl chloride in DCM (2.0 mL) and H$_2$O (2.0 mL) was added K$_2$CO$_3$ (2 eq.) in one portion at 0° C. The mixture was stirred at 25° C. for 16 hours. The reaction mixture was diluted with H$_2$O (2 mL) and extracted with DCM (3×2 mL). The combined organic layers were washed with the saturated aqueous NaCl (3×2 mL), dried over [Na$_2$SO$_4$], filtered and concentrated under reduced pressure to give a residue. The residue was purified by prep-HPLC (TFA condition; basic condition) to obtain the desired product. This procedure was used for preparation of Compounds 16, 18, 19, 27, 29, 37, 59, 65, 81, 82, 83, 84, 85, 93, 95, 96, 104, 105, 111, 115, 121, 122, 123, 128, 130, 132, 135, 136, 137, 138, 139, 141, 146, 147, 149, 150, 153, 154, 156, 157, 158, 159, 160, 164, 165, 166, 167, 169, 174, 175, 178, 179, 180, and 181.

Scheme 7

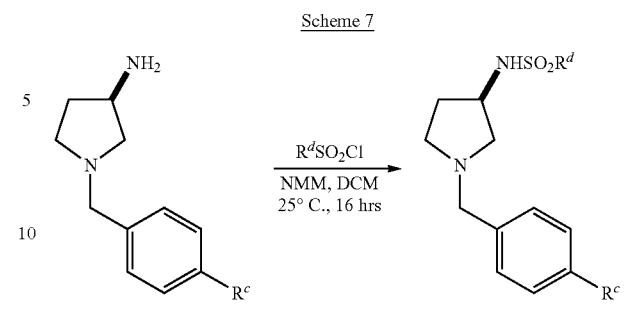

General Procedure for Preparation of Compounds via sulfonylation of pyrrolidine-amines. Several compounds were prepared as summarized in Scheme 7. To a mixture of a pyrrolidine-amine core intermediate and a sulfonyl chloride in DCM (2.0 mL) was added NMM (2 eq.) in one portion at 25° C. The mixture was stirred at 25° C. for 16 hours. The reaction mixture was concentrated in vacuo. The residue was purified by prep-HPLC (TFA condition; neutral condition; basic condition) to obtain the desired product. This procedure was used for preparation of Compounds 1, 4, 10, 11, 44, 47, 49, 68, 71, 72, 73, 77, 78, 79, 90, 91, 92, 94, 110, 112, 113, 114, 118, 119, 120, 131, 133, 134, 140, 142, 143, 148, 151, 152, 161, 162, 168, 182, and 183.

Scheme 8

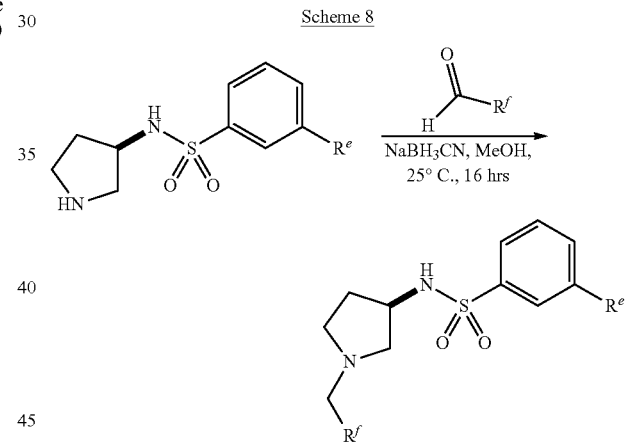

General Procedure for Preparation of Compounds via alkylation of pyrrolidines. Several compounds were prepared as summarized in Scheme 8. To a mixture of a pyrrolidine intermediate and an aldehyde intermediate in MeOH (2.0 mL) was added NaBH$_3$CN (2 eq.) in one portion at 25° C. The mixture was stirred at 25° C. for 16 hours. The residue was purified by prep-HPLC (TFA condition; neutral condition; basic condition) to obtain the desired product. This procedure was used for preparation of Compounds 2, 3, 5, 6, 7, 8, 9, 12, 13, 14, 15, 17, 20, 21, 22, 23, 24, 25, 26, 28, 30, 31, 32, 33, 34, 35, 36, 38, 39, 40, 41, 42, 43, 45, 46, 48, 50, 51, 52, 53, 54, 55, 56, 57, 58, 60, 61, 62, 63, 64, 66, 67, 69, 70, 74, 75, 76, 80, 86, 87, 88, 89, 97, 98, 99, 100, 101, 102, 103, 106, 107, 108, 109, 116, 117, 124, 125, 126, 127, 129, 144, 145, 155, 163, 170, 171, 172, 173, 176, and 177.

After synthesis as described above, the compounds were analyzed by liquid chromatography mass spectrometry (LC-MS). The purity of the compounds is set forth in Table 2, along with the observed molecular weights which were used to confirm the identity of the desired compounds.

TABLE 2

Isolation and characterization of gyramide compounds.

| No. | Isolated Mass (mg) | Purity (%) | Mol. Weight (calc) | Mol. Weight (obs) |
|---|---|---|---|---|
| 1 | 14.9 | 98.03 | 430.56 | 431.20 |
| 2 | 9.9 | 100.00 | 407.434 | 408.20 |
| 3 | 8.9 | 100.00 | 451.465 | 452.20 |
| 4 | 12 | 99.73 | 460.485 | 461.20 |
| 5 | 16.6 | 100.00 | 454.506 | 455.20 |
| 6 | 10.2 | 100.00 | 468.413 | 469.20 |
| 7 | 14.3 | 99.36 | 408.477 | 409.20 |
| 8 | 8.1 | 100.00 | 421.461 | 422.20 |
| 9 | 10.7 | 95.16 | 399.463 | 400.20 |
| 10 | 7.4 | 97.03 | 433.952 | 434.20 |
| 11 | 9.5 | 100.00 | 451.968 | 452.20 |
| 12 | 18.1 | 99.09 | 424.539 | 425.10 |
| 13 | 15.9 | 95.17 | 413.533 | 414.20 |
| 14 | 11.6 | 100.00 | 461.5 | 462.20 |
| 15 | 17.6 | 100.00 | 477.499 | 478.20 |
| 16 | 8.4 | 98.41 | 382.479 | 383.20 |
| 17 | 19.4 | 100.00 | 425.425 | 426.10 |
| 18 | 20.3 | 96.21 | 442.495 | 443.20 |
| 19 | 14.1 | 100.00 | 435.514 | 436.20 |
| 20 | 18.6 | 99.02 | 441.49 | 442.10 |
| 21 | 15 | 99.09 | 466.477 | 467.20 |
| 22 | 10.5 | 97.01 | 419.499 | 420.20 |
| 23 | 8.8 | 99.05 | 456.522 | 457.20 |
| 24 | 22.1 | 100.00 | 451.968 | 452.20 |
| 25 | 24.4 | 96.64 | 423.551 | 424.20 |
| 26 | 10.5 | 97.65 | 472.521 | 473.20 |
| 27 | 13.6 | 97.75 | 460.512 | 461.20 |
| 28 | 21.8 | 99.78 | 510.956 | 511.20 |
| 29 | 8 | 98.35 | 520.685 | 521.20 |
| 30 | 16 | 96.85 | 421.515 | 422.20 |
| 31 | 13.5 | 99.51 | 387.519 | 388.10 |
| 32 | 15.3 | 100.00 | 466.54 | 467.20 |
| 33 | 13.6 | 100.00 | 467.465 | 468.20 |
| 34 | 17.9 | 97.52 | 424.539 | 425.10 |
| 35 | 18 | 97.93 | 450.477 | 451.20 |
| 36 | 14.7 | 100.00 | 483.527 | 484.10 |
| 37 | 10.5 | 100.00 | 538.701 | 539.20 |
| 38 | 22.2 | 100.00 | 484.532 | 485.20 |
| 39 | 12.2 | 99.75 | 500.531 | 501.20 |
| 40 | 21.6 | 97.55 | 425.544 | 426.20 |
| 41 | 17.8 | 95.60 | 468.532 | 469.20 |
| 42 | 16.6 | 96.09 | 472.521 | 473.20 |
| 43 | 15 | 98.98 | 461.5 | 462.20 |
| 44 | 8.1 | 97.83 | 434.551 | 435.20 |
| 45 | 15.1 | 100.00 | 484.532 | 485.20 |
| 46 | 19.1 | 97.95 | 418.511 | 419.20 |
| 47 | 15.2 | 95.38 | 494.957 | 492.20 |
| 48 | 8.7 | 97.93 | 477.499 | 478.20 |
| 49 | 10 | 100.00 | 416.534 | 417.20 |
| 50 | 18 | 99.70 | 494.957 | 495.20 |
| 51 | 17.2 | 100.00 | 484.413 | 485.10 |
| 52 | 14.9 | 99.33 | 484.479 | 485.10 |
| 53 | 17.1 | 99.47 | 482.539 | 483.20 |
| 54 | 15 | 95.06 | 441.543 | 442.20 |
| 55 | 20.7 | 100.00 | 500.478 | 501.10 |
| 56 | 9.2 | 99.46 | 464.504 | 465.10 |
| 57 | 9.7 | 98.27 | 467.528 | 468.20 |
| 58 | 13 | 99.03 | 462.488 | 463.10 |
| 59 | 14.1 | 95.01 | 409.93 | 410.10 |
| 60 | 12.5 | 99.74 | 442.452 | 443.10 |
| 61 | 23.5 | 99.72 | 490.538 | 491.10 |
| 62 | 9.4 | 99.28 | 458.451 | 459.10 |
| 63 | 8.1 | 99.57 | 478.487 | 479.10 |
| 64 | 11.1 | 97.23 | 464.449 | 465.10 |
| 65 | 9.2 | 97.01 | 518.669 | 519.10 |
| 66 | 24 | 99.13 | 490.538 | 491.20 |
| 67 | 17.7 | 95.05 | 418.511 | 419.20 |
| 68 | 12.4 | 100.00 | 448.577 | 449.20 |
| 69 | 27.9 | 99.50 | 494.957 | 495.20 |
| 70 | 12.9 | 99.44 | 451.968 | 452.20 |
| 71 | 19.7 | 98.91 | 478.502 | 479.20 |
| 72 | 18.9 | 98.62 | 466.614 | 467.20 |
| 73 | 23 | 96.38 | 484.631 | 485.20 |
| 74 | 17.9 | 99.09 | 506.537 | 507.20 |
| 75 | 22.4 | 97.71 | 510.956 | 511.20 |
| 76 | 19.2 | 98.97 | 506.537 | 507.20 |
| 77 | 8.6 | 99.33 | 431.936 | 432.10 |
| 78 | 6.6 | 100.00 | 460.485 | 461.10 |
| 79 | 5.3 | 100.00 | 464.598 | 465.10 |
| 80 | 6.8 | 100.00 | 447.549 | 448.20 |
| 81 | 7.6 | 100.00 | 528.51 | 529.20 |
| 82 | 11 | 97.26 | 497.072 | 497.30 |
| 83 | 18.2 | 99.48 | 479.055 | 479.20 |
| 84 | 10.3 | 97.10 | 425.544 | 426.30 |
| 85 | 17.4 | 98.05 | 477.039 | 477.20 |
| 86 | 11.6 | 100.00 | 430.507 | 431.20 |
| 87 | 10.8 | 99.32 | 450.423 | 451.20 |
| 88 | 10.6 | 100.00 | 488.52 | 489.20 |
| 89 | 15.4 | 99.01 | 480.449 | 481.20 |
| 90 | 8.3 | 100.00 | 474.924 | 475.00 |
| 91 | 25.4 | 100.00 | 454.506 | 455.10 |
| 92 | 18.3 | 99.21 | 476.94 | 477.20 |
| 93 | 19.6 | 98.88 | 425.544 | 426.20 |
| 94 | 13.7 | 98.44 | 474.924 | 475.20 |
| 95 | 15.3 | 98.48 | 423.528 | 424.20 |
| 96 | 8.8 | 100.00 | 423.528 | 424.20 |
| 97 | 13.4 | 98.77 | 424.516 | 425.20 |
| 98 | 25.6 | 100.00 | 511.385 | 511.20 |
| 99 | 16.4 | 98.05 | 467.504 | 468.20 |
| 100 | 12.5 | 98.53 | 483.504 | 484.20 |
| 101 | 26.3 | 98.54 | 451.968 | 452.20 |
| 102 | 21.8 | 100.00 | 494.957 | 495.20 |
| 103 | 23.2 | 100.00 | 510.956 | 511.20 |
| 104 | 8.2 | 96.48 | 373.469 | 374.20 |
| 105 | 11.5 | 95.72 | 443.561 | 444.20 |
| 106 | 6.7 | 100.00 | 466.422 | 467.20 |
| 107 | 6.3 | 100.00 | 483.527 | 484.10 |
| 108 | 21.1 | 96.06 | 451.465 | 452.20 |
| 109 | 27 | 100.00 | 411.517 | 412.20 |
| 110 | 25.4 | 97.31 | 494.957 | 495.10 |
| 111 | 10.7 | 100.00 | 449.588 | 450.20 |
| 112 | 12.6 | 97.31 | 413.533 | 414.20 |
| 113 | 12.3 | 100.00 | 411.517 | 412.20 |
| 114 | 6.7 | 100.00 | 478.502 | 479.20 |
| 115 | 14.3 | 95.08 | 461.58 | 462.30 |
| 116 | 26.8 | 99.18 | 468.397 | 468.20 |
| 117 | 24.6 | 99.67 | 527.385 | 527.20 |
| 118 | 10.3 | 95.04 | 433.952 | 434.20 |
| 119 | 10.4 | 95.07 | 431.936 | 432.20 |
| 120 | 8.7 | 95.47 | 451.968 | 452.20 |
| 121 | 6.2 | 99.58 | 389.512 | 390.20 |
| 122 | 9.7 | 97.45 | 427.947 | 428.20 |
| 123 | 6.8 | 99.70 | 443.562 | 444.30 |
| 124 | 21.4 | 98.71 | 408.477 | 409.20 |
| 125 | 11.7 | 99.38 | 450.477 | 451.20 |
| 126 | 10.2 | 97.97 | 407.489 | 408.20 |
| 127 | 16 | 99.61 | 447.549 | 448.20 |
| 128 | 15.1 | 98.24 | 508.477 | 509.20 |
| 129 | 18.9 | 96.37 | 467.465 | 468.10 |
| 130 | 5 | 100.00 | 362.447 | 363.20 |
| 131 | 15.5 | 99.16 | 431.55 | 432.20 |
| 132 | 8.7 | 100.00 | 407.914 | 408.20 |
| 133 | 5.1 | 97.41 | 428.544 | 429.30 |
| 134 | 5 | 100.00 | 414.518 | 415.20 |
| 135 | 11.3 | 100.00 | 510.493 | 511.20 |
| 136 | 9.3 | 100.00 | 364.462 | 365.20 |
| 137 | 24 | 100.00 | 407.529 | 408.20 |
| 138 | 6.7 | 100.00 | 400.495 | 401.20 |
| 139 | 9.7 | 100.00 | 389.512 | 390.20 |
| 140 | 9.1 | 100.00 | 476.94 | 477.20 |
| 141 | 19.1 | 97.25 | 427.947 | 428.20 |
| 142 | 5.8 | 95.37 | 505.049 | 505.20 |
| 143 | 7.7 | 97.30 | 431.55 | 432.20 |
| 144 | 20.3 | 100.00 | 480.503 | 481.20 |
| 145 | 11.6 | 100.00 | 407.489 | 408.20 |
| 146 | 10.5 | 99.06 | 393.502 | 394.20 |
| 147 | 29.6 | 99.72 | 411.492 | 412.20 |
| 148 | 12.6 | 100.00 | 487.032 | 487.20 |

TABLE 2-continued

Isolation and characterization of gyramide compounds.

| No. | Isolated Mass (mg) | Purity (%) | Mol. Weight (calc) | Mol. Weight (obs) |
|---|---|---|---|---|
| 149 | 16.3 | 100.00 | 409.93 | 410.20 |
| 150 | 9.8 | 96.04 | 393.476 | 394.20 |
| 151 | 10.1 | 100.00 | 485.017 | 485.20 |
| 152 | 11.2 | 97.32 | 458.47 | 459.20 |
| 153 | 7.1 | 100.00 | 387.496 | 388.20 |
| 154 | 17.6 | 95.02 | 391.46 | 392.20 |
| 155 | 11.6 | 100.00 | 429.532 | 430.10 |
| 156 | 11.1 | 98.10 | 440.479 | 441.20 |
| 157 | 8.7 | 100.00 | 441.546 | 442.30 |
| 158 | 9.5 | 100.00 | 429.556 | 430.20 |
| 159 | 5 | 100.00 | 398.479 | 399.20 |
| 160 | 5.4 | 98.05 | 418.511 | 419.20 |
| 161 | 10.8 | 99.57 | 413.533 | 414.20 |
| 162 | 8.9 | 97.90 | 411.517 | 412.20 |
| 163 | 25.5 | 98.64 | 466.477 | 467.20 |
| 164 | 18 | 100.00 | 431.572 | 432.20 |
| 165 | 11.7 | 97.26 | 417.497 | 418.10 |
| 166 | 11.9 | 100.00 | 415.481 | 416.10 |
| 167 | 7.1 | 97.54 | 375.485 | 376.20 |
| 168 | 9 | 99.32 | 458.47 | 459.20 |
| 169 | 19.6 | 95.34 | 407.914 | 408.20 |
| 170 | 17 | 100.00 | 421.515 | 422.10 |
| 171 | 16.9 | 99.23 | 464.504 | 465.10 |
| 172 | 19.6 | 100.00 | 480.503 | 481.10 |
| 173 | 10.9 | 100.00 | 467.528 | 468.20 |
| 174 | 14.6 | 99.45 | 407.529 | 408.10 |
| 175 | 14.8 | 98.28 | 387.496 | 388.10 |
| 176 | 9.6 | 99.15 | 446.507 | 447.00 |
| 177 | 13.8 | 99.77 | 470.505 | 471.10 |
| 178 | 14.9 | 100.00 | 443.561 | 444.20 |
| 179 | 11.3 | 97.47 | 443.559 | 444.30 |
| 180 | 10.7 | 95.28 | 461.576 | 462.30 |
| 181 | 6.3 | 98.45 | 441.543 | 442.20 |
| 182 | 10.3 | 100.00 | 474.538 | 475.10 |
| 183 | 5 | 95.69 | 456.522 | 457.10 |

Example 3. Minimum Inhibitory Concentration (MIC) Measurements of Gyramide Compounds The minimum inhibitory concentration (MIC) of gyramide C2 against different bacterial strains, including: pathogenic strains (Table 3), gyramide A resistant strains (Table 4), and ciprofloxacin resistant strains (Table 5), were measured. A microdilution method in 96-well plates was used and the MIC protocol established by the Clinical Laboratory Standards Institute was followed. From a growing subculture, a 1:10000 inoculum of each strain in Luria-Bertani media was prepared and aliquoted 100 μL in 4 columns of wells, except for the top row wells, which contained 200 μL of inoculum. A solution of gyramide C2 was aliquoted into 3 of the wells containing 200 μL and DMSO was added to the 4$^{th}$ well. The liquid in each of wells was mixed with a multi-channel pipet and 100 μL was transferred to the next well and mixed. The 2-fold dilution was continued down the 96-well plate until 100 μL was left, which was discarded. The plates were incubated at 37° C. with shaking for 16-18 hours. The MIC was determined as the lowest concentration that inhibited growth and had no turbidity by visual inspection.

Discussion of the MIC Results.

The MIC of gyramide C2 against *E. coli* BW25113 compared to *E. coli* BW25113 ΔtolC demonstrates that gyramide C2 is more potent than the initial gyramide analogs, however it remains a viable substrate for drug efflux pumps. It is possible that C2 binds to GyrBAfus with an affinity that is similar to gyramides A-C and that the difference in the potency of C2 arises because it is not effluxed out of cells as efficiently as gyramides A-C. The efflux pump inhibitor, Phe-Arg β-naphtylamide (PAβN) was used to reduce drug efflux and gyramide C2 was found to be relatively potent against several pathogenic bacterial strains (Table 3). In the presence of PaβN, gyramide C2 was the more effective against *Shigella boydii, Salmonella typhimurium,* and *Enterobacter aerogenes.* In the absence of PAβN, the potency of gyramide C2 against most organisms was very low. Interestingly, gyramide C2 was primarily active against *Escherichia coli,* which provides an unique application for organism-specific chemotherapeutic treatment.

Spontaneous mutants of *E. coli* that exhibited a lower susceptibility to gyramide A were isolated. The MIC of gyramide C2, novobiocin, and ciprofloxacin was measured against these resistant mutants (Table 4). Gyramide A resistant mutants are also resistant to gyramide C2 and the MIC of the compound was >200 times larger against the mutants compared to the parent strain. This result indicates that the chemical modification on gyramide C2 did not interrupt the unique gyrase inhibition activity of this analog. The MIC of novobiocin against the gyramide A resistant mutants was the same compared to the parent strain. Furthermore, the MIC of ciprofloxacin is 1-2 times the MIC of the parent strain. The results involving novobiocin and ciprofloxacin demonstrate that these known gyrase inhibitors are not cross-resistant to the gyramides and their mode of gyrase inhibition is distinct.

Spontaneous mutants of *E. coli* were also isolated having decreased susceptibility to ciprofloxacin. The MIC of ciprofloxacin, gyramide C, and gyramide C2 against these mutant strains (Table 5) was determined. The MIC of ciprofloxacin is >8-32 times than the MIC against the parent strain, indicating the strains are resistant to ciprofloxacin. These ciprofloxacin resistant strains are not resistant to gyramide C, as the MIC is 1-4 times larger than the parent strain. Gyramide C2 contains one additional functional group compared to gyramide C and remains active against the ciprofloxacin resistant strains. The MIC of gyramide C2 against ciprofloxacin resistant strains was 4-8 times the parent strain.

TABLE 3

MIC measurements of gyramide C2 against non-pathogenic and pathogenic bacterial strains with and without the TolC drug efflux pump inhibitor, Phe-Arg β-naphtylamide (PAβN).

| Bacterial Strains | Gyramide C2 (μM) with PAβN (60 μM) | Gyramide C2 (μM) without PAβN (60 μM) |
|---|---|---|
| *E. coli* BW25113 | Not measured | 20 |
| *E. coli* BW25113 ΔtolC | Not measured | 0.25 |
| *Staphylococcus aureus* | 40 | 160 |
| *Vibrio cholera* | 40 | 160 |
| *Morganella morganii* | >640 | >640 |
| *Pseudomonas aeruginosa* | 20 | >640 |
| *Shigella boydii* | 1.25 | 80 |
| *Klebsiella pneumonia* | 20 | >640 |
| *Salmonella typhimurium* | 2.5 | >640 |
| *Edwardsiella tarda* | 20 | >640 |
| *Enterobacter aerogenes* | 10 | >640 |
| *Acinetobacter baumannii* | 40 | >640 |

TABLE 4

MIC measurements of gyramide A, gyramide C2, novobiocin and ciprofloxacin against five gyramide-resistant mutants.

| Strain | | Gyramide A (μM) | Gyramide C2 (μM) | Novobiocin (μM) | Ciprofloxacin (μM) |
|---|---|---|---|---|---|
| E. coli BW25113 ΔtolC (parent strain) | | 20 | 0.1 | 1.25 | 0.005 |
| gyr$^R$ isolates | GyrA Pro35Thr | 320 | 25.6 | 1.25 | 0.005 |
| | GyrA Ser97Pro | 320 | >25.6 | 1.25 | 0.005 |
| | GyrA Phe96Leu | 320 | 25.6 | 1.25 | 0.01 |
| | GyrA His45Tyr | 320 | >25.6 | 1.25 | 0.01 |
| | GyrB Thr508Met | 320 | 25.6 | 1.25 | 0.01 |

TABLE 5

MIC measurements of ciprofloxacin, gyramide C and gyramide C2 against isolated ciprofloxacin-resistant mutants (mutation Ser83 and Asp87 are found in the literature as conferring resistance to ciprofloxacin in clinical environments)

| Strain | | Ciprofloxacin (nM) | Gyramide C (nM) | Gyramide C2 (nM) |
|---|---|---|---|---|
| E. coli BW25113 ΔtolC (parent strain) | | 6.25 | 2500 | 100 |
| cip$^R$ isolates | GyrA Ser83Leu | 200 | 2500 | 400 |
| | GyrA Asp87Gly | 50 | 5000 | 800 |
| | GyrA Asp87Tyr | 100 | 5000 | 800 |
| | GyrB Ser464Phe | 50 | 10000 | 400 |

Minimum inhibitory concentrations of various gyramide compounds against 20 strains of bacteria were determined using the procedure described above. The MIC values against a number of strains are set forth in Table 6.

TABLE 6

MIC values determined for gyramide compounds.

MIC (μg/mL)

| No. | A | B | C | D | E | F | G | H | I | J | K | L |
|---|---|---|---|---|---|---|---|---|---|---|---|---|
| 77 | 8 | 8 | 0.125 | 8 | ~8 | 1 | 4 | >8 | >8 | >8 | >8 | >8 |
| 91 | 4 | 8 | <0.0625 | 8 | >8 | 4 | 8 | 4 | 8 | 2 | 8 | 4 |
| 113 | ~8 | ~8 | 0.25 | ~8 | >8 | 2 | ~8 | >8 | >8 | >8 | >8 | >8 |
| 143 | 8 | ~8 | <0.0625 | ~8 | >8 | 1 | 4 | >8 | >8 | ~8 | >8 | >8 |
| 156 | ~8 | ~8 | 0.125 | ~8 | >8 | 4 | 8 | >8 | >8 | >8 | >8 | >8 |
| 5 | >8 | ~8 | 0.125 | >8 | >8 | 8 | >8 | >8 | >8 | >8 | >8 | >8 |
| 11 | >8 | ~8 | <0.062 | >8 | >8 | 4 | >8 | >8 | >8 | >8 | >8 | >8 |
| 21 | >8 | >8 | 2 | >8 | >8 | >8 | >8 | 8 | >8 | 2 | >8 | >8 |
| 25 | ~8 | ~8 | 0.25 | >8 | >8 | 4 | >8 | >8 | >8 | >8 | >8 | >8 |
| 27 | >8 | >8 | 0.5 | >8 | >8 | 4 | >8 | >8 | >8 | 8 | >8 | 8 |
| 28 | >8 | >8 | >8 | >8 | >8 | >8 | >8 | >8 | >8 | 2 | >8 | ~8 |
| 32 | >8 | >8 | 1 | >8 | >8 | 8 | >8 | >8 | >8 | 8 | >8 | 8 |
| 41 | >8 | >8 | 0.5 | >8 | >8 | 8 | >8 | ~8 | >8 | 8 | >8 | 8 |
| 50 | >8 | >8 | 8 | >8 | >8 | >8 | >8 | 8 | >8 | 2 | >8 | ~8 |
| 69 | >8 | >8 | 8 | >8 | >8 | >8 | >8 | >8 | >8 | 4 | >8 | >8 |
| 81 | >8 | >8 | >8 | >8 | >8 | >8 | >8 | >8 | >8 | 8 | >8 | ~8 |
| 83 | >8 | >8 | 8 | >8 | >8 | >8 | ~8 | >8 | >8 | 8 | >8 | 8 |
| 85 | >8 | >8 | ~8 | >8 | >8 | >8 | ~8 | >8 | >8 | 4 | >8 | 8 |
| 90 | >8 | ~8 | <0.0625 | >8 | >8 | 4 | ~8 | >8 | >8 | >8 | >8 | >8 |
| 102 | >8 | >8 | ~8 | >8 | >8 | >8 | 8 | >8 | 8 | >8 | >8 | >8 |
| 103 | >8 | >8 | ~8 | >8 | >8 | >8 | 8 | >8 | 8 | >8 | >8 | ~8 |
| 110 | >8 | >8 | >8 | >8 | >8 | >8 | >8 | >8 | >8 | 4 | >8 | 8 |
| 114 | >8 | >8 | 1 | >8 | >8 | 4 | >8 | >8 | ~8 | >8 | ~8 | ~8 |
| 182 | >8 | >8 | 4 | >8 | >8 | >8 | >8 | >8 | >8 | 4 | >8 | ~8 |

TABLE 6-continued

MIC values determined for gyramide compounds.

MIC (μg/mL)

| No. | A | B | C | D | E | F | G | H | I | J | K | L |
|---|---|---|---|---|---|---|---|---|---|---|---|---|
| 1 | >8 | >8 | >8 | >8 | >8 | >8 | >8 | >8 | >8 | >8 | >8 | >8 |
| 2 | >8 | >8 | 8 | >8 | >8 | >8 | >8 | >8 | >8 | >8 | >8 | >8 |
| 3 | >8 | >8 | 4 | >8 | >8 | >8 | >8 | >8 | >8 | >8 | >8 | >8 |
| 4 | >8 | >8 | 0.5 | >8 | >8 | >8 | >8 | >8 | >8 | >8 | >8 | >8 |
| 6 | >8 | >8 | 4 | >8 | >8 | >8 | >8 | >8 | >8 | >8 | >8 | >8 |
| 7 | >8 | >8 | 8 | >8 | >8 | >8 | >8 | >8 | >8 | >8 | >8 | >8 |
| 8 | >8 | >8 | 2 | >8 | >8 | 8 | >8 | >8 | >8 | >8 | >8 | >8 |
| 9 | >8 | >8 | >8 | >8 | >8 | >8 | >8 | >8 | >8 | >8 | >8 | >8 |
| 10 | >8 | >8 | 0.25 | >8 | >8 | 8 | >8 | >8 | >8 | >8 | >8 | >8 |
| 12 | >8 | >8 | 2 | >8 | >8 | >8 | >8 | >8 | >8 | >8 | >8 | >8 |
| 13 | >8 | >8 | 8 | >8 | >8 | >8 | >8 | >8 | >8 | >8 | >8 | >8 |
| 14 | >8 | >8 | 2 | >8 | >8 | >8 | >8 | >8 | >8 | >8 | >8 | >8 |
| 15 | >8 | >8 | 4 | >8 | >8 | >8 | >8 | >8 | >8 | >8 | >8 | >8 |
| 16 | >8 | >8 | 2 | >8 | >8 | 8 | >8 | >8 | >8 | >8 | >8 | >8 |
| 17 | >8 | >8 | 8 | >8 | >8 | >8 | >8 | >8 | >8 | >8 | >8 | >8 |
| 18 | >8 | >8 | 0.5 | >8 | >8 | 8 | >8 | >8 | >8 | >8 | >8 | >8 |
| 19 | >8 | >8 | 0.25 | >8 | >8 | 4 | >8 | >8 | >8 | >8 | >8 | >8 |
| 20 | >8 | >8 | 8 | >8 | >8 | >8 | >8 | >8 | >8 | >8 | >8 | >8 |
| 22 | >8 | >8 | 8 | >8 | >8 | >8 | >8 | >8 | >8 | >8 | >8 | >8 |
| 23 | >8 | >8 | 0.5 | >8 | >8 | >8 | >8 | >8 | >8 | >8 | >8 | >8 |
| 24 | >8 | >8 | 4 | >8 | >8 | >8 | >8 | >8 | >8 | >8 | >8 | >8 |
| 26 | >8 | >8 | 0.5 | >8 | >8 | >8 | >8 | >8 | >8 | >8 | >8 | >8 |
| 29 | >8 | >8 | >8 | >8 | >8 | >8 | >8 | >8 | >8 | >8 | >8 | >8 |
| 30 | >8 | >8 | >8 | >8 | >8 | >8 | >8 | >8 | >8 | >8 | >8 | >8 |
| 31 | >8 | >8 | ~8 | >8 | >8 | >8 | >8 | >8 | >8 | >8 | >8 | >8 |
| 33 | >8 | >8 | >8 | >8 | >8 | >8 | >8 | >8 | >8 | >8 | >8 | >8 |
| 34 | >8 | >8 | >8 | >8 | >8 | >8 | >8 | >8 | >8 | >8 | >8 | >8 |
| 35 | >8 | >8 | 1 | >8 | >8 | >8 | >8 | >8 | >8 | >8 | >8 | >8 |
| 36 | >8 | >8 | 2 | >8 | >8 | >8 | >8 | >8 | >8 | >8 | >8 | >8 |
| 37 | >8 | >8 | >8 | >8 | >8 | >8 | >8 | >8 | >8 | >8 | >8 | >8 |
| 38 | >8 | >8 | 1 | >8 | >8 | >8 | >8 | >8 | >8 | >8 | >8 | >8 |
| 39 | >8 | >8 | 1 | >8 | >8 | >8 | >8 | >8 | >8 | >8 | >8 | >8 |
| 40 | >8 | >8 | 0.5 | >8 | >8 | 4 | >8 | >8 | >8 | >8 | >8 | >8 |
| 42 | >8 | >8 | >8 | >8 | >8 | >8 | >8 | >8 | >8 | >8 | >8 | >8 |
| 43 | >8 | >8 | 0.5 | >8 | >8 | >8 | >8 | >8 | >8 | >8 | >8 | >8 |
| 44 | >8 | >8 | 0.25 | >8 | >8 | 8 | >8 | >8 | >8 | >8 | >8 | >8 |
| 45 | >8 | >8 | 2 | >8 | >8 | >8 | >8 | >8 | >8 | 8 | >8 | >8 |
| 46 | >8 | >8 | 1 | >8 | >8 | 8 | >8 | >8 | >8 | >8 | >8 | >8 |
| 47 | >8 | >8 | 1 | >8 | >8 | ~8 | >8 | >8 | >8 | ~8 | >8 | ~8 |
| 48 | >8 | >8 | 1 | >8 | >8 | >8 | >8 | >8 | >8 | >8 | >8 | >8 |
| 49 | >8 | >8 | 2 | >8 | >8 | >8 | >8 | >8 | >8 | >8 | >8 | >8 |
| 51 | >8 | >8 | 4 | >8 | >8 | >8 | >8 | >8 | >8 | >8 | >8 | >8 |
| 52 | >8 | >8 | 4 | >8 | >8 | >8 | >8 | >8 | >8 | >8 | >8 | >8 |
| 53 | >8 | >8 | 4 | >8 | >8 | >8 | >8 | >8 | >8 | 8 | >8 | >8 |
| 54 | >8 | >8 | 2 | >8 | >8 | 8 | >8 | >8 | >8 | >8 | >8 | >8 |
| 55 | >8 | >8 | 8 | >8 | >8 | >8 | >8 | >8 | >8 | >8 | >8 | >8 |
| 56 | >8 | >8 | >8 | >8 | >8 | >8 | >8 | >8 | >8 | >8 | >8 | >8 |
| 57 | >8 | >8 | 8 | >8 | >8 | >8 | >8 | >8 | >8 | >8 | >8 | >8 |
| 58 | >8 | >8 | 8 | >8 | >8 | >8 | >8 | >8 | >8 | >8 | >8 | >8 |
| 59 | >8 | >8 | >8 | >8 | >8 | >8 | >8 | >8 | >8 | >8 | >8 | >8 |
| 60 | >8 | >8 | 8 | >8 | >8 | >8 | >8 | >8 | >8 | >8 | >8 | >8 |
| 61 | >8 | >8 | 4 | >8 | >8 | >8 | >8 | >8 | >8 | ~8 | >8 | ~8 |
| 62 | >8 | >8 | 8 | >8 | >8 | >8 | >8 | >8 | >8 | >8 | >8 | >8 |
| 63 | >8 | >8 | 4 | >8 | >8 | >8 | >8 | >8 | >8 | >8 | >8 | >8 |
| 64 | >8 | >8 | 0.25 | >8 | >8 | 4 | >8 | >8 | >8 | >8 | >8 | >8 |
| 65 | >8 | >8 | >8 | >8 | >8 | >8 | >8 | >8 | >8 | >8 | >8 | >8 |
| 66 | >8 | >8 | 4 | >8 | >8 | >8 | >8 | >8 | >8 | 8 | >8 | >8 |
| 67 | >8 | >8 | 4 | >8 | >8 | >8 | >8 | >8 | >8 | >8 | >8 | >8 |
| 68 | >8 | >8 | 8 | >8 | >8 | >8 | >8 | >8 | >8 | 8 | >8 | >8 |
| 70 | >8 | >8 | 1 | >8 | >8 | >8 | >8 | >8 | >8 | 8 | >8 | >8 |
| 71 | >8 | >8 | 4 | >8 | >8 | >8 | >8 | >8 | >8 | 8 | >8 | 8 |
| 72 | >8 | >8 | >8 | >8 | >8 | >8 | >8 | >8 | >8 | >8 | >8 | >8 |
| 73 | >8 | >8 | 4 | >8 | >8 | >8 | >8 | >8 | >8 | >8 | >8 | >8 |
| 74 | >8 | >8 | 8 | >8 | >8 | >8 | >8 | >8 | >8 | >8 | >8 | >8 |
| 75 | >8 | >8 | ~8 | >8 | >8 | >8 | >8 | >8 | >8 | >8 | >8 | ~8 |
| 76 | >8 | >8 | 8 | >8 | >8 | >8 | >8 | >8 | >8 | >8 | >8 | >8 |
| 78 | >8 | >8 | ~8 | >8 | >8 | >8 | >8 | >8 | >8 | >8 | >8 | >8 |
| 79 | >8 | >8 | >8 | >8 | >8 | >8 | >8 | >8 | >8 | >8 | >8 | >8 |
| 80 | >8 | >8 | >8 | >8 | >8 | >8 | >8 | >8 | >8 | >8 | >8 | >8 |
| 82 | >8 | >8 | >8 | >8 | >8 | >8 | >8 | >8 | >8 | >8 | >8 | >8 |
| 84 | >8 | >8 | 1 | >8 | >8 | >8 | >8 | >8 | >8 | >8 | >8 | >8 |
| 86 | >8 | >8 | 4 | >8 | >8 | >8 | >8 | >8 | >8 | >8 | >8 | >8 |
| 87 | >8 | >8 | 2 | >8 | >8 | >8 | >8 | >8 | >8 | >8 | >8 | >8 |
| 88 | >8 | >8 | >8 | >8 | >8 | >8 | >8 | >8 | >8 | >8 | >8 | >8 |

TABLE 6-continued

MIC values determined for gyramide compounds.

MIC (µg/mL)

| No. | A | B | C | D | E | F | G | H | I | J | K | L |
|---|---|---|---|---|---|---|---|---|---|---|---|---|
| 89 | >8 | >8 | 0.5 | >8 | >8 | 8 | >8 | >8 | >8 | >8 | >8 | >8 |
| 92 | >8 | >8 | 8 | >8 | >8 | >8 | >8 | >8 | >8 | >8 | >8 | >8 |
| 93 | >8 | >8 | >8 | >8 | >8 | >8 | >8 | >8 | >8 | >8 | >8 | >8 |
| 94 | >8 | >8 | 8 | >8 | >8 | >8 | >8 | >8 | >8 | >8 | >8 | >8 |
| 95 | >8 | >8 | >8 | >8 | >8 | >8 | >8 | >8 | >8 | >8 | >8 | >8 |
| 96 | >8 | >8 | 1 | >8 | >8 | ~8 | >8 | >8 | >8 | >8 | >8 | >8 |
| 97 | >8 | >8 | 4 | >8 | >8 | >8 | >8 | >8 | >8 | >8 | >8 | >8 |
| 98 | >8 | >8 | >8 | >8 | >8 | >8 | >8 | >8 | >8 | >8 | >8 | >8 |
| 99 | >8 | >8 | 2 | >8 | >8 | >8 | >8 | >8 | >8 | >8 | >8 | >8 |
| 100 | >8 | >8 | 2 | >8 | >8 | >8 | >8 | >8 | >8 | >8 | >8 | >8 |
| 101 | >8 | >8 | 2 | >8 | >8 | >8 | ~8 | >8 | 8 | >8 | >8 | >8 |
| 104 | >8 | >8 | >8 | >8 | >8 | >8 | >8 | >8 | >8 | >8 | >8 | >8 |
| 105 | >8 | >8 | 0.125 | >8 | >8 | 8 | >8 | >8 | >8 | >8 | >8 | >8 |
| 106 | >8 | >8 | >8 | >8 | >8 | >8 | >8 | >8 | >8 | >8 | >8 | >8 |
| 107 | >8 | >8 | >8 | >8 | >8 | >8 | >8 | >8 | >8 | >8 | >8 | >8 |
| 108 | >8 | >8 | >8 | >8 | >8 | >8 | >8 | >8 | >8 | >8 | >8 | >8 |
| 109 | >8 | >8 | 0.5 | >8 | >8 | 8 | >8 | >8 | >8 | >8 | >8 | >8 |
| 111 | >8 | >8 | >8 | >8 | >8 | >8 | >8 | >8 | >8 | >8 | >8 | >8 |
| 112 | >8 | >8 | 0.25 | >8 | >8 | 4 | >8 | >8 | >8 | >8 | >8 | >8 |
| 115 | >8 | >8 | >8 | >8 | >8 | >8 | >8 | >8 | >8 | >8 | >8 | >8 |
| 116 | >8 | >8 | >8 | >8 | >8 | >8 | >8 | >8 | >8 | >8 | >8 | >8 |
| 117 | >8 | >8 | >8 | >8 | >8 | >8 | >8 | >8 | >8 | >8 | >8 | >8 |
| 118 | >8 | >8 | >8 | >8 | >8 | >8 | >8 | >8 | >8 | >8 | >8 | >8 |
| 119 | >8 | >8 | >8 | >8 | >8 | >8 | >8 | >8 | >8 | >8 | >8 | >8 |
| 120 | >8 | >8 | ~8 | >8 | >8 | >8 | >8 | >8 | >8 | >8 | >8 | >8 |
| 121 | >8 | >8 | ~8 | >8 | >8 | >8 | >8 | >8 | >8 | >8 | >8 | >8 |
| 122 | >8 | >8 | 4 | >8 | >8 | >8 | >8 | >8 | ~8 | >8 | >8 | >8 |
| 123 | >8 | >8 | >8 | >8 | >8 | >8 | >8 | >8 | >8 | >8 | >8 | >8 |
| 124 | >8 | >8 | >8 | >8 | >8 | >8 | >8 | >8 | >8 | >8 | >8 | >8 |
| 125 | >8 | >8 | >8 | >8 | >8 | >8 | >8 | >8 | >8 | >8 | >8 | >8 |
| 126 | >8 | >8 | >8 | >8 | >8 | >8 | >8 | >8 | >8 | >8 | >8 | >8 |
| 127 | >8 | >8 | 4 | >8 | >8 | >8 | >8 | >8 | >8 | >8 | >8 | >8 |
| 128 | >8 | >8 | 8 | >8 | >8 | >8 | >8 | >8 | >8 | >8 | >8 | >8 |
| 129 | >8 | >8 | >8 | >8 | >8 | >8 | >8 | >8 | >8 | >8 | >8 | >8 |
| 130 | >8 | >8 | ~8 | >8 | >8 | ~8 | >8 | >8 | >8 | >8 | >8 | >8 |
| 131 | >8 | >8 | 8 | >8 | >8 | >8 | >8 | >8 | >8 | >8 | >8 | >8 |
| 132 | >8 | >8 | >8 | >8 | >8 | >8 | >8 | >8 | >8 | >8 | >8 | >8 |
| 133 | >8 | >8 | >8 | >8 | >8 | >8 | >8 | >8 | >8 | >8 | >8 | >8 |
| 134 | >8 | >8 | 4 | >8 | >8 | ~8 | >8 | >8 | >8 | >8 | >8 | >8 |
| 135 | >8 | >8 | 8 | >8 | >8 | >8 | >8 | >8 | >8 | >8 | >8 | >8 |
| 136 | >8 | >8 | ~8 | >8 | >8 | >8 | >8 | >8 | >8 | >8 | >8 | >8 |
| 137 | >8 | >8 | 2 | >8 | >8 | >8 | >8 | >8 | >8 | >8 | >8 | >8 |
| 138 | >8 | >8 | >8 | >8 | >8 | >8 | >8 | >8 | >8 | >8 | >8 | >8 |
| 139 | >8 | >8 | >8 | >8 | >8 | >8 | >8 | >8 | >8 | >8 | >8 | >8 |
| 140 | >8 | >8 | <0.0625 | >8 | >8 | 4 | >8 | >8 | >8 | >8 | >8 | >8 |
| 141 | >8 | >8 | ~8 | >8 | >8 | >8 | >8 | >8 | >8 | >8 | >8 | >8 |
| 142 | >8 | >8 | 2 | >8 | >8 | >8 | >8 | >8 | >8 | >8 | >8 | >8 |
| 144 | >8 | >8 | 8 | >8 | >8 | >8 | >8 | >8 | >8 | >8 | >8 | >8 |
| 145 | >8 | >8 | 8 | >8 | >8 | >8 | >8 | >8 | >8 | >8 | >8 | >8 |
| 146 | >8 | >8 | 8 | >8 | >8 | >8 | >8 | >8 | >8 | >8 | >8 | >8 |
| 147 | >8 | >8 | 8 | >8 | >8 | >8 | >8 | >8 | >8 | >8 | >8 | >8 |
| 148 | >8 | >8 | 8 | >8 | >8 | >8 | >8 | >8 | >8 | >8 | >8 | >8 |
| 149 | >8 | >8 | >8 | >8 | >8 | >8 | >8 | >8 | >8 | >8 | >8 | >8 |
| 150 | >8 | >8 | >8 | >8 | >8 | >8 | >8 | >8 | >8 | >8 | >8 | >8 |
| 151 | >8 | >8 | ~8 | >8 | >8 | >8 | >8 | >8 | >8 | >8 | >8 | >8 |
| 152 | >8 | >8 | 8 | >8 | >8 | >8 | >8 | >8 | >8 | >8 | >8 | >8 |
| 153 | >8 | >8 | 8 | >8 | >8 | >8 | >8 | >8 | >8 | >8 | >8 | >8 |
| 154 | >8 | >8 | >8 | >8 | >8 | >8 | >8 | >8 | >8 | >8 | >8 | >8 |
| 155 | >8 | >8 | >8 | >8 | >8 | >8 | >8 | >8 | >8 | >8 | >8 | >8 |
| 157 | >8 | >8 | >8 | >8 | >8 | >8 | >8 | >8 | >8 | >8 | >8 | >8 |
| 158 | >8 | >8 | >8 | >8 | >8 | >8 | >8 | >8 | >8 | >8 | >8 | >8 |
| 159 | >8 | >8 | >8 | >8 | >8 | >8 | >8 | >8 | >8 | >8 | >8 | >8 |
| 160 | >8 | >8 | >8 | >8 | >8 | >8 | >8 | >8 | >8 | >8 | >8 | >8 |
| 161 | >8 | >8 | >8 | >8 | >8 | >8 | >8 | >8 | >8 | >8 | >8 | >8 |
| 162 | >8 | >8 | >8 | >8 | >8 | >8 | >8 | >8 | >8 | >8 | >8 | >8 |
| 163 | >8 | >8 | >8 | >8 | >8 | >8 | >8 | >8 | >8 | >8 | >8 | >8 |
| 164 | >8 | >8 | >8 | >8 | >8 | >8 | >8 | >8 | >8 | >8 | >8 | >8 |
| 165 | >8 | >8 | 4 | >8 | >8 | >8 | >8 | >8 | >8 | >8 | >8 | >8 |
| 166 | >8 | >8 | 2 | >8 | >8 | ~8 | >8 | >8 | >8 | >8 | >8 | >8 |
| 167 | >8 | >8 | >8 | >8 | >8 | >8 | >8 | >8 | >8 | >8 | >8 | >8 |
| 168 | >8 | >8 | 0.25 | >8 | >8 | ~8 | ~8 | >8 | >8 | >8 | >8 | >8 |
| 169 | >8 | >8 | >8 | >8 | >8 | >8 | >8 | >8 | >8 | >8 | >8 | >8 |
| 170 | >8 | >8 | 2 | >8 | >8 | >8 | >8 | >8 | >8 | >8 | >8 | >8 |
| 171 | >8 | >8 | 1 | >8 | >8 | >8 | >8 | >8 | >8 | >8 | >8 | >8 |
| 173 | >8 | >8 | >8 | >8 | >8 | >8 | >8 | >8 | >8 | >8 | >8 | >8 |
| 174 | >8 | >8 | >8 | >8 | >8 | >8 | >8 | >8 | >8 | >8 | >8 | >8 |
| 175 | >8 | >8 | >8 | >8 | >8 | >8 | >8 | >8 | >8 | >8 | >8 | >8 |
| 176 | >8 | >8 | 8 | >8 | >8 | >8 | >8 | >8 | >8 | >8 | >8 | >8 |
| 177 | >8 | >8 | 2 | >8 | >8 | >8 | >8 | >8 | >8 | >8 | >8 | >8 |
| 178 | >8 | >8 | >8 | >8 | >8 | >8 | >8 | >8 | >8 | >8 | >8 | >8 |
| 179 | >8 | >8 | >8 | >8 | >8 | >8 | >8 | >8 | >8 | >8 | >8 | >8 |
| 180 | >8 | >8 | >8 | >8 | >8 | >8 | >8 | >8 | >8 | >8 | >8 | >8 |
| 181 | >8 | >8 | >8 | >8 | >8 | >8 | >8 | >8 | >8 | >8 | >8 | >8 |
| 183 | >8 | >8 | 0.5 | >8 | >8 | 8 | >8 | >8 | >8 | >8 | >8 | >8 |

A *E. coli* MG1655
B *E. coli* BW25113
C *E. coli* JW5503 (deltolC)
D *Edwardsiella tarda*
E *Klebsiella pneumoniae* subsp. *pneumoniae*
F *Salmonella enterica* subsp. *enterica* Typhimurium
G *Shigella flexneri*
H *Staphylococcus aureus* subsp. *aureus*
I *Staphylococcus saprophyticus* subsp. *saprophyticus*
J *Staphylococcus epidermidis*
K *Streptococcus agalactiae*
L *Streptococcus pyogenes*

In addition to the activity summarized in Table 6, Compound 91 also exhibited MIC values of 8 µg/mL against *Bacillus subtilis* 168, *Bacillus cereus*, and *Enterococcus faecium*. Each of Compounds 1-90 and 92-183 exhibited MIC values above 8 µg/mL against *Bacillus subtilis* 168, *Bacillus cereus*, and *Enterococcus faecium*. Each of compounds 1-183 exhibited MIC values above 8 µg/mL against *Acinetobacter baumannii*, *Enterobacter aerogenes*, *Morganella morganii* subsp. *morganii*, *Pseudomonas aeruginosa*, and *Enterococcus faecalis*.

In a separate set of experiments, MIC values for highly active gyramide compounds were determined against 20 strains of bacteria. The MIC values against the 20 strains are set forth in Table 7.

TABLE 7

MIC values determined for gyramide compounds.

MIC (µg/mL)

| Cmpd. no./name | *E. coli* MG1655 | *E. coli* BW25113 | *E. coli* JW5503 (deltolC) | *Acinetobacter baumannii* | *Edwardsiella tarda* |
|---|---|---|---|---|---|
| 77 | 16 | 8 | 0.125 | >16 | 16 |
| 113 | 16 | 8 | 0.125 | >16 | 16 |
| 156 | 16 | 16 | 0.125 | >16 | 16 |

TABLE 7-continued

MIC values determined for gyramide compounds.

| Cmpd. no./name | | | | | |
|---|---|---|---|---|---|
| 91 | 8 | 8 | <0.0078 | >16 | 8 |
| 143 | 16 | 8 | <0.0078 | >16 | 8 |
| Gyramide C2 | 16 | 16 | 0.015 | >16 | 16 |

| Cmpd. no./name | Enterobacter aerogenes | Klebsiella pneumoniae subsp. pneumoniae | Morganella morganii subsp. morganii | Pseudomonas aeruginosa | Salmonella enterica subsp. enterica typhimurium |
|---|---|---|---|---|---|
| 77 | >16 | >16 | >16 | >16 | 2 |
| 113 | >16 | >16 | >16 | >16 | 4 |
| 156 | >16 | >16 | >16 | >16 | 4 |
| 91 | >16 | >16 | >16 | >16 | 4 |
| 143 | >16 | >16 | >16 | >16 | 2 |
| Gyramide C2 | >16 | >16 | >16 | >16 | 2 |

| Cmpd. no./name | Shigella flexneri | Bacillus subtilis 168 | Bacillus cereus | Enterococcus faecalis | Enterococcus faecium |
|---|---|---|---|---|---|
| 77 | 4 | ND | ND | ND | ND |
| 113 | 8 | ND | ND | ND | ND |
| 156 | 8 | ND | ND | ND | ND |
| 91 | 4 | 8 | 8 | 16 | 8 |
| 143 | 4 | >16 | >16 | >16 | >16 |
| Gyramide C2 | 8 | >16 | >16 | >16 | >16 |

| Cmpd. no./name | Staphylococcus aureus subsp. aureus | Staphylococcus saprophyticus subsp. saprophyticus | Staphylococcus epidermidis | Streptococcus agalactiae | Streptococcus pyogenes |
|---|---|---|---|---|---|
| 77 | ND | ND | ND | ND | ND |
| 113 | ND | ND | ND | ND | ND |
| 156 | ND | ND | ND | ND | ND |
| 91 | 8 | 8 | 8 | 8 | 4 |
| 143 | >16 | >16 | >16 | >16 | >16 |
| Gyramide C2 | >16 | >16 | >16 | >16 | >16 |

ND = not determined.

Example 4. Structural Biological Studies of DNA Gyrase with Gyramide C2

Protein Co-Crystallization of *Staphylococcus aureus* GyrBAfus Protein with dsDNA and Gyramide C2. A nonfunctional fusion of DNA gyrase was prepared using a traditional Ni-affinity resin protocol. DNA gyrase is a heterotetramer of structure $A_2B_2$ and a fusion protein was prepared by transcriptionally fusing truncated forms of the A and B subunits. The C-terminal end of the B subunit was connected to the N-terminal end of the A subunit. Two regions of the amino acid sequence were removed to make the protein non-functional and stable for crystallization (this approach has been used previously to solve the gyrase crystal structure). The DNA wrapping region of the A subunit of gyrase and the ATPase domain of the B subunit were deleted from the construct. The result fusion protein (referred to as GyrBAfus) is unable to hydrolyze ATP and wrap DNA around the protein; both activities are required to introduce negative supercoils into DNA.

The fusion protein was dialyzed with a 20-20 base pair DNA segment to form the GyrBAfus:20-20 bp DNA complex (which is referred to herein as the apo-complex). Using the apo-complex and gyramide C2, crystallization conditions which had been previously optimized in related system were evaluated (determined for crystallization of *Escherichia coli* GyrBAfus with 1 mM gyramide A). Using these optimized conditions, the apo-complex of *S. aureus* was crystallized and the complex was then co-crystallized with 1 mM gyramide C2. In both the apo and co-crystal conditions, 100 μm-long crystals formed, which were soaked in a solution of 5 mM gyramide C2 before freezing the crystals for X-ray diffraction. After screening the frozen crystals with X-ray diffraction at Argonne National laboratory, the crystals were identified to consist of apo-complex without gyramide C2 bound. Accordingly, a new general screen of 144 conditions with apo-complex and higher concentrations of gyramide C2 was evaluated. The screen resulted in 2 promising conditions that produced crystals with morphologies different from those observed previously. The refined conditions did not produce crystals that were large enough for X-ray diffraction, but additional screening of 48 additives was evaluated to promote crystal growth. This latter screen produced three promising additives that were optimized resulting in crystals that were 50 μm in length.

NMR Binding Studies of gyramide C2 to *Staphylococcus aureus* GyrBAfus Protein. The binding affinity of gyramide C2 to the non-functional *S. aureus* DNA gyrase fusion (GyrBSAfus) in the presence of a 20-base pair DNA strand (apo-complex, as defined above) was investigated. The size and position of the aromatic peaks in the $^1H$ NMR spectra of 50 μM gyramide C2 was compared with that obtained from a solution of 50 M gyramide C2 and *S. aureus*

GyrBAfus (20 mg/mL) in 10% $D_2O$/crystallization buffer. The aromatic peaks associated with gyramide C2 disappeared in the presence of GyrBAfus. To determine if the presence of DNA would change the result, $^1$HNMR spectra of samples containing 50 µM gyramide C2 with 1:1.2 GyrBAfus:20-20 bp DNA complex were compared with and a solution of 50 µM gyramide C2 containing the 20-20 bp DNA (120 µM). By titrating different concentrations of 1:1 GyrBAfus:20-20 bp DNA into a constant concentration of gyramide C2 at (50 µM), the $K_d$ for the association was determined as <50 µM.

Example 5. Gyrase Inhibitory Activity of Gyramide C2.

The $IC_{50}$ of gyramide C2 against *E. coli* DNA gyrase was determined using a known gel shift assay (see, *ACS Med. Chem. Lett.*, 2011, 2, 289-292). The $IC_{50}$ of gyramide C2 was surprisingly low in comparison to known gyrase inhibitors ciprofloxacin and novobiocin, as shown in Table 8

TABLE 8

$IC_{50}$ of gyramide C2 and known gyrase inhibitors against *E. coli* DNA gyrase.

| | WT Gyrase | | |
|---|---|---|---|
| Trial | Gyramide C2 (nM) | Ciprofloxacin (nM) | Novobiocin (nM) |
| 1 | 84.54 | 701.1 | 549.8 |
| 2 | 119.1 | 1,135.0 | 659.1 |
| 3 | 162.7 | 867.7 | 778.5 |
| Average | 122.1 ± 39.2 | 901.3 ± 218.9 | 662.5 ± 114.4 |

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having a structure selected from the group consisting of:

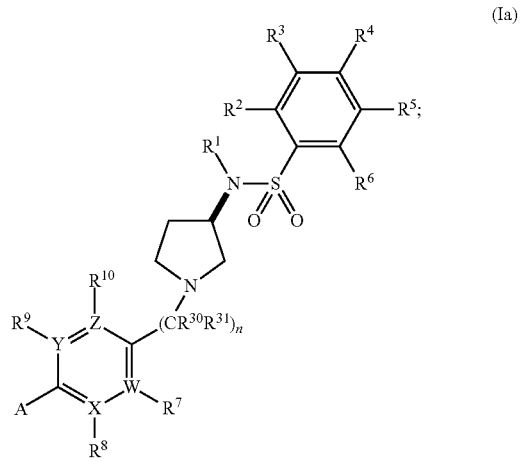

or a pharmaceutically acceptable salt thereof, wherein

A is selected from the group consisting of $C_{6-10}$aryl, $C_{4-9}$heteroaryl, $C_{3-8}$cycloalkyl, $C_{3-8}$heterocycloalkyl, —$OC_{6-10}$aryl, —$OC_{4-9}$heteroaryl, —$OC_{3-8}$cycloalkyl, and —$OC_{3-8}$heterocycloalkyl;

W, X, Y, and Z are in each instance independently selected from the group consisting of C and N;

$R^1$ is selected from the group consisting of H and $C_{2-6}$alkyl;

each $R^2$, $R^3$, $R^4$, $R^5$, and $R^6$ is independently selected from the group consisting of hydrogen, $C_{1-6}$alkyl, $C_{1-6}$alkoxy, cyano, halo$C_{1-6}$alkyl, halogen, and halo $C_{1-6}$alkoxy;

each $R^7$, $R^8$, $R^9$, $R^{10}$, $R^{30}$, and $R^{31}$ is independently selected from the group consisting of hydrogen, $C_{1-6}$alkyl, $C_{2-6}$alkenyl, $C_{2-6}$alkynyl, $C_{1-6}$alkoxy, acetyl, carboxy, $C_{3-8}$cycloalkyl, cyano, halo$C_{1-6}$alkyl, formyl, halogen, hydroxyl, halo$C_{1-6}$alkoxy, amino, amino $C_{1-6}$alkyl, di$C_{1-6}$alkylamino, azido, mercapto, nitro, sulphamoyl, sulfo, and ureido; or optionally, two of $R^2$, $R^3$, $R^4$, $R^5$, $R^6$, $R^7$, $R^8$, $R^9$, $R^{10}$, $R^{30}$, and $R^{31}$ on adjacent ring vertices are combined to form a fused benzene ring, a fused 5- or 6-membered heteroaryl ring, a fused 5- or 6-membered cycloalkyl ring, or a fused 5- or 6-membered heterocycloalkyl ring;

$R^7$ is absent when W is N;

$R^8$ is absent when X is N;

$R^9$ is absent when Y is N;

$R^{10}$ is absent when Z is N;

subscript n is an integer selected from the group consisting of 1, 2, and 3;

when A is phenyl or optionally substituted phenyl, and $R^3$ or $R^5$ is halo, then $R^2$ and $R^6$ are other than methyl or chloro; and when is A phenyl or optionally substituted phenyl, and $R^4$ is iodo or ethynyl, then at least one of $R^2$, $R^3$, $R^5$, and $R^6$ is other than hydrogen.

2. The compound of claim 1, wherein A has a structure selected from the group consisting of:

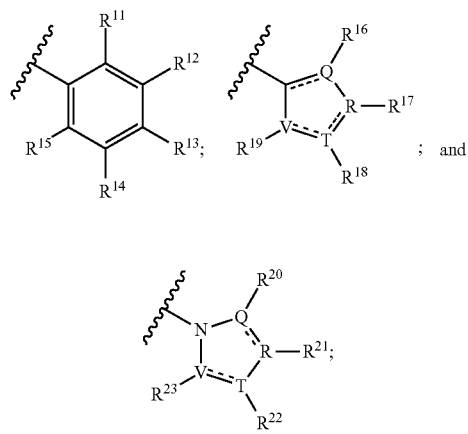

wherein

R¹¹, R¹², R¹³, R¹⁴, R¹⁵, R¹⁶, R¹⁷, R¹⁸, R¹⁹, R²⁰, R²¹, R²², and R²³ are in each instance independently selected from the group consisting of hydrogen, $C_{1-6}$alkyl, $C_{2-6}$alkenyl, $C_{2-6}$alkynyl, $C_{1-6}$alkoxy, acetyl, carboxy, $C_{3-8}$cycloalkyl, cyano, halo$C_{1-6}$alkyl, formyl, halogen, hydroxyl, halo$C_{1-6}$alkoxy, amino, amino$C_{1-6}$alkyl, di$C_{1-6}$alkylamino, azido, mercapto, nitro, sulphamoyl, sulfo, and ureido;

Q, R, T, and V are each independently selected from the group consisting of C, N, 0, and S R¹⁶ and R²⁰ are absent when Q is N, O, or S;

R¹⁷ and R²¹ are absent when R is N, O, or S;

R¹⁸ and R²² are absent when T is N, O, or S;

R¹⁹ and R²³ are absent when V is N, O, or S;

each dashed line is absent, indicating a single bond, or present, indicating a double bond; and each wavy line represents the point of attachment to the ring to which A is attached.

3. The compound of claim 2, wherein A is selected from the group consisting of phenyl, substituted phenyl, thiophenyl, and pyrazolyl.

4. The compound of claim 2, wherein A is selected from the group consisting of phenyl, 4-chlorophenyl, 3-chlorophenyl, thiophen-2-yl, and 1H-pyrazol-1-yl.

5. The compound of claim 1, wherein A is selected from the group consisting of —O$C_{6-10}$aryl, —O$C_{4-9}$heteroaryl, —O$C_{3-8}$cycloalkyl, and —O$C_{3-8}$heterocycloalkyl.

6. The compound of claim 5, wherein A is selected from the group consisting of cyclopropyloxy, cyclobutyloxy, and cyclopentyloxy.

7. The compound of claim 1, wherein each R², R³, R⁴, R⁵, and R⁶ is independently selected from the group consisting of hydrogen, trifluoromethyl, and trifluoromethoxy.

8. The compound of claim 1, wherein both R³⁰ and R³¹ are hydrogen.

9. The compound of claim 1, which is selected from the group consisting of

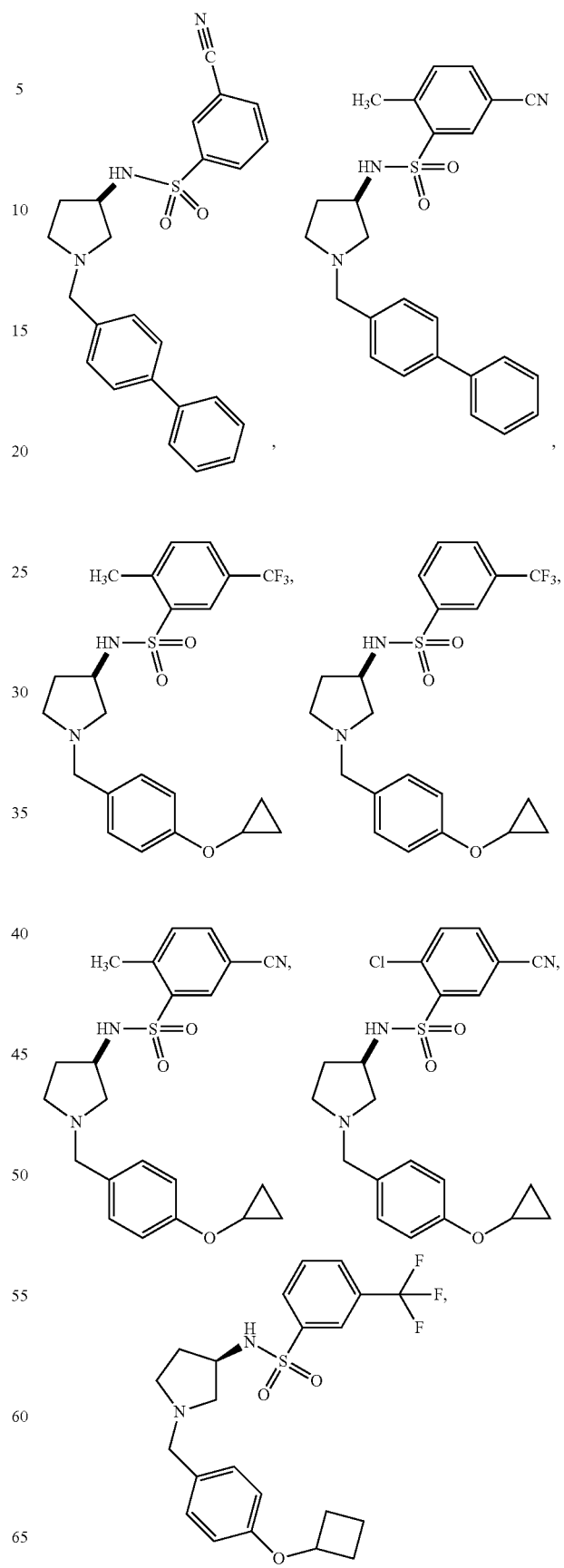

151
-continued
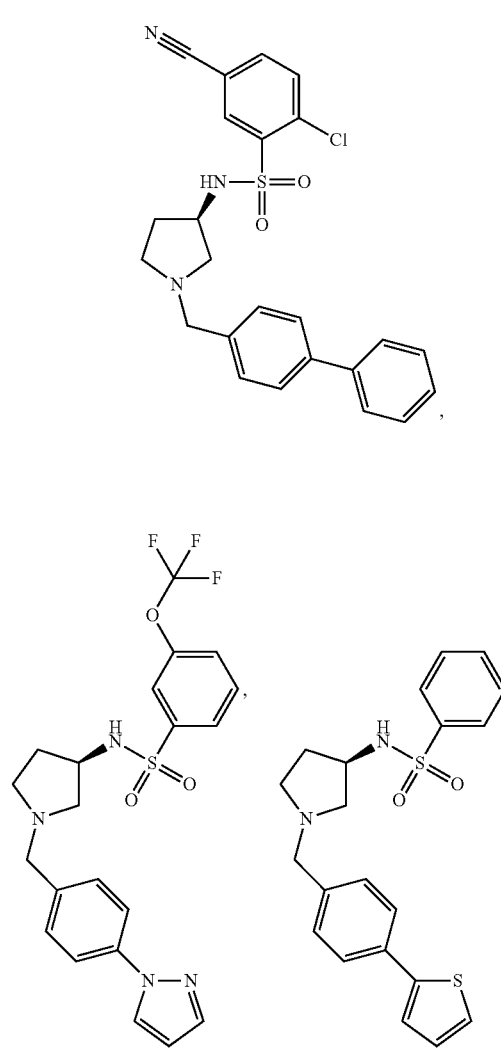
152
-continued
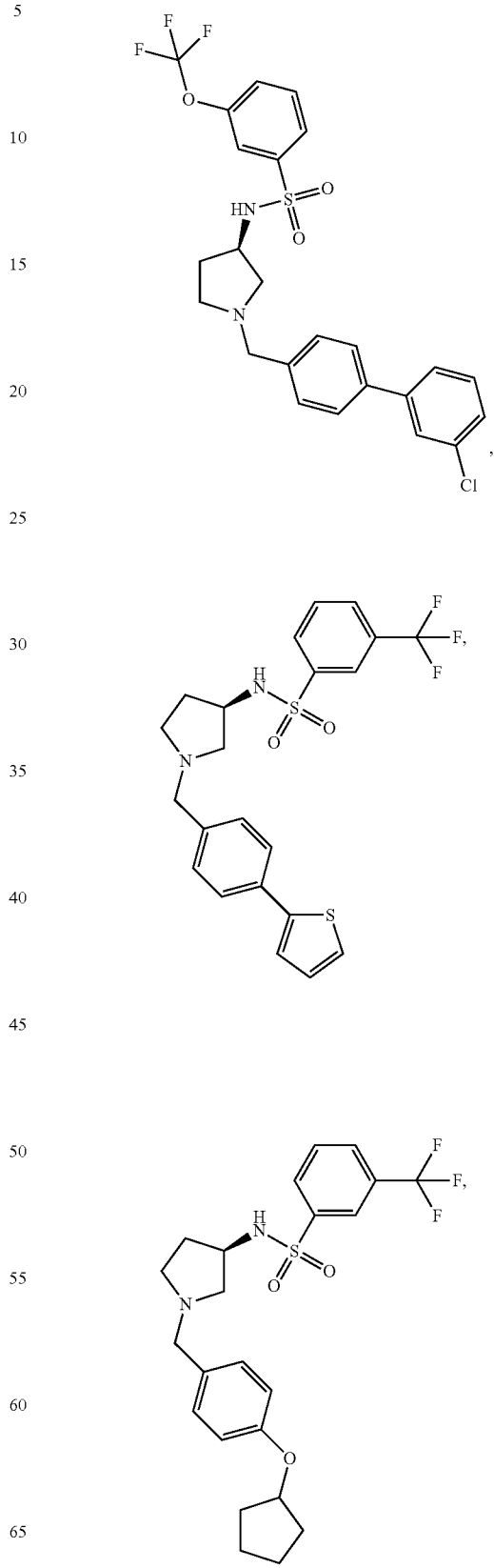

-continued
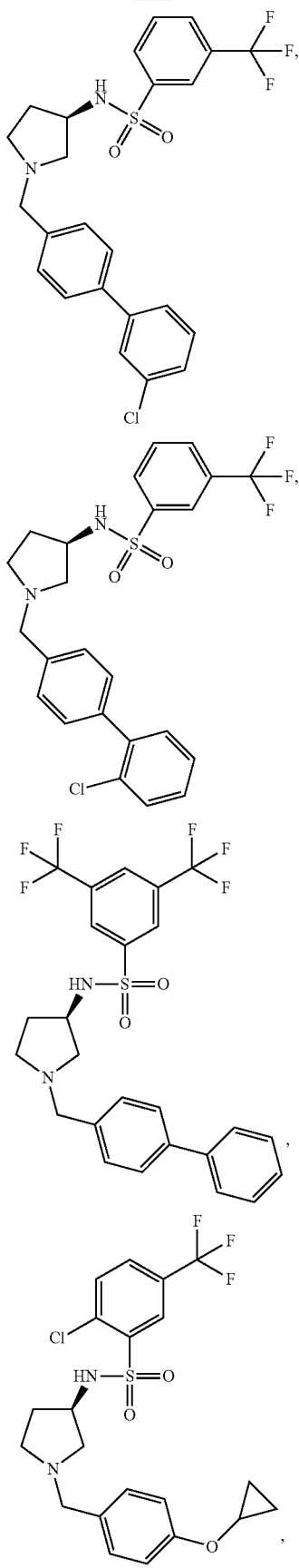
-continued
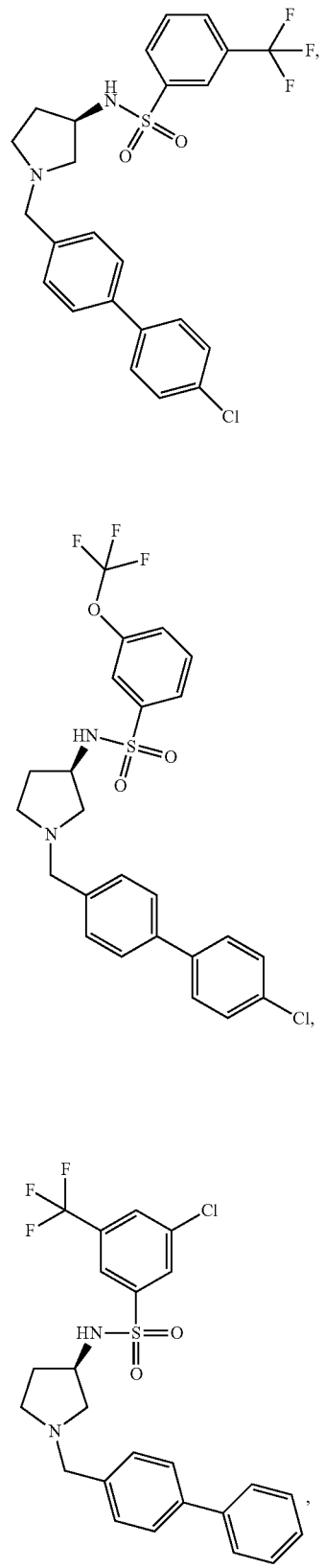

-continued

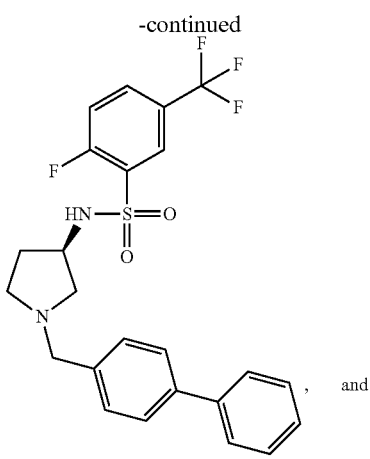

, and

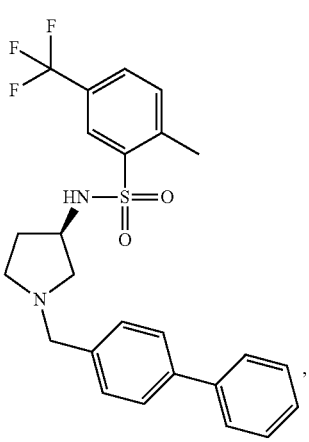

or a pharmaceutically acceptable salt thereof.

10. The compound of claim 9, which is selected from the group consisting of

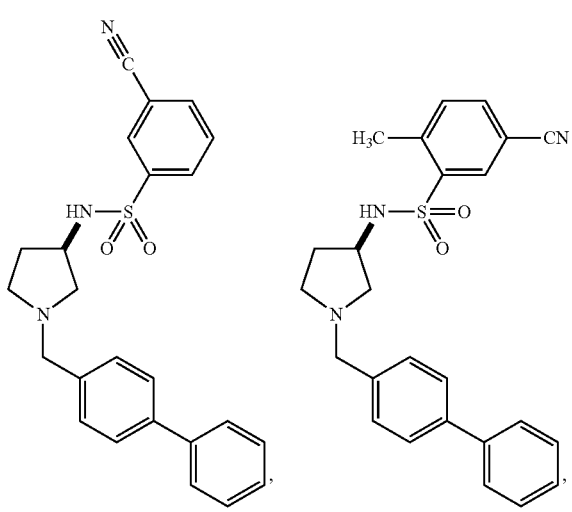

-continued

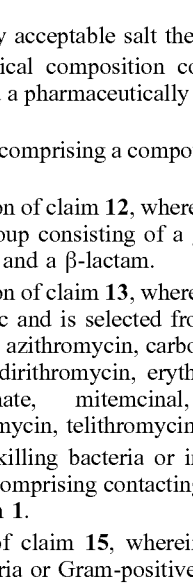

or a pharmaceutically acceptable salt thereof.

11. A pharmaceutical composition comprising a compound of claim 1 and a pharmaceutically acceptable excipient.

12. A composition comprising a compound of claim 1 and an antibiotic.

13. The composition of claim 12, wherein the antibiotic is selected from the group consisting of a gyrase inhibitor, a macrolide antibiotic, and a β-lactam.

14. The composition of claim 13, wherein the antibiotic is a macrolide antibiotic and is selected from the group consisting of ansamycin, azithromycin, carbomycin, cethromycin, clarithromycin, dirithromycin, erythromycin, erythromycin ethylsuccinate, mitemcinal, oleandomycin, roxithromycin, spiramycin, telithromycin, and tylocine.

15. A method of killing bacteria or inhibiting bacterial growth, the method comprising contacting the bacteria with a compound of claim 1.

16. The method of claim 15, wherein the bacteria are Gram-negative bacteria or Gram-positive bacteria.

17. The method of claim 15, wherein the bacteria are selected from the group consisting of Escherichia coli, Enterococcus faecium, Salmonella enterica, Staphylococcus aureus, Streptococcus pneumonia, Klebsiella pneumoniae, Acinetobacter baumannii, Pseudomonas aeruginosa, and Enterobacter species.

18. The method of claim 15, wherein the bacteria are resistant to vancomycin or to fluoroquinolone antibiotics.

19. A method of treating a bacterial infection in a subject in need thereof, the method comprising administering to the subject an effective amount of a compound of claim 1 or a pharmaceutical composition thereof.

20. The method of claim 19, wherein the bacterial infection is resistant to vancomycin or is resistant to fluoroquinolone antibiotics.

* * * * *